United States Patent
Arias et al.

(10) Patent No.: US 8,071,383 B2
(45) Date of Patent: Dec. 6, 2011

(54) D-AMINO ACID SELECTION FOR SOYBEAN

(75) Inventors: Diana Arias, Cary, NC (US); Sara Price, Raleigh, NC (US); Leslie Grist, Raleigh, NC (US); Ming Cheng, Cary, NC (US); Haiping Hong, Morrisville, NC (US); Libby Bernal, Durham, NC (US); Paula Olhoft, Morrisville, NC (US); Hee-Sook Song, Raleigh, NC (US); Luke Mankin, Raleigh, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 428 days.

(21) Appl. No.: 12/293,161

(22) PCT Filed: Mar. 16, 2007

(86) PCT No.: PCT/EP2007/052515
§ 371 (c)(1),
(2), (4) Date: Sep. 16, 2008

(87) PCT Pub. No.: WO2007/107516
PCT Pub. Date: Sep. 27, 2007

(65) Prior Publication Data
US 2009/0083883 A1      Mar. 26, 2009

Related U.S. Application Data

(60) Provisional application No. 60/743,518, filed on Mar. 17, 2006.

(51) Int. Cl.
*C12N 15/82* (2006.01)
*C12N 15/90* (2006.01)
*A01H 5/00* (2006.01)

(52) U.S. Cl. .............. 435/468; 435/320.1; 435/419; 800/288

(58) Field of Classification Search .............. None
See application file for complete search history.

(56) References Cited

U.S. PATENT DOCUMENTS

| | | | |
|---|---|---|---|
| 7,105,349 B2 * | 9/2006 | Nasholm et al. ............. | 435/468 |
| 2001/0034888 A1 | 10/2001 | Olhoft et al. | |
| 2005/0172365 A1 | 8/2005 | Puchta et al. | |
| 2007/0006347 A1 | 1/2007 | Plesch et al. | |
| 2009/0106856 A1 * | 4/2009 | Trifonova et al. ............. | 800/278 |

FOREIGN PATENT DOCUMENTS

| | | |
|---|---|---|
| WO | WO-03/004659 A2 | 1/2003 |
| WO | WO-03/060133 A2 | 7/2003 |
| WO | WO-03/102198 A1 | 12/2003 |
| WO | WO-2005/090581 A1 | 9/2005 |
| WO | WO-2005/090582 A1 | 9/2005 |
| WO | WO-2005/121345 A1 | 12/2005 |
| WO | WO-2006/024509 A2 | 3/2006 |

OTHER PUBLICATIONS

Xia, B.-S., et al., "Nucleotide sequence of a soybean (*Glycine max* L. Merr.) ubiquitin gene," Plant Physiology, 1994, vol. 104, pp. 805-806.
Erikson, O., et al., "A conditional marker gene allowing both positive and negative selection in plants," Nature Biotechnology, 2004, vol. 22, pp. 455-458.
Erikson, O., et al., "The *dsd*A gene from *Escherichia coli* provides a novel selectable marker for plant transformation," Plant Molecular Biology, 2005, vol. 57, pp. 425-433.
Hinchee, M.A.W., et al., "Production of transgenic soybean plants using *Agrobacterium*-mediated DNA transfer," Bio/Technology, 1988, vol. 6, pp. 915-922.
Finer, J.J., et al., "Transformation of soybean via particle bombardment of embryogenic suspension culture tissue," In Vitro Cell Dev Biol., 1991, vol. 27P, pp. 175-182.
Kawalleck, P., et al., "Polyubiquitin gene expression and structural properties of the *ubi*4-2 gene in *Petroselinum crispum*," Plant Molecular Biology, 1993, vol. 21, pp. 673-684.
"Rhodosporidium toruloides D-amino acid oxidase mRNA, complete cds.," EMBL Database, Accession No. U60066, Apr. 3, 1997.
"*E.coli* D-serine deaminase (dsdA) gene, complete cds.," EMBL Database, Accession No. J01603, Jun. 13, 1985.

* cited by examiner

*Primary Examiner* — Eileen B O Hara
(74) *Attorney, Agent, or Firm* — Connolly Bove Lodge & Hutz, LLP

(57) ABSTRACT

The present invention relates to improved methods and means for transformation of soybean (*Glycine max*) based on a D-alanine and/or D-serine selection.

25 Claims, 3 Drawing Sheets

A          B

D-AMINO ACID SELECTION FOR SOYBEAN

RELATED APPLICATIONS

This application is a national stage application (under 35 U.S.C. 371) of PCT/EP2007/052515, filed Mar. 16, 2007, which claims benefit of U.S. Provisional application 60/743,518, filed Mar. 17, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is SequenceListing_13987_00096. The size of the text file is 115 KB, and the text file was created on May 16, 2011.

FIELD OF THE INVENTION

The present invention relates to improved methods for transformation of soybean (*Glycine max*) based on a D-alanine and/or D-serine selection.

BACKGROUND OF THE INVENTION

The soybean (*Glycine max*) belongs to the Fabaceae (Leguminosae) family. The soybean is thought to have originated in China. Wild types of soybeans are viny in nature, which may explain why soybeans were first introduced in the United States as a hay crop. Introductions from China, Manchuria, Korea and Japan have been important in developing varieties for the United States. Modern breeding efforts to improve the agronomic traits, such as more erect growth, reduced lodging and increased seed size, have been primarily responsible for the development of soybeans into a crop of worldwide importance. The acreage and the proportion of the crop harvested for grain has increased steadily and today soybeans are a major world commodity.

Cultivated soybean has a substantial commercial value throughout the world. Over 50 million hectares worldwide are used to produce an annual crop of soybeans in excess of 100 metric tons with an estimated value exceeding 20 billion dollars. The development of scientific methods useful in improving the quantity and quality of this crop is, therefore, of significant commercial interest. Soybeans are widely used as a source of protein, oil, condiments and chemical feedstock. Significant effort has been expended to improve the quality of cultivated soybean species by conventional plant breeding, and a number of major successes are recorded. The methods of conventional plant breeding have been limited, however, to the movement of genes and traits from one soybean variety to the other.

Modern biotechnological research and development has provided useful techniques for the improvement of agricultural products by plant genetic engineering. Plant genetic engineering involves the transfer of a desired gene or genes into the inheritable germline of crop plants such that those genes can be bred into or among the elite varieties used in modern agriculture. Gene transfer techniques allow the development of new classes of elite crop varieties with improved disease resistance, herbicide tolerance, and increased nutritional value. Various methods have been developed for transferring genes into plant tissues including high velocity microprojection, microinjection, electroporation, direct DNA uptake, and *Agrobacterium*-mediated gene transformation. Although widely used for dicotyledonous plants, DNA delivery using particle bombardment, electroporation, or *Agrobacterium*-mediated delivery into soybean has proven to be difficult. This is due, in part, to the small number of cells that have been found to be totipotent in soybean (Trick 1997). Two methods routinely used are an *Agrobacterium*-based method targeting the cotyledonary-node axillary meristems (Hinchee 1988) and a method using particle bombardment of mature zygotic embryos (Finer 1991).

The lack of effective selective agents is one of the bottlenecks in the efficiency of different soybean transformation methods. The efficacy of tissue culture selection systems depends on many factors including tissue type, size of explant, chemical characteristics of the selectable agent and concentrations and time of application. The most used method of selection is known as negative selection, which employs selection markers that confer resistance against a phytotoxic agent (such as an herbicide or antibiotic). The negative selection markers employed so far are mainly limited to neomycin 3'-O-phosphotransferase (nptII), phosphinothricin acetyltransferases (PAT; also named Bialophos® resistance; bar; de Block 1987; EP 0 333 033; U.S. Pat. No. 4,975,374), 5-enolpyruvylshikimate-3-phosphate synthase (EPSPS; conferring resistance to Glyphosate® (N-(phosphonomethyl)glycine); and hygromycin B. Alternative selection marker systems, such as a system based on D-amino acid metabolizing enzymes (e.g., D-amino acid dehydratases or oxidases), has been recently described on a general basis (WO 03/060133; Erikson 2004). However, no adoption and/or optimization of such a system for use in soybean has been described so far. Accordingly, the object of the present invention is to provide an improved, efficient method for transforming *Glycine max* plants based on D-amino acid selection. This objective is achieved by the present invention.

Although some of the problems linked to the transformation of soybeans have been overcome by the methods described in the art, there is still a significant need for improvement, since all methods known so far have only a low to moderate transformation and—especially—regeneration efficiency. Although significant advances have been made in the field of *Agrobacterium*-mediated transformation methods, a need continues to exist for improved methods to facilitate the ease, speed and efficiency of such methods for transformation of soybean plants. Therefore, it was the objective of the present invention to provide an improved method having higher overall efficiency in the process of generation of transgenic soybean plants. This objective is solved by the present invention.

SUMMARY OF THE INVENTION

A first embodiment of the invention relates to a method for generating a transgenic soybean plant comprising the steps of
a. introducing into a soybean cell or tissue a DNA construct comprising at least one first expression construct comprising a promoter active in said soybean plant and operably linked thereto a nucleic acid sequence encoding an enzyme capable to metabolize D-alanine and/or D-serine, and
b. incubating said soybean cell or tissue of step a) on a selection medium comprising D-alanine and/or D-serine and/or a derivative thereof in a total concentration from about 0.5 mM to about 100 mM for a time period of at least 5 days, and
c. transferring said soybean cell or tissue of step b) to a regeneration medium and regenerating and selecting soybean plants comprising said DNA construct.

While various promoters are known to be functional in soybean and are suitable to carry out the method of the invention, it has been found that especially the ubiquitin promoters result in a surprisingly high efficiency of selection. Thus in a preferred embodiment the promoter active in soybean is a ubiquitin promoter from a dicotyledonous plant. More preferably, the plant ubiquitin promoter is the parsley (*Petroselinum crispum* or *Lomatium foeniculaceum*) ubiquitin promoter or the soybean (*Glycine max*) ubiquitin promoter, most preferably the ubiquitin promoter (or a derivative or fragment thereof as described below). Sequences for the parsley ubiquitin and soybean ubiquitin promoter are provided hereunder. It is known to the person skilled in the art that promoter sequences can be modified (e.g., truncated, fused, mutated) to a large extent without significantly modifying their transcription properties. Thus, in one preferred embodiment of the invention, the promoter active in soybean is selected from the group consisting of a) sequences comprising the sequence as described by SEQ ID NO: 7 or 8, and
b) sequences comprising at least one fragment of at least 50 (preferably 100 or 150, more preferably 200 or 250, even more preferably 300 or 500) consecutive base pairs of the sequence as described by SEQ ID NO: 7 or 8, and having promoter activity in soybean,
c) sequences comprising a sequence having at least 60% (preferably 70% or 75%, more preferably 80% or 85%, even more preferably 90% or 95%, most preferably 98%) identity to the sequence as described by SEQ ID NO: 7 or 8, and having promoter activity in soybean,
d) sequences comprising a sequence hybridizing (preferably under conditions equivalent or equal to hybridization with a buffer solution of 30 to (preferably) 35% formamide, 1 M NaCl, 1% SDS at 37° C., and a wash in 1× to 2×SSC (preferably 1×SSC) at 50 to (preferably) 55° C.), more preferably in 40 to (preferably) 45% formamide, 1.0 M NaCl, 1% SDS at 37° C., and a wash in 0.5× to 1×SSC (preferably 0.5×SSC) at 55 to (preferably) 60° C.), and most preferably in 50% formamide, 1 M NaCl, 1% SDS at 37° C., and a wash in 0.1×SSC at 60 to (preferably) 65° C.) to the sequence as described by SEQ ID NO: 7 or 8, and having promoter activity in soybean.

Preferably, the method of the invention comprises the following steps
(a) providing an axillary meristematic tissue of a primary or higher leaf node of a soybean seedling, and
(b) co-cultivating said axillary meristematic tissue with a Rhizobiaceae bacterium comprising a transgenic T-DNA, said transgenic T-DNA comprising a DNA construct comprising at least one first expression construct comprising a promoter active in said soybean plant and operably linked thereto a nucleic acid sequence encoding an enzyme capable to metabolize D-alanine and/or D-serine
(c) transferring said co-cultivated axillary meristematic tissue on a shoot induction and selection medium comprising
  (i) at least one plant growth factor in a concentration suitable to induce de novo shoot induction from said axillary meristematic tissue, and
  (ii) D-alanine and/or D-serine and/or a derivative thereof in a total concentration from about 3 mM to about 100 mM for, and
  (iii) optionally one or more antibiotics suitable to inhibit Rhizobiaceae bacterium growth,
  and cultivating said co-cultivated axillary meristematic tissue for a period of at least 5 days on said medium until shoots are induced and developed there from and isolating said shoots, and
(d) transferring said isolated shoots to a rooting medium and cultivating said shoots on said rooting medium until said shoots have formed roots, and further regenerating the so derived plantlets into mature plants, which comprise inserted into their genome said transgenic T-DNA.

In one preferred embodiment of the invention the DNA construct or the T-DNA (comprising said first expression cassette for said enzyme capable to metabolize D-alanine and/or D-serine) further comprises at least one second expression construct conferring to said soybean plant an agronomically valuable trait.

The method based on axillary meristematic tissue can employ explant tissue and/or cells from various sources. Preferably, the axillary meristematic tissue of the primary or higher node is provided in a form selected from the group consisting of:
i) the seedling axillary meristem as provided by substantially the entire seedling, and
ii) the leaf axillary meristem as provided by dissecting the primary or higher leafs in a way that the axillary meristematic tissue remains attached to the petioles of the leafs, and
iii) propagated axillary meristem.

In one preferred embodiment of the invention (especially for the method based on axillary meristematic tissue) the media of at least one of step (b) (co-cultivation), and/or (c) (shoot induction and selection), comprises a cytokinin in a concentration equivalent to a concentration of about 1 µM to about 10 µM 6-benzylaminopurine. Furthermore, said media of at least one of step (b), and/or (c) may further comprises between about 0.1 µM and about 2 µM Gibberellic acid (GA3). In addition, said media of at least one of step (b) and/or (c) further comprises at least one thiol compound (such as DTT, or Cysteine).

Various enzymes are known to the person skilled in the art, which can be used as D-serine and/or D-alanine metabolizing enzymes. Preferably, the enzyme capable to metabolize D-alanine and/or D-serine is selected from the group consisting of D-serine ammonia-lyases (EC 4.3.1.18), D-Amino acid oxidases (EC 1.4.3.3), and D-Alanine transaminases (EC 2.6.1.21). More preferably, the enzyme capable to metabolize D-serine is selected from the group consisting of
i) the *E. coli* D-serine ammonia-lyase as encoded by SEQ ID NO: 2, and
ii) enzymes having the same enzymatic activity and an identity of at least 60% (preferably 70% or 75%, more preferably 80% or 85%, even more preferably 90% or 95%, most preferably 98%) to the sequence as encoded by SEQ ID NO: 2, and
ii) enzymes encoded by a nucleic acid sequence capable to hybridize (preferably under conditions equivalent or equal to hybridization with a buffer solution of 30 to (preferably) 35% formamide, 1 M NaCl, 1% SDS at 37° C., and a wash in 1× to 2×SSC (preferably 1×SSC) at 50 to (preferably) 55° C.), more preferably in 40 to (preferably) 45% formamide, 1.0 M NaCl, 1% SDS at 37° C., and a wash in 0.5× to 1×SSC (preferably 0.5×SSC) at 55 to (preferably) 60° C.), and most preferably in 50% formamide, 1 M NaCl, 1% SDS at 37° C., and a wash in 0.1×SSC at 60 to (preferably) 65° C.) to the complement of the sequence described by SEQ ID NO: 1.

For these enzymes selection is preferably done on a medium comprising D-serine in a concentration from about 1 mM to about 100 mM.

Also more preferably, the enzyme capable to metabolize D-serine and/or D-alanine is selected from the group consisting of
i) the *Rhodotorula gracilis* D-amino acid oxidase as encoded by SEQ ID NO: 4 or 6, and ii) enzymes having the same enzymatic activity and an identity of at least 60% (preferably 70% or 75%, more preferably 80% or 85%, even more preferably 90% or 95%, most preferably 98%) to the sequence as encoded by SEQ ID NO: 4 or 6, and iii) enzymes encoded by a nucleic acid sequence capable to hybridize (preferably under conditions equivalent or equal to hybridization with a buffer solution of 30 to (preferably) 35% formamide, 1 M NaCl, 1% SDS at 37° C., and a wash in 1× to 2×SSC (preferably 1×SSC) at 50 to (preferably) 55° C.), more preferably in 40 to (preferably) 45% formamide, 1.0 M NaCl, 1% SDS at 37° C., and a wash in 0.5× to 1×SSC (preferably 0.5×SSC) at 55 to (preferably) 60° C.), and most preferably in 50% formamide, 1 M NaCl, 1% SDS at 37° C., and a wash in 0.1×SSC at 60 to (preferably) 65° C.) to the complement of the sequence described by SEQ ID NO: 3 or 5, For these enzymes selection is preferably done on a medium comprising D-alanine and/or D-serine in a total concentration from about 1 mM to about 100 mM.

There are various was to conduct the selection scheme based on D-amino acids or related compounds hereunder. Preferably, wherein the selection (e.g., of step b) of the general method or step c) of the method based on axillary meristem) is done i) using about 3 to about 20 mM D-alanine and/or D-serine, and/or ii) for about 3 to 4 weeks under dedifferentiating conditions.

Preferably, D-alanine (e.g., if employed as only selection compound) is employed in a concentration of about 0.5 mM to about 100 mM, preferably about 1 mM to about 70 mM, more preferably about 2 mM to about 50 mM, most preferably about 3 mM to about 20 mM. Preferably, D-serine (e.g., if employed as only selection compound) is employed in a concentration of about 0.5 mM to about 100 mM, preferably about 1 mM to about 70 mM, more preferably about 2 mM to about 50 mM, most preferably about 3 mM to about 15 mM.

In one preferred embodiment introduction of the DNA construct is mediated by Rhizobiaceae bacterium mediated transformation. Preferably, the Rhizobiaceae bacterium is a disarmed *Agrobacterium tumefaciens* or *Agrobacterium rhizogenes* bacterium. More preferably, the *Agrobacterium* strain is a disarmed *Agrobacterium rhizogenes* K599 strain.

As mentioned above, especially the employment of ubiquitin promoters had been shown to be advantageous. The constructs provided hereunder are novel and especially useful for carrying out the invention. Furthermore, they may provide use also in other plant species. In consequence, another embodiment of the invention relates to a heterologous nucleotide sequence comprising a) a promoter selected from the group consisting of a ubiquitin promoter from a dicotyledonous plant specie, and operably linked thereto b) a nucleic acid sequence encoding an enzyme capable to metabolize D-alanine and/or D-serine, wherein said promoter is heterologous with respect to said nucleic acid sequence.

Preferably, the ubiquitin promoter is the parsley ubiquitin promoter or the soybean ubiquitin promoter. As described above the sequences of these promoters can be modified without changing their transcription capability. In consequence another embodiment of the invention relates to a heterologous nucleotide sequence comprising a) a promoter selected from the group consisting of i) sequences comprising the sequence as described by SEQ ID NO: 7 or 8, and ii) sequences comprising at least one fragment of at least 50 (preferably 100 or 150, more preferably 200 or 250, even more preferably 300 or 500) consecutive base pairs of the sequence as described by SEQ ID NO: 7 or 8, and having promoter activity in soybean, iii) sequences comprising a sequence having at least 60% (preferably 70% or 75%, more preferably 80% or 85%, even more preferably 90% or 95%, most preferably 98%) identity to the sequence as described by SEQ ID NO: 7 or 8, and having promoter activity in soybean, iv) sequences comprising a sequence hybridizing (preferably under conditions equivalent or equal to hybridization with a buffer solution of 30 to (preferably) 35% formamide, 1 M NaCl, 1% SDS at 37° C., and a wash in 1× to 2×SSC (preferably 1×SSC) at 50 to (preferably) 55° C.), more preferably in 40 to (preferably) 45% formamide, 1.0 M NaCl, 1% SDS at 37° C., and a wash in 0.5× to 1×SSC (preferably 0.5×SSC) at 55 to (preferably) 60° C.), and most preferably in 50% formamide, 1 M NaCl, 1% SDS at 37° C., and a wash in 0.1×SSC at 60 to (preferably) 65° C.) to the sequence as described by SEQ ID NO: 7 or 8, and having promoter activity in soybean, and b) a nucleic acid sequence encoding an enzyme capable to metabolize D-alanine and/or D-serine, wherein said promoter is heterologous with respect to said nucleic acid sequence.

Another embodiment of the invention relates to the soybean cells and plants made by the method provided hereunder. Thus, another embodiment relates to a soybean plant or cell comprising a DNA construct comprising a promoter active in said soybean plants or cells and operably linked thereto a nucleic acid sequence encoding an enzyme capable to metabolize D-alanine or D-serine, wherein said promoter is heterologous in relation to said enzyme encoding sequence. Preferably, the promoter and/or the enzyme capable to metabolize D-alanine or D-serine are defined as above. More preferably, said soybean plant or cell is further comprising at least one second expression construct conferring to said soybean plant an agronomically valuable trait. Other embodiments of the invention relate to parts of said soybean plant including but not limited to soybean seeds (soybeans) and their use for food, feed, and industrial purposes.

When based on D-amino acid oxidases the method of the invention can be used as a combined selection/marker deletion scheme. Based on the D-amino acid employed, D-amino acid oxidases can act either as negative or counter selection marker. Thus, the invention further provides a method for providing soybean cells and plants (which are preferably marker free), said method comprises the steps of:

i) transforming a soybean plant cell with a first DNA construct comprising a) at least one first expression construct comprising a promoter active in said soybean plant and operably linked thereto a nucleic acid sequence encoding a D-amino acid oxidase enzyme, wherein said first expression cassette is flanked by sequences which allow for specific deletion of said first expression cassette, and b) at least one second expression cassette suitable for conferring to said plant an agronomically valuable trait, wherein said second expression cassette is not localized between said sequences which allow for specific deletion of said first expression cassette, and ii) treating said transformed soybean plant cells of step i) with a first compound selected from the group consisting of D-alanine, D-serine or derivatives thereof in a phytotoxic concentration and selecting plant cells comprising in their genome said first DNA construct, conferring resistance to said transformed plant cells against said first compound by expression of said D-amino acid oxidase, and iii) inducing deletion of said first expression cassette from the genome of said transformed plant cells and treating said plant cells with a second compound selected from the group consisting of D-isoleucine, D-valine and derivatives thereof in a concentration toxic to plant cells still comprising said first expression cassette, thereby selecting plant cells comprising said second expression cassette but lacking said first expression cassette.

Preferably, the promoter sequences and D-amino acid oxidase enzymes are defined as above for the general method.

There is a shortage of efficient transformation systems and especially selection markers for soybean. This shortage refers especially to approaches, which rely on multiple subsequent transformations. One way to overcome this problem is the combined selection and marker deletion method provided above. Another method is based on combining different selection systems. In consequence, another embodiment of the invention relates to a method for subsequent transformation of at least two DNA constructs into a soybean plant comprising the steps of:

a) a transformation with a first construct said construct comprising at least one expression construct comprising a promoter active in said soybean plants and operably linked thereto a nucleic acid sequence encoding an enzyme capable to metabolize D-alanine or D-serine, and b) a transformation with a second construct said construct comprising a second selection marker gene, which is not conferring resistance against D-alanine or D-serine.

Preferably, said second marker gene is conferring resistance against at least one compound select from the group consisting of phosphinotricin, dicamba, glyphosate, sulfonylurea- and imidazolinone-type herbicides or an antibiotic. Also the products of said method as such are new and inventive over the art. Thus another embodiment of the invention relates to a soybean plant comprising a) a first expression construct comprising a promoter active in said soybean plants and operably linked thereto a nucleic acid sequence encoding an enzyme capable to metabolize D-alanine or D-serine, and b) a second expression construct for a selection marker gene, which is not conferring resistance against D-alanine or D-serine.

Not only different selection marker systems can be combined with the markers provided hereunder. Also the different markers provided herein can be combined (without prior deletion) to achieve subsequently multiple transformations. Accordingly another embodiment of the invention relates to a method for subsequent transformation of at least two DNA constructs into a soybean plant comprising the steps of:

a) a transformation with a first construct said construct comprising an expression construct comprising a promoter active in said soybean plants and operably linked thereto a nucleic acid sequence encoding an dsdA enzyme and selecting with D-serine, and b) a transformation with a second construct said construct comprising an expression construct comprising promoter active in said soybean plants and operably linked thereto a nucleic acid sequence encoding a dao enzyme and selecting with D-alanine.

Also the products of said method are considered to be new and inventive over the art. Thus, another embodiment of the invention relates to a soybean plant comprising a) a first construct said construct comprising an expression construct comprising a promoter active in said soybean plants and operably linked thereto a nucleic acid sequence encoding an dsdA enzyme, and b) a second construct said construct comprising an expression construct comprising promoter active in said soybean plants and operably linked thereto a nucleic acid sequence encoding a dao enzyme.

Other objects, advantages, and features of the present invention will become apparent from the following specification.

A. SHA07/pSB1/ET017; Top: 15 mM, Middle: 30 mM, bottom: 45 mM D-Ser; and

B. SHA07/pSB1/EW008; Top: 15 mM, Middle: 30 mM, bottom: 45 mM D-Ser.

Figure 3:
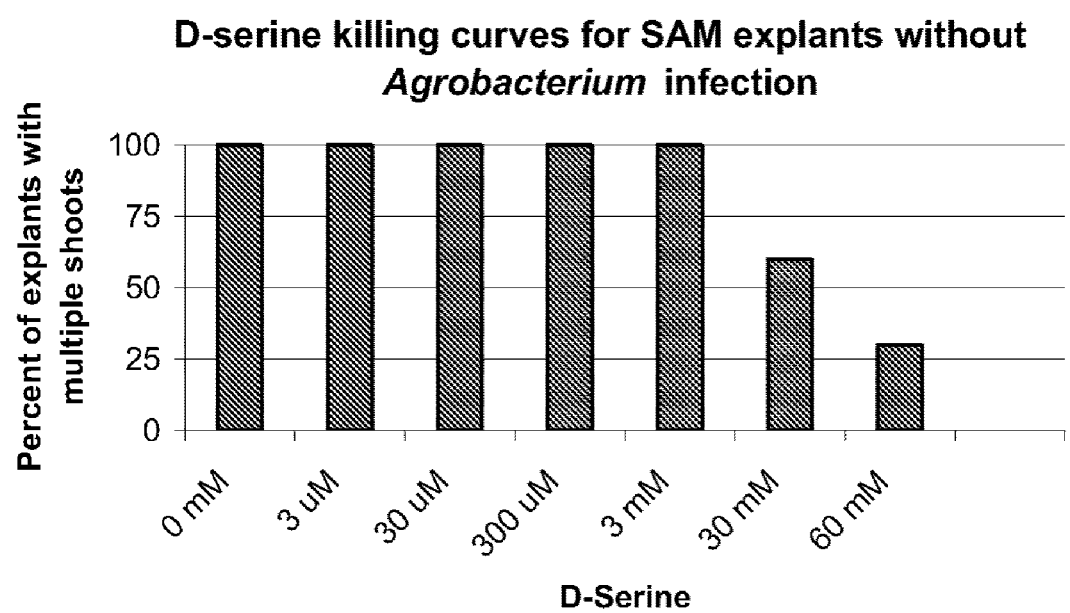

In the specification at page 8, line 37, please replace the paragraph starting with "FIG. 3" with the following amended paragraph:

FIG. 3 Killing curve on non-inoculated seedling axillary meristem explant (cultivar 98822).

GENERAL DEFINITIONS

The teachings, methods, sequences etc. employed and described in the international patent applications WO 03/004659 (RECOMBINATION SYSTEMS AND A METHOD FOR REMOVING NUCLEIC ACID SEQUENCES FROM THE GENOME OF EUKARYOTIC ORGANISMS), WO 03/060133 (SELECTIVE PLANT GROWTH USING D-AMINO ACIDS), international patent application PCT/EP 2005/002735, international patent application PCT/EP 2005/002734 (WO 2005/090581), Application No. 60/606,789, filed Sep. 2, 2004, and international application PCT/EP2005/009366 are hereby incorporated by reference.

Abbreviations: BAP—6-benzylaminopurine; 2,4-D—2,4-dichlorophenoxyacetic acid; MS—Murashige and Skoog medium (Murashige T and Skoog F (1962) Physiol. Plant. 15, 472-497); NAA—1-naphtaleneacetic acid; MES, 2-(N-morpholino-ethanesulfonic acid, IAA indole acetic acid; IBA: indole butyric acid; Kan: Kanamycin sulfate; GA3-Gibberellic acid; Timentin™: ticarcillin disodium/clavulanate potassium.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent, more preferably 5 percent up or down (higher or lower).

As used herein, the word "or" means any one member of a particular list and also includes any combination of members of that list.

"Agronomically valuable trait" includes any phenotype in a plant organism that is useful or advantageous for food production or food products, including plant parts and plant products. Non-food agricultural products such as paper, etc. are also included. A partial list of agronomically valuable traits includes pest resistance, vigor, development time (time to harvest), enhanced nutrient content, novel growth patterns, flavors or colors, salt, heat, drought and cold tolerance, and the like. Preferably, agronomically valuable traits do not include selectable marker genes (e.g., genes encoding herbicide or antibiotic resistance used only to facilitate detection or selection of transformed cells), hormone biosynthesis genes leading to the production of a plant hormone (e.g., auxins, gibberllins, cytokinins, abscisic acid and ethylene that are used only for selection), or reporter genes (e.g. luciferase, glucuronidase, chloramphenicol acetyl transferase (CAT, etc.). Such agronomically valuable important traits may include improvement of pest resistance (e.g., Melchers 2000), vigor, development time (time to harvest), enhanced nutrient content, novel growth patterns, flavors or colors, salt, heat, drought, and cold tolerance (e.g., Sakamoto 2000; Saijo 2000; Yeo 2000; Cushman 2000), and the like. Those of skill will recognize that there are numerous polynucleotides from which to choose to confer these and other agronomically valuable traits.

As used herein, the term "amino acid sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The abbreviations used herein are conventional one letter codes for the amino acids: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid (see L. Stryer, Biochemistry, 1988, W. H. Freeman and Company, New York. The letter "x" as used herein within an amino acid sequence can stand for any amino acid residue.

The term "nucleic acid" refers to deoxyribonucleotides or ribonucleotides and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide".

The phrase "nucleic acid sequence" as used herein refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide".

The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.). A nucleic acid sequence of interest may preferably encode for an agronomically valuable trait.

The term "antisense" is understood to mean a nucleic acid having a sequence complementary to a target sequence, for example a messenger RNA (mRNA) sequence the blocking of whose expression is sought to be initiated by hybridization with the target sequence.

The term "sense" is understood to mean a nucleic acid having a sequence which is homologous or identical to a target sequence, for example a sequence which binds to a protein transcription factor and which is involved in the expression of a given gene. According to a preferred embodiment, the nucleic acid comprises a gene of interest and elements allowing the expression of the said gene of interest.

As used herein, the terms "complementary" or "complementarity" are used in reference to nucleotide sequences related by the base-pairing rules. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. A "complement" of a nucleic acid sequence as used herein refers to a nucleotide sequence whose nucleic acids show total complementarity to the nucleic acids of the nucleic acid sequence.

The term "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

The term "isolated" as used herein means that a material has been removed from its original environment. For example, a naturally-occurring polynucleotide or polypeptide present in a living animal is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid refers to a nucleic acid sequence that is identified and separated from at least one contaminant nucleic acid with which it is ordinarily associated in its natural source.

As used herein, the term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

A "polynucleotide construct" refers to a nucleic acid at least partly created by recombinant methods. The term "DNA construct" is referring to a polynucleotide construct consisting of deoxyribonucleotides. The construct may be single- or—preferably—double stranded. The construct may be circular or linear. The skilled worker is familiar with a variety of ways to obtain one of a DNA construct. Constructs can be prepared by means of customary recombination and cloning techniques as are described, for example, in Maniatis 1989, Silhavy 1984, and in Ausubel 1987.

The term "wild-type", "natural" or of "natural origin" means with respect to an organism, polypeptide, or nucleic acid sequence, that said organism is naturally occurring or available in at least one naturally occurring organism which is not changed, mutated, or otherwise manipulated by man.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

The terms "heterologous nucleic acid sequence" or "heterologous DNA" are used inter-changeably to refer to a nucleotide sequence, which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. A promoter, transcription regulating sequence or other genetic element is considered to be "heterologous" in relation to another sequence (e.g., encoding a marker sequence or am agronomically relevant trait) if said two sequences are not combined or differently operably linked their natural environment. Preferably, said sequences are not operably linked in their natural environment (i.e. come from different genes). Most preferably, said regulatory sequence is covalently joined and adjacent to a nucleic acid to which it is not adjacent in its natural environment.

The term "transgene" as used herein refers to any nucleic acid sequence, which is introduced into the genome of a cell or which has been manipulated by experimental manipulations by man. Preferably, said sequence is resulting in a genome which is different from a naturally occurring organism (e.g., said sequence, if endogenous to said organism, is introduced into a location different from its natural location, or its copy number is increased or decreased). A transgene may be an "endogenous DNA sequence", "an "exogenous DNA sequence" (e.g., a foreign gene), or a "heterologous DNA sequence". The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

The term "transgenic" or "recombinant" when used in reference to a cell or an organism (e.g., with regard to a soybean plant or cell) refers to a cell or organism which contains a transgene, or whose genome has been altered by the introduction of a transgene. A transgenic organism or tissue may comprise one or more transgenic cells. Preferably, the organism or tissue is substantially consisting of transgenic cells (i.e., more than 80%, preferably 90%, more preferably 95%, most preferably 99% of the cells in said organism or tissue are transgenic). The term "recombinant" with respect to nucleic acids means that the nucleic acid is covalently joined and adjacent to a nucleic acid to which it is not adjacent in its natural environment. "Recombinant" polypeptides or proteins refer to polypeptides or proteins produced by recombinant DNA techniques, i.e., produced from cells transformed by an recombinant DNA construct encoding the desired polypeptide or protein. Recombinant nucleic acids and polypeptide may also comprise molecules which as such does not exist in nature but are modified, changed, mutated or otherwise manipulated by man.

A "recombinant polypeptide" is a non-naturally occurring polypeptide that differs in sequence from a naturally occurring polypeptide by at least one amino acid residue. Preferred methods for producing said recombinant polypeptide and/or nucleic acid may comprise directed or non-directed mutagenesis, DNA shuffling or other methods of recursive recombination.

The terms "homology" or "identity" when used in relation to nucleic acids or amino acid sequences refers to a degree of sequence relation ship or complementarity. The following terms are used to describe the sequence relationships between two or more nucleic acids or amino acid sequences: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993. For comparing sequences hereunder, preferably the algorithms BLASTN for nucleotide sequences, BLASTX for proteins with their respective default parameters are used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See website at ncbi.nlm.nih.gov. Alignment may also be performed manually by inspection. Multiple aligments (i.e. of more than 2 sequences) are preferably performed using the Clustal W algorithm (Thompson 1994; e.g., in the software Vector NTI™, version 9; Invitrogen Inc.) with the scoring matrix BLOSUM62MT2 with the default settings (gap opening penalty 15/19, gap extension penalty 6.66/0.05; gap separation penalty range 8; % identity for alignment delay 40; using residue specific gaps and hydrophilic residue gaps). Comparison is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program. Software for performing BLAST analyses is publicly available through the National Center for Biotechnology Information (see website at ncbi.nlm.nih.gov/). In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The term "hybridization" as used herein includes "any process by which a strand of nucleic acid joins with a complementary strand through base pairing." (Coombs 1994). Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids. As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: Tm=81.5+0.41 (% G+C), when a nucleic acid is in aqueous solution at 1 M NaCl [see e.g., Anderson and Young, 1985)]. Other references include more sophisticated computations, which take structural as well as sequence characteristics into account for the calculation of Tm.

An example of highly stringent wash conditions is 0.15 M NaCl at 72° C. for about 15 minutes. An example of stringent wash conditions is a 0.2×SSC wash at 65° C. for 15 minutes (see, Maniatis, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of highly stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 80% to 90% homology to the first nucleic acid sequence, then another hybridization condition is said to be equivalent to the hybridization condition of interest if this other hybridization condition also results in hybridization of the first nucleic acid sequence with the other nucleic acid sequences that have from 80% to 90% homology to the first nucleic acid sequence.

When used in reference to nucleic acid hybridization one skilled in the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above-listed conditions. Those skilled in the art know that whereas higher stringencies may be preferred to reduce or eliminate non-specific binding, lower stringencies may be preferred to detect a larger number of nucleic acid sequences having different homologies.

The term "gene" refers to a coding region operably joined to appropriate regulatory sequences capable of regulating the expression of the polypeptide in some manner. A gene includes untranslated regulatory regions of DNA (e.g., promoters, enhancers, repressors, etc.) preceding (upstream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'side by the nucleotide triplet "ATG" which encodes the initiator methionine and on the 3'-side by one of the three triplets, which specify stop codons (i.e., TAA, TAG, TGA). In addition to containing introns, genomic forms of a gene may also include sequences located on both the 5'- and 3'-end of the sequences, which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers, which control or influence the transcription of the gene. The 3'-flanking region may contain sequences, which direct the termination of transcription, posttranscriptional cleavage and polyadenylation.

The terms "polypeptide", "peptide", "oligopeptide", "gene product", "expression product" and "protein" are used interchangeably herein to refer to a polymer or oligomer of consecutive amino acid residues.

The term "genetically-modified organism" or "GMO" refers to any organism that comprises transgene DNA. Exemplary organisms include plants, animals and microorganisms.

The term "plant" as used herein refers to a plurality of plant cells, which are largely differentiated into a structure that is present at any stage of a plant's development. Such structures include one or more plant organs including, but are not limited to, fruit, shoot, stem, leaf, flower petal, etc.

The term "cell" or "plant cell" as used herein refers to a single cell. The term "cells" refers to a population of cells. The population may be a pure population comprising one cell type. Likewise, the population may comprise more than one cell type. In the present invention, there is no limit on the number of cell types that a cell population may comprise. The cells may be synchronized or not synchronized. A plant cell within the meaning of this invention may be isolated (e.g., in suspension culture) or comprised in a plant tissue, plant organ or plant at any developmental stage.

The term "organ" with respect to a plant (or "plant organ") means parts of a plant and may include (but shall not limited to) for example roots, fruits, shoots, stem, leaves, anthers, sepals, petals, pollen, seeds, etc.

The term "tissue" with respect to a plant (or "plant tissue") means arrangement of multiple plant cells including differentiated and undifferentiated tissues of plants. Plant tissues may constitute part of a plant organ (e.g., the epidermis of a plant leaf) but may also constitute tumor tissues (e.g., callus tissue) and various types of cells in culture (e.g., single cells, protoplasts, embryos, calli, protocorm-like bodies, etc.). Plant tissue may be in planta, in organ culture, tissue culture, or cell culture.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., PCR analysis, Southern blot analysis, fluorescence in situ hybridization (FISH), and in situ PCR.

The term "structural gene" as used herein is intended to mean a DNA sequence that is transcribed into mRNA, which is then translated into a sequence of amino acids characteristic of a specific polypeptide.

The term "expression" refers to the biosynthesis of a gene product. For example, in the case of a structural gene, expression involves transcription of the structural gene into mRNA and—optionally—the subsequent translation of mRNA into one or more polypeptides.

The term "expression cassette" or "expression construct" as used herein is intended to mean the combination of any nucleic acid sequence to be expressed in operable linkage with a promoter sequence and—optionally—additional elements (like e.g., terminator and/or polyadenylation sequences) which facilitate expression of said nucleic acid sequence.

"Promoter", "promoter element," or "promoter sequence" as used herein, refers to the nucleotide sequences at the 5' end of a nucleotide sequence which direct the initiation of transcription (i.e., is capable of controlling the transcription of the nucleotide sequence into mRNA). A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. Promoter sequences are necessary, but not always sufficient, to drive the expression of a downstream gene. In general, eukaryotic promoters include a characteristic DNA sequence homologous to the consensus 5'-TATAAT-3' (TATA) box about 10-30 bp 5' to the transcription start (cap) site, which, by convention, is numbered +1. Bases 3' to the cap site are given positive numbers, whereas bases 5' to the cap site receive negative numbers, reflecting their distance from the cap site. Another promoter component, the CAAT box, is often found about 30 to 70 bp 5' to the TATA box and has homology to the canonical form 5'-CCAAT-3' (Breathnach 1981). In plants the CAAT box is sometimes replaced by a sequence known as the AGGA box, a region having adenine residues symmetrically flanking the triplet G(or T)NG (Messing 1983). Other sequences conferring regulatory influences on transcription can be found within the promoter region and extending as far as 1000 bp or more 5' from the cap site. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

Regulatory Control refers to the modulation of gene expression induced by DNA sequence elements located primarily, but not exclusively, upstream of (5' to) the transcription start site. Regulation may result in an all-or-nothing response to environmental stimuli, or it may result in variations in the level of gene expression. In this invention, the heat shock regulatory elements function to enhance transiently the level of downstream gene expression in response to sudden temperature elevation.

Polyadenylation signal refers to any nucleic acid sequence capable of effecting mRNA processing, usually characterized by the addition of polyadenylic acid tracts to the 3'-ends of the mRNA precursors. The polyadenylation signal DNA segment may itself be a composite of segments derived from several sources, naturally occurring or synthetic, and may be from a genomic DNA or an RNA-derived cDNA. Polyadenylation signals are commonly recognized by the presence of homology to the canonical form 5'-AATAA-3', although variation of distance, partial "readthrough", and multiple tandem canonical sequences are not uncommon (Messing 1983). It should be recognized that a canonical "polyadenylation signal" may in fact cause transcriptional termination and not polyadenylation per se (Montell 1983).

Heat shock elements refer to DNA sequences that regulate gene expression in response to the stress of sudden temperature elevations. The response is seen as an immediate albeit transitory enhancement in level of expression of a downstream gene. The original work on heat shock genes was done with *Drosophila* but many other species including plants (Barnett 1980) exhibited analogous responses to stress. The essential primary component of the heat shock element was described in *Drosophila* to have the consensus sequence 5'-CTGGAATNTTCTAGA-3' (where N=A, T, C, or G) and to be located in the region between residues −66 through −47 bp upstream to the transcriptional start site (Pelham 1982). A chemically synthesized oligonucleotide copy of this consensus sequence can replace the natural sequence in conferring heat shock inducibility.

Leader sequence refers to a DNA sequence comprising about 100 nucleotides located between the transcription start site and the translation start site. Embodied within the leader sequence is a region that specifies the ribosome binding site.

Introns or intervening sequences refer in this work to those regions of DNA sequence that are transcribed along with the coding sequences (exons) but are then removed in the formation of the mature mRNA. Introns may occur anywhere within a transcribed sequence—between coding sequences of the same or different genes, within the coding sequence of a gene, interrupting and splitting its amino acid sequences, and within the promoter region (5' to the translation start site). Introns in the primary transcript are excised and the coding sequences are simultaneously and precisely ligated to form the mature mRNA. The junctions of introns and exons form the splice sites. The base sequence of an intron begins with GU and ends with AG. The same splicing signal is found in many higher eukaryotes.

The term "operable linkage" or "operably linked" is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions, which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. Operable linkage, and an expression cassette, can be generated by means of customary recombination and cloning techniques as described (e.g., in Maniatis 1989; Silhavy 1984; Ausubel 1987; Gelvin 1990). However, further sequences, which—for example—act as a linker with specific cleavage sites for restriction enzymes, or as a signal peptide, may also be positioned between the two sequences. The insertion of sequences may also lead to the expression of fusion proteins. Preferably, the expression cassette, consisting of a linkage of promoter and nucleic acid sequence to be expressed, can exist in a vector-integrated form and be inserted into a plant genome, for example by transformation.

The term "transformation" as used herein refers to the introduction of genetic material (e.g., a transgene) into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., β-glucuronidase) encoded by the transgene (e.g., the uid Agene) as demonstrated herein [e.g., histochemical assay of GUS enzyme activity by staining with X-gluc which gives a blue precipitate in the presence of the GUS enzyme; and a chemiluminescent assay of GUS enzyme activity using the GUS-Light kit (Tropix)]. The term "transient transformant" refers to a cell which has transiently incorporated one or more transgenes. In contrast, the term "stable transformation" or "stably transformed" refers to the introduction and integration of one or more transgenes into the genome of a cell, preferably resulting in chromosomal integration and stable heritability through meiosis. Stable transformation of a cell may be detected by Southern blot hybridization of genomic DNA of the cell with nucleic acid sequences, which are capable of binding to one or more of the transgenes. Alternatively, stable transformation of a cell may also be detected by the polymerase chain reaction of genomic DNA of the cell to amplify transgene sequences. The term "stable transformant" refers to a cell, which has stably integrated one or more transgenes into the genomic DNA (including the DNA of the plastids and the nucleus), preferably integration into the chromosomal DNA of the nucleus. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformation also includes introduction of genetic material into plant cells in the form of plant viral vectors involving epichromosomal replication and gene expression, which may exhibit variable properties with respect to meiotic stability. Preferably, the term "transformation" includes introduction of genetic material into plant cells resulting in chromosomal integration and stable heritability through meiosis.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium, which causes crown gall. The term "*Agrobacterium*" includes, but is not limited to, the strains *Agrobacterium tumefaciens*, (which typically causes crown gall in infected plants), and *Agrobacterium rhizogenes* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208) are referred to as "nopaline-type" Agrobacteria; *Agrobacterium* strains which cause production of octopine (e.g., strain LBA4404, Ach5, B6) are referred to as "octopine-type" Agrobacteria; and *Agrobacterium* strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle bombardment as described herein.

The "efficiency of transformation" or "frequency of transformation" as used herein can be measured by the number of transformed cells (or transgenic organisms grown from individual transformed cells) that are recovered under standard experimental conditions (i.e. standardized or normalized with respect to amount of cells contacted with foreign DNA, amount of delivered DNA, type and conditions of DNA delivery, general culture conditions etc.) For example, when isolated explants of axillary meristematic tissue are used as starting material for transformation, the frequency of transformation can be expressed as the number of transgenic plant lines obtained per 100 isolated explants transformed.

The terms "meristem" or "meristematic cells" or meristematic tissue" can be used interchangeable and are intended to mean undifferentiated plant tissue, which continually divides, forming new cells, as that found at the tip of a stem or root. The term "node" or "leaf node" is intended to mean the point on a stem where a leaf is attached or has been attached. The term "internode" is intended to mean the section or part between two nodes on a stem. The term "petiole" is intended to mean the stalk by which a leaf is attached to a stem, also called a leaf-stalk. The term "axillary bud" is intended to mean a small protuberance along a stem or branch, sometimes enclosed in protective scales and containing an undeveloped shoot, leaf, or flower; also called a lateral bud. The term "hypocotyl" is intended to mean the part of the stem between the seed leaves (the cotyledons) and the root. The term "leaf axil" is intended to mean the angle between a leaf and the stem on which it is borne. The axillary bud occurs at the leaf axil. The term "cotyledon" is intended o man a leaf of the embryo of a seed plant, which upon germination either remains in the seed or emerges, enlarges, and becomes green; also called a seed leaf. The embryo axis is located between the cotyledons and is attached to them near the end closest to the micropyle.

The term "dedifferentiation", "dedifferentiation treatment" or "dedifferentiation pretreatment" means a process of obtaining cell clusters, such as callus, that show unorganized growth by culturing differentiated cells of plant tissues on a dedifferentiation medium. More specifically, the term "dedifferentiation" as used herein is intended to mean the process of formation of rapidly dividing cells without particular function in the scope of the plant body. These cells often possess an increased potency with regard to its ability to develop into various plant tissues. Preferably the term is intended to mean the reversion of a differentiated or specialized tissues to a more pluripotent or totipotent (e.g., embryonic) form. Dedifferentiation may lead to reprogramming of a plant tissue (revert first to undifferentiated, non-specialized cells. then to new and different paths). The term "totipotency" as used herein is intended to mean a plant cell containing all the genetic and/or cellular information required to form an entire plant. Dedifferentiation can be initiated by certain plant growth regulators (e.g., auxin and/or cytokinin compounds), especially by certain combinations and/or concentrations thereof.

DETAILED DESCRIPTION OF THE INVENTION

The present invention is a method for the direct germline genetic transformation of varieties of soybean, *Glycine max*, based on a D-amino acid selection system. A first embodiment of the invention relates to a method for generating a transgenic soybean plant comprising the steps of a. introducing into a soybean cell or tissue a DNA construct comprising at least one first expression construct comprising a promoter active in said soybean plant and operably linked thereto a nucleic acid sequence encoding an enzyme capable to metabolize D-alanine and/or D-serine, and b. incubating said soybean cell or tissue of step a) on a selection medium comprising D-alanine and/or D-serine and/or a derivative thereof in a total concentration from about 3 mM to about 100 mM for a time period of at least 5 days, and c. transferring said soybean cell or tissue of step b) to a regeneration medium and regenerating and selecting soybean plants comprising said DNA construct.

The selection pressure applied after co-cultivation comprises in one embodiment one or more of the following steps:
   a. first without selection on shoot induction;
   b. selecting during on shoot induction,
   c. selecting throughout shoot elongation.

Preferably the D-ala concentration is 40 mM or below, more preferred 30 mM or below if added to the medium, e.g. to a medium like the SIM medium. Further, the concentration is in one embodiment around 2 mM, 3 mM, or 5 mM or more, more preferred are around 10 mM. Thus, in one embodiment, the concentration is between 7.5 and 20 mM D-ala in the medium for selection. In combination with concentration of below 10 mM D-serine the D-ala concentration is preferably 30 mM or below, even more preferred are 20 mM or lower. The person in the art knows, starting from this data, how to adapt the D-ala or the D-ala and D-ser concentrations to specific conditions of each individual selection scheme, e.g. the concentrations may vary if another medium, another age of the shoots, another incubation time or another construct etc. is used. For example, a higher expression rate or activity of the enzymes, e.g. due to the use of a stronger promoter, allows higher concentrations of D-ala and/or D-ser to be used. Thus, in one embodiment the selection should is around between 5 and 20 mM D-Ala, e.g. 10 to 15 mM in shoot induction combined with 1 to 10 mM, preferably below 7.5 mM, more preferred between 2 and 5 mM D-Ala, e.g. around 3 mM D-Ala in shoot elongation. Thus, in one embodiment the selection should is around between 5 and 20 mM D-Ser, e.g. 10 to 15 mM in shoot induction combined with 1 to 10 mM, preferably below 7.5 mM, more preferred between 2 and 5 mM D-Ser, e.g. around 3 mM D-Ser in shoot elongation. Thus, in one embodiment the selection should is around between 5 and 20 mM D-Ser and D-Ala, e.g. 10 to 15 mM in shoot induction combined with 1 to 10 mM, preferably below 7.5 mM, more preferred between 2 and 5 mM D-Ser and D-Ala, e.g. around 3 mM D-Ser and D-Ala in shoot elongation. For example, the selection is done i) using about 3 to about 30 mM D-alanine;
ii) using about 30 to 50 mM D-serine, and/or
iii) using about 1 to 10 mM D-serine in combination with 30 mM D-alanine or less, preferably around 5 to 7 mM D-serine, e.g. 7.5 mM and 10 mM to 20 mM D-alanine for about 3 to 4 weeks under dedifferentiating conditions. Accordingly, in one embodiment, the selection after transformation with a dsda gene comprises the following steps:

a. 5 to 10 days, e.g. 7 days on shoot induction without selection,
b. 2 to 4 weeks, e.g. 3 weeks on shoot induction medium with 5 mM to 10 mM, e.g. 7.5 mM D-serine;
c. 2 mM to 7 mM, e.g. 5 mM D-serine throughout shoot elongation.

Accordingly, in an other embodiment, the selection after transformation with a dao1 gene comprises the following steps:

a. 5 to 10 days, e.g. 6 to 7 days on shoot induction without selection,
b. 2 to 4 weeks, e.g. 3 weeks on shoot induction medium with 5 mM to 10 mM, e.g. 7.5 mM D-alanine;
c. 2 mM to 7 mM, e.g. 5 mM D-alanine throughout shoot elongation.

Further, the selection after transformation with a dao1 gene comprises for example the following steps:

a. 5 to 10 days, e.g. 5 to 7 days on shoot induction without selection,
b. 2 to 4 weeks, e.g. 3 weeks on shoot induction medium with 5 mM to 10 mM, e.g. 7.5 mM D-alanine and with 5 mM to 10 mM, e.g. 7.5 mM D-serine;
c. 2 mM to 7 mM, e.g. 5 mM D-serine and 2 mM to 7 mM, e.g. 5 mM D-alanine throughout shoot elongation.

In one embodiment, the method of the present invention comprises one or more, e.g. all, of the following steps:

a. Sterilization of the seedlings;
b. Growing the seedlings for 3 to 10 d, preferably for 5 to 8 d, e.g. for 7 d at light;
c. Growing the epicotyl with the unifoliate leaves to the length of the cotyledons or longer;
d. Growing the epicotyl to between 0.5 cm and 4 cm; e.g. 0.7 cm or more, 1.0 cm or more, or 2 cm or less.
e. Removing all preformed leaves including apical meristem
f. Injuring the node located at the first set of leaves with several cuts
g. Co-cultivating wounded node with *Agrobacterium* mixture for 0.1 h to 1 h, e.g. 0.5 h in liquid medium.
h. Co-cultivating node with *Agrobacterium* for 3 to 5 days in the dark on solid co-cultivation medium;
i. Placing the explants for selection under a 18 h light/6 h dark cycle at 70 to 100 microE/m$^2$ s till de axillary merstems growth at the first node above the epicotyl;
j. Removing shoots formed before transformation up to 2 weeks after co-cultivation and optionally cutting during this time the explant into smaller pieces;
k. Transferring the explants to shoot primordia elongation medium after 2 to 4 weeks after co-cultivation and transferring the explants every 2 to 3 weeks to fresh medium with selection agent after removing dead tissue till shoots elongate;
l. Removing shoots 3 cm or larger from the explant and place into root inducing medium for a week till roots begin to form;
m. Transferring rooted shoots to soil and hardened in a growth chamber for 2 to 3 weeks before transferring the rooted shoots to greenhouse.

Accordingly, the method of the invention using dsdA gene comprises in one preferred step the use of Shoot axillary meristems from *Glycine max* as explant for transformation. In particular, an *A. rhizogenes* SHA017 or a *A. tumefaciens* strain can be used for transformation, preferred is the use of *A. rhizogenes* SHA017, e.g. the strain K599 as described below. In one embodiment, the infection takes place for around 30 min, e.g. between 25 and 35 min at room temperature, e.g. between 18° C. and below 25° C., preferably between 20° C. and 23° C. The OD can be in one embodiment around 1.5. Further, the Co-cultivation takes place preferably for around 5 days, e.g. between 3 and 8 days, more preferred 4 or 5 days, preferably in the dark, e.g. 23° C. to 27° C., preferably 24° C. to 25° C. The recovery of the transformed explants takes in one embodiment around 5 to around 8 days, e.g. 6 or 7 days, preferably at light, e.g. at around 25° C. or 23° C. to 27° C., preferably 24° C. to 26° C. As described already above and further described below the selection during shoot/callus initiation can be at a concentration of for example 3 mM to 10 mM D-ser, preferably at around 7.5 mM D-ser or at other suitable concentrations and compositions described herein for around 3 weeks, e.g. for 15 to 24 days, preferably for 20 to 22 days, preferably at light and e.g. at around 25° C. or 23° C. to 26° C., preferably 24° C. to 25°. Furthermore, the step of selection during shoot elongation/callus regeneration can take place at a concentration of for example 3 mM to 10 mM D-ser, preferably at around 5 mM D-ser or at other suitable concentrations and compositions described herein for around 4 to 5 weeks, e.g. for 25 to 35 days, preferably for around 30 days, preferably at light and e.g. at around 25° C. or 23° C. to 26° C., preferably 24° C. to 25°. The rooting step can take place without or very little amount of selection, for example at around 0 mM D-ser for around 1 to 2 weeks, e.g. for 5 to 10 days, preferably at light and e.g. at 23° C. to 27° C., preferably 24° C. to 25°.

1. The DNA Construct of the Invention 1.1 The First Expression Construct of the Invention The first expression construct comprises a promoter active in soybeans and operably linked thereto a nucleic acid sequence encoding an enzyme capable to metabolize D-alanine and/or D-serine. Preferably said promoter is heterologous in relation to said enzyme encoding sequence. The promoter active in soybean plants and the D-alanine and/or D-serine metabolizing enzyme are defined below in detail.

1.1.1 The Enzyme Capable to Metabolize D-Alanine or D-Serine

The person skilled in the art is aware of numerous sequences suitable to metabolize D-alanine and/or D-serine.

The term "enzyme capable to metabolize D-alanine or D-serine" means preferably an enzyme, which converts and/or metabolizes D-alanine and/or D-serine with an activity that is at least two times (at least 100% higher), preferably at least three times, more preferably at least five times, even more preferably at least 10 times, most preferably at least 50 times or 100 times the activity for the conversion of the corresponding L-amino acid (i.e., D-alanine and/or D-serine) and—more preferably—also of any other D- and/or L- or achiral amino acid.

Preferably, the enzyme capable to metabolize D-alanine or D-serine is selected from the group consisting of D-serine ammonia-lyase (D-Serine dehydratases; EC 4.3.1.18; formerly EC 4. 2.1.14), D-Amino acid oxidases (EC 1.4.3.3), and D-Alanine transami-nases (EC 2.6.1.21). More preferably, the enzyme capable to metabolize D-alanine or D-serine is selected from the group consisting of D-serine ammonia-lyase (D-Serine dehydratases; EC 4.3.1.18; formerly EC 4. 2.1.14), and D-Amino acid oxidases (EC 1.4.3.3). The term "D-serine ammonia-lyase" (D-Serine dehydratases; EC 4.3.1.18; formerly EC 4. 2.1.14) means enzymes catalyzing the conversion of D-serine to pyruvate and ammonia. The reaction catalyzed probably involves initial elimination of water (hence the enzyme's original classification as EC 4.2.1.14), followed by isomerization and hydrolysis of the product with C—N bond breakage. For examples of suitable enzyme see website at expasy.org/enzyme/4.3.1.18. The term "D-Alanine transami-nases" (EC 2.6.1.21) means enzymes catalyzing the reaction of D-Alanine with 2-oxoglutarate to pyruvate and D-glutamate. D-glutamate is much less toxic to plants than D-Alanine See website at expasy.org/enzyme/2.6.1.21.

The term D-amino acid oxidase (EC 1.4.3.3; abbreviated DAAO, DAMOX, or DAO) is referring to the enzyme converting a D-amino acid into a 2-oxo acid, by—preferably—employing Oxygen (O2) as a substrate and producing hydrogen peroxide (H2O2) as a co-product (Dixon 1965a,b,c; Massey 1961; Meister 1963). DAAO can be described by the Nomenclature Committee of the International Union of Biochemistry and Molecular Biology (IUBMB) with the EC (Enzyme Commission) number EC 1.4.3.3. Generally a DAAO enzyme of the EC 1.4.3.3. class is an FAD flavoenzyme that catalyzes the oxidation of neutral and basic D-amino acids into their corresponding keto acids. DAAOs have been characterized and sequenced in fungi and vertebrates where they are known to be located in the peroxisomes. In DAAO, a conserved histidine has been shown (Miyano 1991) to be important for the enzyme's catalytic activity. In a preferred embodiment of the invention a DAAO is referring to a protein comprising the following consensus motif: [LIVM]-[LIVM]-H*-[NHA]-Y-G-x-[GSA]-[GSA]-x-G-x5-G-x-A (SEQ ID NO: 18), wherein amino acid residues given in brackets represent alternative residues for the respective position, x represents any amino acid residue, and indices numbers indicate the respective number of consecutive amino acid residues. The abbreviation for the individual amino acid residues have their standard IUPAC meaning as defined above. D-Amino acid oxidase (EC-number 1.4.3.3) can be isolated from various organisms, including but not limited to pig, human, rat, yeast, bacteria or fungi. Example organisms are *Candida tropicalis, Trigonopsis variabilis, Neurospora crassa, Chlorella vulgaris*, and *Rhodotorula gracilis*. A suitable D-amino acid metabolising polypeptide may be an eukaryotic enzyme, for example from a yeast (e.g. *Rhodotorula gracilis*), fungus, or animal or it may be a prokaryotic enzyme, for example, from a bacterium such as *Escherichia coli*. For examples of suitable enzyme see website at expasy.org/enzyme/1.4.3.3.

Examples of suitable polypeptides, which metabolise D-amino acids are shown in Table 1. The nucleic acid sequences encoding said enzymes are available form databases (e.g., under Genbank Acc.-No. U60066, A56901, AF003339, Z71657, AF003340, U63139, D00809, Z50019, NC_003421, AL939129, AB042032). As demonstrated above, DAAO from several different species have been characterized and shown to differ slightly in substrate affinities (Gabler 2000), but in general they display broad substrate specificity, oxidatively deaminating all D-amino acids.

TABLE 1

Enzymes suitable for metabolizing D-serine and/or D-alanine. Especially preferred enzymes are presented in bold letters

| Enzyme | EC number | Example | Source organism | Substrate |
|---|---|---|---|---|
| D-Serine dehydratase (D-Serine ammonia lyase, D-Serine deaminiase) | EC 4.3.1.18 (originally EC 4.2.1.14) | P54555 | *Bacillus subtilis* | D-Ser |
| | | P00926 | *Escherichia coli.* | D-Thr |
| | | Q9KL72 | *Vibrio cholera.* VCA0875 | D-allothreonine |
| | | Q9KC12 | *Bacillus halodurans.* | |
| D-Amino acid oxidase | EC 1.4.3.3 | JX0152 | *Fusarium solani* | Most D-amino acid |
| | | O01739 | *Caenorhabditis elegans.* | |
| | | O33145 | *Mycobacterium leprae.* AAO. | |
| | | O35078 | *Rattus norvegicus* (Rat) | |
| | | O45307 | *Caenorhabditis elegans* | |
| | | P00371 | *Sus scrofa* (Pig) | |
| | | P14920 | *Homo sapiens* (Human) | |
| | | P14920 | *Homo sapiens* (Human) | |
| | | P18894 | *Mus musculus* (Mouse) | |
| | | P22942 | *Oryctolagus cuniculus* (Rabbit) | |
| | | P24552 | *Fusarium solani* (subsp. pisi) (*Nectria haematococca*) | |
| | | P80324 | *Rhodosporidium toruloides* (Yeast) (*Rhodotorula gracilis*) | |
| | | Q19564 | *Caenorhabditis elegans* | |
| | | Q28382 | *Sus scrofa* (pig) | |
| | | Q7SFW4 | *Neurospora crassa* | |
| | | Q7Z312 | *Homo sapiens* (Human) | |
| | | Q82MI8 | *Streptomyces avermitilis* | |
| | | Q8P4M9 | *Xanthomonas campestris* | |
| | | Q8PG95 | *Xanthomonas axonopodis* | |

TABLE 1-continued

Enzymes suitable for metabolizing D-serine and/or D-alanine. Especially preferred enzymes are presented in bold letters

| Enzyme | EC number | Example | Source organism | Substrate |
|---|---|---|---|---|
| | | Q8R2R2 | *Mus musculus* (Mouse) | |
| | | Q8SZN5 | *Drosophila melanogaster* | |
| | | Q8VCW7 | *Mus musculus* (Mouse) | |
| | | Q921M5 | *Cavia parcellus* (Guinea pig) | |
| | | Q95XG9 | *Caenorhabditis elegans* | |
| | | Q99042 | *Trigonopsis variabilis* | |
| | | Q9C1L2 | *Neurospora crassa* | |
| | | Q9JXF8 | *Neisseria meningitidis* (serogroup B) NMB2068 | |
| | | Q9V5P1 | *Drosophila melanogaster* | |
| | | Q9VM80 | *Drosophila melanogaster* | |
| | | Q9X7P6 | *Streptomyces coelicolor* | |
| | | Q9Y7N4 | *Schizosaccharomyces pombe* (Fission yeast) SPCC1450 | |
| | | Q9Z1M5 | *Cavia porcellus* (Guinea pig) | |
| | | Q9Z302 | *Cricetulus griseus* | |
| | | U60066 | Rhodosporidium toruloides, (Rhodotorula gracilis) strain TCC 26217 | |
| D-Alanine transaminase | 2.6.1.21 | P54692 | *Bacillus licheniformis* | D-Ala |
| | | P54693 | *Bacillus sphaericus* | D-Arg |
| | | P19938 | *Bacillus* sp. (strain YM-1) | D-Asp |
| | | O07597 | *Bacillus subtilis* | D-Glu |
| | | O85046 | *Listeria monocytogenes* | D-Leu |
| | | P54694 | *Staphylococcus haemolyticus* | D-Lys |
| | | | | D-Met |
| | | | | D-Phe |
| | | | | D-Norvaline |

Especially preferred in this context are the dao1 gene (EC: 1.4.3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3.1.18; GenBank Acc.-No.: J01603). The dao1 gene is of special advantage since it can be employed as a dual function marker (see international patent application PCT/EP 2005/002734; WO 2005/090581).

Suitable D-amino acid metabolizing enzymes also include fragments, mutants, derivatives, variants and alleles of the polypeptides exemplified above. Suitable fragments, mutants, derivatives, variants and alleles are those, which retain the functional characteristics of the D-amino acid metabolizing enzyme as defined above. Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included.

More preferably for the method of the invention, the enzyme capable to metabolize D-serine is selected from the group consisting of
i) the *E. coli* D-serine ammonia-lyase as encoded by SEQ ID NO: 2, and
ii) enzymes having the same enzymatic activity and an identity of at least 60% (preferably 70% or 75%, more preferably 80% or 85%, even more preferably 90% or 95%, most preferably 98%) to the sequence as encoded by SEQ ID NO: 2, and
iii) enzymes encoded by a nucleic acid sequence capable to hybridize (preferably under conditions equivalent or equal to hybridization with a buffer solution of 30 to (preferably) 35% formamide, 1 M NaCl, 1% SDS at 37° C., and a wash in 1× to 2×SSC (preferably 1×SSC) at 50 to (preferably) 55° C.), more preferably in 40 to (preferably) 45% formamide, 1.0 M NaCl, 1% SDS at 37° C., and a wash in 0.5× to 1×SSC (preferably 0.5×SSC) at 55 to (preferably) 60° C.), and most preferably in 50% formamide, 1 M NaCl, 1% SDS at 37° C., and a wash in 0.1×SSC at 60 to (preferably) 65° C.) to the complement of the sequence described by SEQ ID NO: 1, and wherein selection is done on a medium comprising D-serine in a concentration from about 0.5 mM to about 100 mM, preferably about 1 mM to about 70 mM, more preferably about 2 mM to about 50 mM, most preferably about 3 mM to about 15 mM. The total selection time under dedifferentiating conditions is preferably from about 1 to 10 weeks, preferably from 2 to 8 weeks, more preferably from 3 to 4 weeks.

Accordingly, in one embodiment, in the method of the present invention the enzyme capable to metabolize D-serine is selected from the group consisting of
i) the D-serine ammonia-lyase as shown in Table 1,
ii) enzymes having the same enzymatic activity and an identity of at least 80% (preferably at least 85%, more preferably at least 90%, even more preferably at least 95%, most preferably at least 98%) to an amino acid sequence of a D-serine ammonia-lyase as shown in Table I;
iii) enzymes having the same enzymatic activity and an identity of the encoding nucleic acid sequence of at least 80% (preferably at least 85%, more preferably at least 90%, even more preferably at least 95%, most preferably at least 98%) to a nucleic acid sequence of a D-serine ammonia-lyase as shown in Table 1, and
iv) enzymes encoded by a nucleic acid sequence capable to hybridize to the complement of the sequence encoding the D-serine ammonia-lyase as shown in Table 1, and wherein selection is done on a medium comprising D-serine in a concentration from 3 mM to 100 mM; preferably 4 to 10 mM;

or wherein the enzyme capable to metabolize D-serine and D-alanine is selected from the group consisting of
  i) the D-amino acid oxidase as shown in Table 1, and
  ii) enzymes having the same enzymatic activity and an identity of at least 80% (preferably at least 85%, more preferably at least 90%, even more preferably at least 95%, most preferably at least 98%) to an amino acid sequence of a D-amino acid oxidase as shown in Table 1;
  iii) enzymes having the same enzymatic activity and an identity of the encoding nucleic acid sequence of at least 80% (preferably at least 85%, more preferably at least 90%, even more preferably at least 95%, most preferably at least 98%) to a nucleic acid sequence of a D-amino acid oxidase as shown in Table 1, and
  iv) enzymes encoded by a nucleic acid sequence capable to hybridize to the complement of the sequence encoding the D-amino acid oxidase as shown in Table 1, and wherein selection is done on a medium comprising D-alanine and/or D-serine in a total concentration from 3 mM to 100 mM; preferably 4 to 10 mM "Same activity" in the context of a D-serine ammonialyase means the capability to metabolize D-serine, preferably as the most preferred substrate. Metabolization means the lyase reaction specified above.

Also more preferably for the method of the invention, the enzyme capable to metabolize D-serine and D-alanine is selected from the group consisting of i) the *Rhodotorula gracilis* D-amino acid oxidase as encoded by SEQ ID NO: 4 or 6, and
ii) enzymes having the same enzymatic activity and an identity of at least 60% (preferably 70% or 75%, more preferably 80% or 85%, even more preferably 90% or 95%, most preferably 98%) to the sequence as encoded by SEQ ID NO: 4 or 6, and
iii) enzymes encoded by a nucleic acid sequence capable to hybridize (preferably under conditions equivalent or equal to hybridization with a buffer solution of 30 to (preferably) 35% formamide, 1 M NaCl, 1% SDS at 37° C., and a wash in 1× to 2×SSC (preferably 1×SSC) at 50 to (preferably) 55° C.), more preferably in 40 to (preferably) 45% formamide, 1.0 M NaCl, 1% SDS at 37° C., and a wash in 0.5× to 1×SSC (preferably 0.5×SSC) at 55 to (preferably) 60° C.), and most preferably in 50% formamide, 1 M NaCl, 1% SDS at 37° C., and a wash in 0.1×SSC at 60 to (preferably) 65° C.) to the complement of the sequence described by SEQ ID NO: 3 or 5, and wherein selection is done on a medium comprising D-alanine and/or D-serine in a total concentration from about 0.5 mM to about 100 mM, preferably about 1 mM to about 70 mM, more preferably about 2 mM to about 50 mM, most preferably about 3 mM to about 15 mM. Preferably, D-alanine (e.g., if employed as only selection compound) is employed in a concentration of about 0.5 mM to about 100 mM, preferably about 1 mM to about 70 mM, more preferably about 2 mM to about 50 mM, most preferably about 3 mM to about 20 mM. Preferably, D-serine (e.g., if employed as only selection compound) is employed in a concentration of about 0.5 mM to about 100 mM, preferably about 1 mM to about 70 mM, more preferably about 2 mM to about 50 mM, most preferably about 3 mM to about 15 mM. The total selection time under dedifferentiating conditions is preferably from about 1 to 10 weeks, preferably from 2 to 8 weeks, more preferably from 3 to 4 weeks.

"Same activity" in the context of a D-amino acid oxidase means the capability to metabolize a broad spectrum of D-amino acids (preferably at least D-serine and/or D-alanine). Metabolization means the oxidase reaction specified above.

Mutants and derivatives of the specified sequences can also comprise enzymes, which are improved in one or more characteristics (Ki, substrate specificity etc.) but still comprise the metabolizing activity regarding D-serine and or D-alanine. Such sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Polynucleotides encoding a candidate enzyme can, for example, be modulated with DNA shuffling protocols. DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA. DNA shuffling can be based on a process of recursive recombination and mutation, performed by random fragmentation of a pool of related genes, followed by reassembly of the fragments by a polymerase chain reaction-like process. See, e.g., Stemmer 1994 a,b; Crameri 1997; Moore 1997; Zhang 1997; Crameri 1998; U.S. Pat. No. 5,605,793, U.S. Pat. No. 5,837,458, U.S. Pat. No. 5,830,721 and U.S. Pat. No. 5,811,238. The resulting dsdA- or dao-like enzyme encoded by the shuffled DNA may possess different amino acid sequences from the original version of enzyme. Exemplary ranges for sequence identity are specified above.

The D-amino acid metabolizing enzyme of the invention may be expressed in the cytosol, peroxisome, or other intracellular compartment of the plant cell. Compartmentalisation of the D-amino acid metabolizing enzyme may be achieved by fusing the nucleic acid sequence encoding the DAAO polypeptide to a sequence encoding a transit peptide to generate a fusion protein. Gene products expressed without such transit peptides generally accumulate in the cytosol.

1.1.2 Promoters for Soybean Plants 1.1.2.1 General Promoter

The term "promoter" as used herein is intended to mean a DNA sequence that directs the transcription of a DNA sequence (e.g., a structural gene). Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem.

The term "promoter active in soybean plants" means any promoter, whether plant derived or not, which is capable to induce transcription of an operably linked nucleotide sequence in at least one soybean cell, tissue, organ or plant at least one time point in development or under dedifferentiated conditions. Such promoter may be a non-plant promoter (e.g., derived from a plant virus or *Agrobacterium*) or a plant promoter, preferably a dicotyledonous plant promoter. The person skilled in the art is aware of several promoters which, might be suitable for use in soybean plants. In this context, expression can be, for example, constitutive, inducible or development-dependent. The following promoters are preferred:

a) Constitutive Promoters

"Constitutive" promoters refers to those promoters which ensure expression in a large number of, preferably all, tissues over a substantial period of plant development, preferably at all times during plant development. Examples include the CaMV (cauliflower mosaic virus) 35S promoter (Franck 1980; Shewmaker 1985; Gardner 1986; Odell 1985), the 19S CaMV promoter (U.S. Pat. No. 5,352,605; WO 84/02913; Benfey 1989), the Rubisco small subunit (SSU) promoter (U.S. Pat. No. 4,962,028), the legumin B promoter (GenBank Acc. No. X03677), the promoter of the nopaline synthase from *Agrobacterium*, the TR dual promoter, the OCS (octopine synthase) promoter from *Agrobacterium*, the cinnamyl alcohol dehydrogenase promoter (U.S. Pat. No. 5,683,439), the promoters of the vacuolar ATPase subunits, the pEMU promoter (Last 1991); the MAS promoter (Velten 1984), the promoter of the *Arabidopsis thaliana* nitrilase-1 gene (GenBank Acc. No.: U38846, nucleotides 3862 to 5325 or else 5342), and further promoters of genes with constitutive expression in plants.

Other suitable constitutive promoters are actin promoters. Sequences for several actin promoters from dicotyledonous plants are available by the genomic sequences disclosed in Genbank (for example: AY063089 (*Arabidopsis thaliana* Actin8 gene); AY096381 (*Arabidopsis thaliana* Actin 2 gene; AY305730: (*Gossypium hirsutum* Actin 8 gene); AY305724 (*Gossypium hirsutum* Actin 2 gene); AF111812 (*Brassica napus* Actin gene)). Use of their promoters in heterologous expression is described for the Banana actin promoter (US20050102711). An et al. [Plant J 1996 10(1):107-121] reported that Act2 and Act8 mRNA were expressed strongly in leaves, roots, stems, flowers, pollen, and siliques. Chimeric GUS constructs expressed most of the vegetative tissues but almost no expression was detected in seed coates, hypocotyls, gynoecia, or pollen sacs.

b) Tissue-Specific or Tissue-Preferred Promoters

Furthermore preferred are promoters with specificities for seeds, such as, for example, the phaseolin promoter (U.S. Pat. No. 5,504,200; Bustos 1989; Murai 1983; Sengupta-Gopalan 1985), the promoter of the 2S albumin gene (Joseffson 1987), the legumine promoter (Shirsat 1989), the USP (unknown seed protein) promoter (Bäumlein 1991a), the napin gene promoter (U.S. Pat. No. 5,608,152; Stalberg 1996), the promoter of the sucrose binding proteins (WO 00/26388) or the legumin B4 promoter (LeB4; Bäumlein 1991b; Becker 1992), the *Arabidopsis* oleosin promoter (WO 98/45461), and the *Brassica* Bce4 promoter (WO 91/13980). Further preferred are a leaf-specific and light-induced promoter such as that from cab or Rubisco (Simpson 1985; Timko 1985); an anther-specific promoter such as that from LAT52 (Twell 1989b); and a microspore-preferred promoter such as that from apg (Twell 1983).

c) Chemically Inducible Promoters

The expression cassettes may also contain a chemically inducible promoter (review article: Gatz 1997), by means of which the expression of the exogenous gene in the plant can be controlled at a particular point in time. Such promoters such as, for example, the PRP1 promoter (Ward 1993), a salicylic acid-inducible promoter (WO 95/19443), a benzenesulfonamide-inducible promoter (EP 0 388 186), a tetracyclin-inducible promoter (Gatz 1991; Gatz 1992), an abscisic acid-inducible promoter EP 0 335 528) or an ethanol-cyclohexanone-inducible promoter (WO 93/21334) can likewise be used. Also suitable is the promoter of the glutathione-S transferase isoform II gene (GST-II-27), which can be activated by exogenously applied safeners such as, for example, N,N-diallyl-2,2-dichloroacetamide (WO 93/01294) and which is operable in a large number of tissues of both monocots and dicots. Further exemplary inducible promoters that can be utilized in the instant invention include that from the ACE1 system which responds to copper (Mett 1993); or the In2 promoter from maize which responds to benzenesulfonamide herbicide safeners (Hershey 1991; Gatz 1994). A promoter that responds to an inducing agent to which plants do not normally respond can be utilized.

An exemplary inducible promoter is the inducible promoter from a steroid hormone gene, the transcriptional activity of which is induced by a glucocorticosteroid hormone (Schena 1991).

Particularly preferred are constitutive promoters. Furthermore, promoters may be linked operably to the nucleic acid sequence to be expressed, which promoters make possible the expression in further plant tissues or in other organisms, such as, for example, *E. coli* bacteria. Suitable plant promoters are, in principle, all of the above-described promoters.

1.1.2.2 Preferred Promoter Sequences

While various promoters are known to be functional in soybean and are suitable to carry out the method of the invention, it has been found that especially ubiquitin promoters (especially the parsley ubiquitin promoter) result in a surprisingly high efficiency of selection. Thus in a preferred embodiment the promoter active in soybean is a plant ubiquitin promoter. More preferably, the plant ubiquitin promoter is the parsley (*Petroselinum crispum* or *Lomatium foeniculaceum*) ubiquitin promoter or the soybean ubiquitin promoter, more preferably the parsley ubiquitin promoter. As mentioned above, especially the parsley ubiquitin promoter has been shown to be adventitious and to result in consistently high transformation efficiency. The reasons for the superior performance of these promoters are not known. However, it is known that optimal selection needs expression of the selection marker in the relevant cells of the target tissue (which later dedifferentiate and regenerate into the transgenic plants), at the right time and to the right concentration (high enough to ensure efficient selection but not too high to prevent potential negative effects to the cells). The superior function and the effectiveness of the ubiquitin promoters (the parsley ubiquitin promoter particularly), may also indicate the need for soybean cells to have sufficient quantity of the D-alanine and/or D-serine metabolizing enzyme (e.g., the DSDA or DAO proteins) that are exogenous (non-native) to soybean, in order to survive the selection pressure imposed on them. These effects may be promoter and/or marker dependent, so that certain combinations of promoters and markers outperform others. The ubiquitin promoters thus can be employed as standard promoters to drive expression of D-amino acid metabolizing enzymes in soybean.

The constructs provided hereunder are novel and especially useful for carrying out the invention. Furthermore, they may provide use also in other plant species. In consequence, another embodiment of the invention relates to a heterologous nucleotide sequence comprising a) a ubiquitin promoter from a dicotyledonous plant specie, and operably linked thereto b) a nucleic acid sequence encoding an enzyme capable to metabolize D-alanine and/or D-serine, wherein said promoter is heterologous with respect to said nucleic acid sequence.

Several ubiquitin promoters from dicotyledonous plants are described (Callis 1989, 1990). Described are promoters from dicotyledonous plants, such as for potato (Garbarino 1992), tobacco (Genschick 1994), tomato (Hoffman 1991), parsely (Kawalleck 1993; WO03/102198, herein incorporated by reference), *Arabidopsis* (Callis 1990; Holtorf 1995; UBQ8, GenBank Acc.-No: NM_111814; UBQ1, GenBank Acc.-No: NM_115119; UBQ5, GenBank Acc.-No: NM_116090).

In general, the term "ubiquitin promoter" as used herein means the region of genomic DNA up to 5000 base pairs (bp) upstream from either the start codon, or a mapped transcriptional start site, of a ubiquitin, or ubiquitin-like, gene. Ubiquitin is an abundant 76 amino acid polypeptide found in all eukaryotic cells. There are several different genes that encode ubiquitin and their homology at the amino acid level is quite high. For example, human and mouse have many different genes encoding ubiquitin, each located at a different chromosomal locus. Functionally, all ubiquitin genes are critical players in the ubiquitin-dependent proteolytic machinery of the cell. Each ubiquitin gene is associated with a promoter that drives its expression. An ubiquitin promoter is the region of genomic DNA up to 5,000 bp upstream from either the start codon, or a mapped transcriptional start site, of a ubiquitin, or ubiquitin-like, gene. The term "plant ubiquitin regulatory system" refers to the approximately 2 kb nucleotide sequence 5' to the translation start site of a plant (preferably the parsley) ubiquitin gene and comprises sequences that direct initiation of transcription, regulation of transcription, control of expression level, induction of stress genes and enhancement of expression in response to stress. The regulatory system, comprising both promoter and regulatory functions, is the DNA sequence providing regulatory control or modulation of gene expression. Accordingly the ubiquitin promoter from a dicotyledonous of the invention is a DNA fragment (preferably approximately 0.5 to 2 kb in length), said DNA fragment comprising a plant ubiquitin regulatory system, wherein said regulatory system contains a promoter comprising a transcription start site, and—preferably—one or more heat shock elements positioned 5' to said transcription start site, and—preferably—an intron positioned 3' to said transcription start site, wherein said regulatory system is capable of regulating expression in soybeans.

Preferably, the ubiquitin promoter is the parsley ubiquitin promoter or the soybean (*Glycine max*) ubiquitin promoter. Sequences for the parsley and the soybean ubiquitin are provided hereunder (SEQ ID NO: 5 and 6, respectively). The disclosed sequences are comprising the It is known to the person skilled in the art that promoter sequences can be modified (e.g., truncated, fused, mutated) to a large extent without significantly modifying their transcription properties. In consequence another embodiment of the invention relates to a heterologous nucleotide sequence comprising a derivative or fragment of the parsley ubiquitin or soybean ubiquitin promoter. These might be synthetic sequences (i.e. as such not existing in nature), or orthologous sequences from other plant species. Thus, another embodiment of the invention relates to a heterologous nucleotide sequence comprising a) a promoter selected from the group consisting of
  i) sequences comprising the sequence as described by SEQ ID NO: 7 or 8, and
  ii) sequences comprising at least one fragment of at least 50 (preferably 100 or 150, more preferably 200 or 250, even more preferably 300 or 500) consecutive base pairs of the sequence as described by SEQ ID NO: 7 or 8, and having promoter activity in soybean,
  iii) sequences comprising a sequence having at least 60% (preferably 70% or 75%, more preferably 80% or 85%, even more preferably 90% or 95%, most preferably 98%) identity to the sequence as described by SEQ ID NO: 7 or 8, and having promoter activity in soybean,
  iv) sequences comprising a sequence hybridizing (preferably under conditions equivalent or equal to hybridization with a buffer solution of 30 to (preferably) 35% formamide, 1 M NaCl, 1% SDS at 37° C., and a wash in 1× to 2×SSC (preferably 1×SSC) at 50 to (preferably) 55° C.), more preferably in 40 to (preferably) 45% formamide, 1.0 M NaCl, 1% SDS at 37° C., and a wash in 0.5× to 1×SSC (preferably 0.5×SSC) at 55 to (preferably) 60° C.), and most preferably in 50% formamide, 1 M NaCl, 1% SDS at 37° C., and a wash in 0.1×SSC at 60 to (preferably) 65° C.) to the sequence as described by SEQ ID NO: 7 or 8, and having promoter activity in soybean,
  and
b) a nucleic acid sequence encoding an enzyme capable to metabolize D-alanine and/or D-serine,
wherein said promoter is heterologous with respect to said nucleic acid sequence.

"Promoter activity" in soybean plants means the capability to realize transcription of an operably linked nucleic acid sequence in at least one cell or tissue of a soybean plant or derived from a soybean plant. Preferably it means a constitutive transcription activity allowing for expression in most tissues and most developmental stages.

Accordingly the ubiquitin promoter utilized of the invention may also be a fragment of the promoter described by SEQ ID NO: 7 or 8 or a derivative thereof. Fragments may include truncated versions of the promoter as described by SEQ ID NO: 7 or 8, wherein un-essential sequences have been removed. Shortened promoter sequences are of high advantage since they are easier to handle and sometime optimized in their gene expression profile. One efficient, targeted means for preparing shortened or truncated promoters relies upon the identification of putative regulatory elements within the promoter sequence. This can be initiated by comparison with promoter sequences known to be expressed in similar tissue-specific or developmentally unique manner. Sequences, which are shared among promoters with similar expression patterns, are likely candidates for the binding of transcription factors and are thus likely elements that confer expression patterns. Confirmation of these putative regulatory elements can be achieved by deletion analysis of each putative regulatory region followed by functional analysis of each deletion construct by assay of a reporter gene, which is functionally attached to each construct. As such, once a starting promoter sequence is provided, any of a number of different deletion mutants of the starting promoter could be readily prepared. Functionally equivalent fragments of an ubiquitin promoter (e.g., as described by SEQ ID NO: 7 or 8) can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the B10BASE database "Transfac" (Biologische Datenbanken GmbH, Braunschweig; Wingender 2001) or the database PlantCARE (Lescot 2002). Preferably, functional equivalent fragments of one of the transcription regulating nucleotide sequences of the invention comprises at least 100 base pairs, preferably, at least 200 base pairs, more preferably at least 500 base pairs of a transcription regulating nucleotide sequence as described by SEQ ID NO: 7 or 8. More preferably this fragment is starting from the 3'-end of the indicated sequences.

Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis).

Beside the ubiquitin promoter other promoters has been shown to be suitable for achieving D-amino acid resistance in soybean, these include the *Arabidopsis* Actin 2 promoter and the nos promoter. However transformation efficiency is significantly less efficient than with the ubiquitin promoter.

1.1.3 Additional Elements

The expression cassettes of the invention (or the vectors in which these are comprised) may comprise further functional elements and genetic control sequences in addition to the promoter active in soybean plants (e.g., the ubiquitin promoter). The terms "functional elements" or "genetic control sequences" are to be understood in the broad sense and refer to all those sequences, which have an effect on the materialization or the function of the expression cassette according to the invention. For example, genetic control sequences modify the transcription and translation. Genetic control sequences are described (e.g., Goeddel 1990; Gruber 1993 and the references cited therein).

Preferably, the expression cassettes according to the invention encompass a promoter active in soybean plants (e.g, the ubiquitin promoter) 5'-upstream of the nucleic acid sequence (e.g., encoding the D-amino acid metabolizing enzyme), and 3'-downstream a terminator sequence and polyadenylation signals and, if appropriate, further customary regulatory elements, in each case linked operably to the nucleic acid sequence to be expressed.

Genetic control sequences and functional elements furthermore also encompass the 5'-untranslated regions, introns or non coding 3'-region of genes, such as, for example, the actin-1 intron, or the Adh1-S introns 1, 2 and 6 (general reference: The Maize Handbook, Chapter 116, Freeling and Walbot, Eds., Springer, New York (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5' leader sequence (Gallie 1987) and the like. Furthermore, they may promote tissue specificity (Rouster 1998).

Polyadenylation signals which are suitable as genetic control sequences are plant polyadenylation signals, preferably those which correspond essentially to T-DNA polyadenylation signals from *Agrobacterium tumefaciens*. Examples of particularly suitable terminator sequences are the OCS (octopine synthase) terminator and the NOS (nopaline synthase) terminator.

The genetic component and/or expression cassette of the invention may comprise further functional elements. Functional elements may include for example (but shall not be limited to) selectable or screenable marker genes (in addition to the D-alanine or D-serine metabolizing enzymes). Selectable and screenable markers may include a) negative selection markers; i.e., markers conferring a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Especially preferred negative selection markers are those which confer resistance to herbicides (see below in the Co-transformation section for details).

b) Positive selection markers; i.e. markers conferring a growth advantage to a transformed plant in comparison with a non-transformed one such as the genes and methods described by Ebinuma et al. 2000a,b, and in EP-A 0 601 092.

c) Counter selection markers; i.e. markers suitable to select organisms with defined deleted sequences comprising said marker (Koprek 1999). Examples comprise the cytosine deaminase codA (Schlaman 1997).

d) Reporter genes; i.e. markers encoding readily quantifiable proteins (via color or enzyme activity; Schenborn 1999). Preferred are green fluorescent protein (GFP) (Sheen 1995; Haseloff 1997; Reichel 1996; Tian 1997; WO 97/41228; Chui 1996; Leffel 1997), and β-glucuronidase (GUS) being very especially preferred (Jefferson 1987a,b).

Functional elements which may be comprised in a vector of the invention include i) Origins of replication which ensure replication of the expression cassettes or vectors according to the invention in, for example, *E. coli*. Examples which may be mentioned are ORI (origin of DNA replication), the pBR322 ori or the P15A ori (Maniatis, 1989), ii) Multiple cloning sites (MCS) to enable and facilitate the insertion of one or more nucleic acid sequences, iii) Sequences which make possible homologous recombination, marker deletion, or insertion into the genome of a host organism. Methods based on the cre/lox (Sauer 1998; Odell 1990; Dale 1991), FLP/FRT (Lysnik 1993), or Ac/Ds system (Wader 1987; U.S. Pat. No. 5,225,341; Baker 1987; Lawson 1994) permit a—if appropriate tissue-specific and/or inducible—removal of a specific DNA sequence from the genome of the host organism. Control sequences may in this context mean the specific flanking sequences (e.g., lox sequences), which later allow removal (e.g., by means of cre recombinase) (see also see international patent application PCT/EP 2005/002734; WO 2005/090581)), iv) Elements, for example border sequences, which make possible the *Agrobacterium*-mediated transfer in plant cells for the transfer and integration into the plant genome, such as, for example, the right or left border of the T-DNA or the vir region.

1.2. The Second Expression Cassette

Preferably, the DNA construct inserted into the genome of the target plant comprises at least one-second expression cassette, which confers to the soybean plant an agronomically relevant trait. This can be achieved by expression of selection markers, trait genes, antisense RNA or double-stranded RNA. The person skilled in the art is aware of numerous sequences which may be utilized in this context, e.g. to increase quality of food and feed, to produce chemicals, fine chemicals or pharmaceuticals (e.g., vitamins, oils, carbohydrates; Dunwell 2000), conferring resistance to herbicides, or conferring male sterility. Furthermore, growth, yield, and resistance against abiotic and biotic stress factors (like e.g., fungi, viruses or insects) may be enhanced. Advantageous properties may be conferred either by over-expressing proteins or by decreasing expression of endogenous proteins by e.g., expressing a corresponding antisense (Sheehy 1988; U.S. Pat. No. 4,801,340; Mol 1990) or double-stranded RNA (Matzke 2000; Fire 1998; Waterhouse 1998; WO 99/32619; WO 99/53050; WO 00/68374; WO 00/44914; WO 00/44895; WO 00/49035; WO 00/63364).

For expression of these sequences all promoters suitable for expression of genes in soybean can be employed. Preferably, said second expression construct is not comprising a promoter which is identical to the promoter used to express the D-amino acid metabolizing enzyme. Expression can be, for example, constitutive, inducible or development-dependent. Various promoters are known for expression in dicots such as soybean are known in the art (see above for details).

2. The Transformation and Selection Method of the Invention 2.1 Source and Preparation of the Plant Material Various plant materials can be employed for the transformation procedure disclosed herein. Such plant material may include but is not limited to for example leaf, root, immature and mature embryos, pollen, meristematic tissues, inflorescences, callus, protoplasts or suspensions of plant cells.

The plant material for transformation can be obtained or isolated from virtually any soybean variety or plant. Especially preferred are soybean plants selected from the group consisting of Jack, Resnik, Williams 82, Corsoy, Crawford, Hutcheson, Kunitz and Champ. Additional suitable soybean varieties are available from both academic and commercial institutions, such as—for example—the University of Guelph (Ontario Agricultural College; e.g. soybean varieties RCAT Staples, Westag 97, RCAT Bobcat, OAC Prudence, OAC Woodstock, OAC 9908), or soybean varieties from Daryland or Soygenetics. Additional suitable varieties are P1548402 (Peking), P1437654 (Er-hejjan), P1438489 (Chiquita), P1507354 (Tokei 421), P1548655 (Forrest), P1548988 (Pickett), P188788, P1404198 (Sun Huan Do), P1404166 (Krasnoaarmejkaja), Hartwig, Manokin, Doles, Dyer, and Custer.

Although several transformation and regeneration methods based on different soybean explants are described in the art (e.g., based on cotyledonary nodes), which are all well known to the person skilled in the art, the method of the invention is preferably based on axillary meristematic tissue, which more preferably is derived from the first or higher leaf node of a soybean plant. The axillary meristematic tissue of the primary or higher node can be provided by a seedling axillary meristem and employed in the subsequent transformation (e.g., *Agrobacterium* co-cultivation) step.

Preferably, the method of the invention comprises the following steps (a) providing an axillary meristematic tissue of a primary or higher leaf node of a soybean seedling, and
(b) co-cultivating said axillary meristematic tissue with a Rhizobiaceae bacterium comprising a transgenic T-DNA, said transgenic T-DNA comprising a DNA construct comprising at least one first expression construct comprising a promoter active in said soybean plant and operably linked thereto a nucleic acid sequence encoding an enzyme capable to metabolize D-alanine and/or D-serine
(c) transferring said co-cultivated axillary meristematic tissue on a shoot induction and selection medium comprising
  (i) at least one plant growth factor in a concentration suitable to induce de novo shoot induction from said axillary meristematic tissue, and
  (ii) D-alanine and/or D-serine and/or a derivative thereof in a total concentration from about 3 mM to about 100 mM for, and
  (iii) optionally one or more antibiotics suitable to inhibit Rhizobiaceae bacterium growth,
  and cultivating said co-cultivated axillary meristematic tissue for a period of at least 5 days on said medium until shoots are induced and developed therefrom and isolating said shoots, and
(d) transferring said isolated shoots to a rooting medium and cultivating said shoots on said rooting medium until said shoots have formed roots, and further regenerating the so derived plantlets into mature plants, which comprise inserted into their genome said transgenic T-DNA.

The method based on axillary meristematic tissue can employ explant tissue and/or cells from various sources, preferably from primary or higher leaf nodes. A primary leaf node is the node (i.e. the point on a stem where a leaf is attached or has been attached) directly following the cotyledonary node (i.e. the point on a stem where a cotyledonary leaf is attached or has been attached) when moving in the direction from the root to the leaves. Higher leaf nodes are all leaf nodes following the primary leaf node such as for example secondary, tertiary, quaternary etc. leaf nodes. Preferred is the axillary meristematic tissue of the primary leaf node.

Preferably, the axillary meristematic tissue of the primary or higher node is provided in a form selected from the group consisting of:

i) the seedling axillary meristem as provided by substantially the entire seedling, and
ii) the leaf axillary meristem as provided by dissecting the primary or higher leafs in a way that the axillary meristematic tissue remains attached to the petioles of the leafs, and
iii) propagated axillary meristem.

The axillary meristematic tissue of the primary or higher node can be provided and employed in various forms in the subsequent *Agrobacterium* co-cultivation step:

a) Method A: Seedling axillary meristem: The entire seedling or a substantial part thereof (such as the seedling minus roots or the seedling without one or both cotyledons) can be employed, inoculated with *Agrobacterium* and placed on shoot induction medium (SIM). Preferably the substantially entire seedling is selected from the group of material consisting of
  i) an entire seedling, and
  ii) a seedling having the roots removed, and
  iii) a seedling having one or both cotyledons removed, and
  iv) a seedling having the roots and one or both cotyledons removed, and
  v) a seedling having the roots, both cotyledons and part of the epicotyl removed leaving the axillary meristem attached to part of the epicotyl.
b) Method B: Leaf axillary meristem: The primary or higher leafs are dissected in a way that the axillary meristematic tissue remains attached to the petioles of the leaves, dipped in (inoculated with) *Agrobacterium* solution, co-cultivated on co-cultivation medium, and placed on the shoot induction medium (SIM). The small size of the explant and the vigorous growth of shoots should be favorable for the selection of transformed cells, which is problematic in current transformation methodologies.
c) Method C: Propagated axillary meristem: From a germinated (preferably about) 7-day old seedling the hypocotyl and one and a half or part of both cotyledons are removed from each seedling. The seedlings are then placed on propagation media for 2 to 4 weeks. The seedlings produce several branched shoots to obtain explants from. Axillary nodes from the first to the fourth leaf node can be excised. An average of three to four explants can be obtained from each seedling.

Beside the sources pointed out above, other sources may be suitable for the axillary meristematic tissue. These sources may for example be more restricted explants derived from a soybean seedling such as only the epicotyl and the primary leaf node. Obviously such restricted (i.e. small) explants can be obtained from the primary node but also from higher nodes as well (e.g., secondary and higher nodes).

The time period required for this method is greatly reduced compared to other *Agrobacterium*-mediated transformation protocols. Viable phenotypically positive soybean shoots can be collected 4 to 6 weeks from the initiation of the procedure. Furthermore, the method of the invention is highly genotype and cultivar independent.

The starting material for the transformation process is normally a soybean seed. The seed is first sterilized—optionally—soaked for softening. The seeds are then put on germination media and germinated for a time period of about 4 to 10 days, preferably for about 5 to 8 days, and most preferably for about 7 days. The epicotyl is preferably about 0.5 cm at this time for propagated axillary meristem and leaf axillary meristem methods and generally 0.5 to 2 cm for seedling axillary meristem method. Preferably germination is carried out under high light condition (>100 µM m$^{-2}$ s$^{-1}$) at 25° C.

2.2 Transformation Procedures 2.2.1 General Techniques

A DNA construct according to the invention may advantageously be introduced into cells using vectors into which said DNA construct is inserted. Examples of vectors may be plasmids, cosmids, phages, viruses, retroviruses or Agrobacteria. In an advantageous embodiment, the expression cassette is introduced by means of plasmid vectors. Preferred vectors are those, which enable the stable integration of the expression cassette into the host genome.

The DNA construct can be introduced into the target plant cells and/or organisms by any of the several means known to those of skill in the art, a procedure which is termed transformation. Various transformation procedures suitable for soybean have been described.

For example, the DNA constructs can be introduced directly to plant cells using ballistic methods, such as DNA particle bombardment, or the DNA construct can be introduced using techniques such as electroporation and microinjection of a cell. Particle-mediated transformation techniques (also known as "biolistics") are described in, e.g., EP-A1 270,356; U.S. Pat. No. 5,100,792, EP-A-444 882, EP-A-434 616; Klein 1987; Vasil 1993; and Becker 1994). These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants. Other transformation methods are also known to those skilled in the art.

Other techniques include microinjection (WO 92/09696, WO 94/00583, EP-A 331 083, EP-A 175 966, Green 1987), polyethylene glycol (PEG) mediated transformation (Paszkowski 1984; Lazzeri 1995), liposome-based gene delivery (WO 93/24640; Freeman 1984), electroporation (EP-A 290 395, WO 87/06614; Fromm 1985; Shimamoto 1992).

In the case of injection or electroporation of DNA into plant cells, the DNA construct to be transformed not need to meet any particular requirement (in fact the "naked" expression cassettes can be utilized). Simple plasmids such as those of the pUC series may be used.

2.2.2 Soil-Borne Bacteria Mediated Transformation (Co-Cultivation)

In addition and preferred to these "direct" transformation techniques, transformation can also be carried out by bacterial infection by means of soil born bacteria such as *Agrobacterium tumefaciens* or *Agrobacterium rhizogenes*.

2.2.2.1 Choice of Strains, Vectors, and Co-Cultivation Conditions

The soil-borne bacterium employed for transfer of a DNA (e.g., T-DNA) into soybean genome can be any specie of the Rhizobiaceae family. The Rhizobiaceae family comprises the genera *Agrobacterium*, *Rhizobium*, *Sinorhizobium*, and *Allorhizobium* are genera within the bacterial family and have been included in the alpha-2 subclass of Proteobacteria on the basis of ribosomal characteristics. Members of this family are aerobic, Gram-negative. The cells are normally rod-shaped (0.6-1.0 µm by 1.5-3.0 µm), occur singly or in pairs, without endospore, and are motile by one to six peritrichous flagella. Considerable extracellular polysaccharide slime is usually produced during growth on carbohydrate-containing media. Especially preferred are Rhizobiaceae such as *Sinorhizobium meliloti*, *Sinorhizobium medicae*, *Sinorhizobium fredi*, *Rhizobium* sp. NGR234, *Rhizobium* sp. BR816, *Rhizobium* sp. N33, *Rhizobium* sp. GRH2, *Sinorhizobium saheli*, *Sinorhizobium terangae*, *Rhizobium leguminosarum* biovar *trifolii*, *Rhizobium leguminosarum* biovar *viciae*, *Rhizobium leguminosarum* biovar *phaseoli*, *Rhizobium tropici*, *Rhizobium etli*, *Rhizobium galegae*, *Rhizobium gallicum*, *Rhizobium giardinii*, *Rhizobium hainanense*, *Rhizobium mongolense*, *Rhizobium lupini*, *Mesorhizobium loti*, *Mesorhizobium huakuii*, *Mesorhizobium ciceri*, *Mesorhizobium mediterraneium*, *Mesorhizobium tianshanense*, *Bradyrhizobium elkanni*, *Bradyrhizobium japonicum*, *Bradyrhizobium liaoningense*, *Azorhizobium caulinodans*, *Allobacterium undicola*, *Phyllobacterium myrsinacearum*, *Agrobacterium tumefaciens*, *Agrobacterium radiobacter*, *Agrobacterium rhizogenes*, *Agrobacterium vitis*, and *Agrobacterium rubi*. Preferred are also the strains and method described in Broothaerts (2005).

The monophyletic nature of *Agrobacterium*, *Allorhizobium* and *Rhizobium* and their common phenotypic generic circumscription support their amalgamation into a single genus, *Rhizobium*. The classification and characterization of *Agrobacterium* strains including differentiation of *Agrobacterium tumefaciens* and *Agrobacterium rhizogenes* and their various opine-type classes is a practice well known in the art (see for example Laboratory guide for identification of plant pathogenic bacteria, 3rd edition. (2001) Schaad, Jones, and Chun (eds.) ISBN 0890542635; for example the article of Moore et al. published therein). Recent analyses demonstrate that classification by its plant-pathogenic properties may not be justified. Accordingly more advanced methods based on genome analysis and comparison (such as 16S rRNA sequencing; RFLP, Rep-PCR, etc.) are employed to elucidate the relationship of the various strains (see for example Young 2003, Farrand 2003, de Bruijn 1996, Vinuesa 1998). The phylogenetic relationships of members of the genus *Agrobacterium* by two methods demonstrating the relationship of *Agrobacterium* strains K599 are presented in Llob 2003.

It is known in the art that not only *Agrobacterium* but also other soil-borne bacteria are capable to mediate T-DNA transfer provided that they the relevant functional elements for the T-DNA transfer of a Ti- or Ri-plasmid (Klein & Klein 1953; Hooykaas 1977; van Veen 1988).

Preferably, the soil-born bacterium is of the genus *Agrobacterium*. The term "*Agrobacterium*" as used herein refers to a soil-borne, Gram-negative, rod-shaped phytopathogenic bacterium. The species of *Agrobacterium*, *Agrobacterium tumefaciens* (syn. *Agrobacterium radiobacter*), *Agrobacterium rhizogenes*, *Agrobacterium rubi* and *Agrobacterium vitis*, together with *Allorhizobium undicola*, form a monophyletic group with all *Rhizobium* species, based on comparative 16S rDNA analyses (Sawada 1993, Young 2003). *Agrobacterium* is an artificial genus comprising plant-pathogenic species.

The term Ti-plasmid as used herein is referring to a plasmid, which is replicable in *Agrobacterium* and is in its natural, "armed" form mediating crown gall in *Agrobacterium* infected plants. Infection of a plant cell with a natural, "armed" form of a Ti-plasmid of *Agrobacterium* generally results in the production of opines (e.g., nopaline, agropine, octopine etc.) by the infected cell. Thus, *Agrobacterium* strains which cause production of nopaline (e.g., strain LBA4301, C58, A208) are referred to as "nopaline-type" Agrobacteria; *Agrobacterium* strains which cause production of octopine (e.g., strain LBA4404, Ach5, B6) are referred to as "octopine-type" Agrobacteria; and *Agrobacterium* strains which cause production of agropine (e.g., strain EHA105, EHA101, A281) are referred to as "agropine-type" Agrobacteria. A disarmed Ti-plasmid is understood as a Ti-plasmid lacking its crown gall mediating properties but otherwise providing the functions for plant infection. Preferably, the T-DNA region of said "disarmed" plasmid was modified in a way, that beside the border sequences no functional internal Ti-sequences can be transferred into the plant genome. In a preferred embodiment—when used with a binary vector system—the entire T-DNA region (including the T-DNA borders) is deleted.

The term Ri-plasmid as used herein is referring to a plasmid, which is replicable in *Agrobacterium* and is in its natural, "armed" form mediating hairy-root disease in *Agrobacterium* infected plants. Infection of a plant cell with a natural, "armed" form of an Ri-plasmid of *Agrobacterium* generally results in the production of opines (specific amino sugar derivatives produced in transformed plant cells such as e.g., agropine, cucumopine, octopine, mikimopine etc.) by the infected cell. *Agrobacterium rhizogenes* strains are traditionally distinguished into subclasses in the same way *A. tumefaciens* strains are. The most common strains are agropine-type strains (e.g., characterized by the Ri-plasmid pRi-A4), mannopine-type strains (e.g., characterized by the Ri-plasmid pRi8196) and cucumopine-type strains (e.g., characterized by the Ri-plasmid pRi2659). Some other strains are of the mikimopine-type (e.g., characterized by the Ri-plasmid pRi1723). Mikimopine and cucumopine are stereo isomers but no homology was found between the pRi plasmids on the nucleotide level (Suzuki 2001). A disarmed R-plasmid is understood as a Ri-plasmid lacking its hairy-root disease mediating properties but otherwise providing the functions for plant infection. Preferably, the T-DNA region of said "disarmed" Ri plasmid was modified in a way, that beside the border sequences no functional internal Ri-sequences could be transferred into the plant genome. In a preferred embodiment—when used with a binary vector system—the entire T-DNA region (including the T-DNA borders) is deleted.

The Ti and Ri plasmids of *A. tumefaciens* and *A. rhizogenes*, respectively, carry genes responsible for genetic transformation of the plant (Kado 1991). Vectors are based on the *Agrobacterium* Ti- or Ri-plasmid and utilize a natural system of DNA transfer into the plant genome. As part of this highly developed parasitism *Agrobacterium* transfers a defined part of its genomic information (the T-DNA; flanked by about 25 bp repeats, named left and right border) into the chromosomal DNA of the plant cell (Zupan 2000). By combined action of the so called vir genes (part of the original Ti-plasmids) said DNA-transfer is mediated. For utilization of this natural system, Ti-plasmids were developed which lack the original tumor inducing genes ("disarmed vectors"). In a further improvement, the so called "binary vector systems", the T-DNA was physically separated from the other functional elements of the Ti-plasmid (e.g., the vir genes), by being incorporated into a shuttle vector, which allowed easier handling (EP-A 120 516; U.S. Pat. No. 4,940,838). These binary vectors comprise (beside the disarmed T-DNA with its border sequences), prokaryotic sequences for replication both in *Agrobacterium* and *E. coli*. It is an advantage of *Agrobacterium*-mediated transformation that in general only the DNA flanked by the borders is transferred into the genome and that preferentially only one copy is inserted. Descriptions of *Agrobacterium* vector systems and methods for *Agrobacterium*-mediated gene transfer are known in the art (Miki 1993; Gruber 1993; Moloney 1989).

Hence, for Agrobacteria-mediated transformation the genetic composition (e.g., comprising an expression cassette) is integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the expression cassette to be introduced in the form of a flanking region. Binary vectors are preferably used. Binary vectors are capable of replication both in *E. coli* and in *Agrobacterium*. They may comprise a selection marker gene and a linker or polylinker (for insertion of e.g. the expression cassette to be transferred) flanked by the right and left T-DNA border sequence. They can be transferred directly into *Agrobacterium* (Holsters 1978). The selection marker gene permits the selection of transformed Agrobacteria and is, for example, the nptII gene, which confers resistance to kanamycin. The *Agrobacterium* which acts as the host organism in this case should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP 120 516; Hoekema 1985).

Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Preferably the soil-borne bacterium is a bacterium belonging to family *Agrobacterium*, more preferably a disarmed *Agrobacterium tumefaciens* or *rhizogenes* strain. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101[pEHA101] (Hood 1986), EHA105 [pEHA105] (Li 1992), LBA4404[pAL4404] (Hoekema 1983), C58C1[pMP90] (Koncz & Schell 1986), and C58C1 [pGV2260] (Deblaere 1985). Other suitable strains are *Agrobacterium tumefaciens* C58, a nopaline strain. Other suitable strains are *A. tumefaciens* C58C1 (Van Larebeke 1974), A136 (Watson 1975) or LBA4011 (Klapwijk 1980). In another preferred embodiment the soil-borne bacterium is a disarmed strain variant of *Agrobacterium rhizogenes* strain K599 (NCPPB 2659). Such strains are described in U.S. provisional application No. 60/606,789, filed Sep. 2, 2004, and international application PCT/EP2005/009366 hereby incorporated entirely by reference.

A binary vector or any other vector can be modified by common DNA recombination techniques, multiplied in *E. coli*, and introduced into *Agrobacterium* by e.g., electroporation or other transformation techniques (Mozo 1991).

Agrobacteria are grown and used in a manner as known in the art. The vector comprising *Agrobacterium* strain may, for example, be grown for 3 days on YEP medium (5 g/l yeast extract, 10 g/l peptone, 5 g/l NaCl, 15 g/l agar, pH 6.8; see Example 2) supplemented with the appropriate antibiotic (e.g., 50 mg/l spectinomycin). Bacteria are collected with a loop from the solid medium and resuspended. In a preferred embodiment of the invention, *Agrobacterium* cultures are started by use of aliquots frozen at −80° C. For *Agrobacterium* treatment of the various soybean axillary meristem explant tissues, the bacteria are preferably resuspended in the co-cultivation medium (CCM). The concentration of *Agrobacterium* used for infection, direct contact time, and co-cultivation may need to be varied. Thus, generally a range of *Agrobacterium* concentrations from $OD_{600}$ 0.1 to 3.0. Preferably for the various axillary meristematic tissue explants the following concentrations of *Agrobacterium* suspensions are employed:
a) Method A (seedling axillary meristem): From about $OD_{600}$=0.5 to about 3, preferably from about $OD_{600}$=1 to 2.
b) Method B (leaf axillary meristem): From about $OD_{600}$=0.1 to about 1, preferably from about $OD_{600}$=0.125 to 0.5.
c) Method C (propagated axillary meristem): From about $OD_{600}$=0.2 to about 1.5, preferably from about $OD_{600}$=0.5 to 0.8.

The explants are then inoculated with the *Agrobacterium* culture for a few minutes to a few hours, typically about 10 minutes to 3 hours, preferably about 0.5 hours to 1 hour. The excess media is drained and the *Agrobacterium* are permitted to co-cultivate with the meristem tissue for about 1 to about 6 days, preferably about 3 to about 5 days for *Agrobacterium tumefaciens* strains, and about 2 to about 3 days for *Agrobacterium rhizogenes* strains, preferably in the dark. During this step, the *Agrobacterium* transfers the foreign genetic construct into some cells in the soybean axillary meristem. Normally no selection compound is present during this step.

2.2.2.2 Modifications for Enhancing Transformation Efficiency

Supplementation of the co-culture medium with ethylene inhibitors (e.g., silver nitrate), phenol-absorbing compounds (like polyvinylpyrrolidone, Perl 1996) or antioxidants (such as thiol compounds, e.g., dithiothreitol, L-cysteine, Olhoft 2001) which can decrease tissue necrosis due to plant defense responses (like phenolic oxidation) may further improve the efficiency of *Agrobacterium*-mediated transformation.

Supplementation of the co-cultivation medium with antioxidants (e.g., dithiothreitol), or thiol compounds (e.g., L-cysteine, Olhoft 2001; US2001034888) which can decrease tissue necrosis due to plant defense responses (like phenolic oxidation) may further improve the efficiency of *Agrobacterium*-mediated transformation. In another preferred embodiment, the co-cultivation medium of comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate.

The target tissue and/or the Agrobacteria may be treated with a phenolic compound prior to or during the *Agrobacterium* co-cultivation. "Plant phenolic compounds" or "plant phenolics" suitable within the scope of the invention are those isolated substituted phenolic molecules which are capable to induce a positive chemotactic response, particularly those who are capable to induce increased vir gene expression in a Ti-plasmid containing *Agrobacterium* sp., particularly a Ti-plasmid containing Agrobacterium tumefaciens. A preferred plant phenolic compound is acetosyringone (3,5-dimethoxy-4-hydroxyacetophenone). Certain compounds, such as osmo-protectants (e.g. L-proline preferably at a concentration of about 200-1000 mg/L or betaine), phytohormes (inter alia NAA), opines, or sugars, act synergistically when added in combination with plant phenolic compounds.

Particularly suited induction conditions for *Agrobacterium tumefaciens* have been described (Vernade 1988). Efficiency of transformation with *Agrobacterium* can be enhanced by numerous other methods known in the art like for example vacuum infiltration (WO 00/58484), heat shock and/or centrifugation, addition of silver nitrate, sonication etc.

Preferably the method of the invention comprises one or more additional steps selected from the group of:
(a1) wounding the explant prior to, during or immediately after co-cultivation, and
(b1) transferring said co-cultivated axillary meristematic tissue after step (b) to a medium comprising at least one antibiotic suitable to inhibit *Agrobacterium* growth, and—optionally—at least one plant growth factor, wherein said medium is preferably lacking D-alanine and/or D-serine or a derivative thereof in a phytotoxic concentration, and,
(b2) further incubating said axillary, meristematic tissue after step (b) and—optionally (b1)—on a shoot induction medium (SIM) comprising at least one plant growth factor, wherein said shoot induction medium is preferably lacking D-alanine and/or D-serine or a derivative thereof in a phytotoxic concentration, and
(c1) transferring said shoots after step (c or b2) to a shoot elongation medium comprising
 (i) at least one plant growth factor in a concentration suitable to allow shoot elongation, and
 (ii) optionally D-alanine and/or D-serine or a derivative thereof in a total concentration from about 3 to about 100 mM,
 and cultivating said transferred shoots on said shoot elongation medium until said shoots have elongated to a length of at least about 2 cm.

In a preferred embodiment of the invention, the axillary meristematic tissue is wounded (step (a1)). Wounding seems to have at least two enhancing effects on the method of the invention:
(i) wounding facilitates *Agrobacterium* infection and gene transfer efficiency,
(ii) wounding enhances efficiency of de novo shoot induction presumably by disrupting the meristematic tissue connection significantly increasing the number of shoots developing from the explant tissue.

Wounding can be prior to inoculation (co-cultivation), during inoculation or after inoculation with *Agrobacterium*. For achieving both beneficial effects wounding is preferably done prior to or during co-cultivation, more preferably prior to co-cultivation. Many methods of wounding can be used, including, for example, cutting, abrading, piercing, poking, penetration with fine particles or pressurized fluids, plasma wounding, application of hyperbaric pressure, or sonication. Wounding can be performed using objects such as, but not limited to, scalpels, scissors, needles, abrasive objects, airbrush, particles, electric gene guns, or sound waves. Another alternative to enhance efficiency of the co-cultivation step is vacuum infiltration (Bechtold 1998; Trieu 2000).

2.3 Post Co-Cultivation Treatment

After the co-cultivation it is preferred to remove the soilborne bacteria by washing and/or treatment with appropriate antibiotics. In consequence, the medium employed after the co-cultivation step e.g., the medium employed in step (b1), (b2), and/or (c1) preferably contains a bacteriocide (antibiotic). This step is intended to terminate or at least retard the growth of the non-transformed cells and kill the remaining Agrobacterium cells. Accordingly, the method of the invention comprises preferably the step of:

(b1) transferring said co-cultivated axillary meristematic tissue after step (b) to a medium comprising at least one antibiotic suitable to inhibit *Agrobacterium* growth, and—optionally—at least one plant growth factor, wherein said medium is preferably lacking D-alanine and/or D-serine or a derivative thereof in a phytotoxic concentration, and, Preferred antibiotics to be employed are e.g., carbenicillin (500 mg/L or—preferably—100 mg/L) or Timentin™ (GlaxoSmithKline; used preferably at a concentration of about 250-500 mg/L; Timentin™ is a mixture of ticarcillin disodium and clavulanate potassium; 0.8 g Timentin™ contains 50 mg clavulanic acid with 750 mg ticarcillin. Chemically, ticarcillin disodium is N-(2-Carboxy-3,3-dimethyl-7-oxo-4-thia-1-azabicyclo[3.2.0]hept-6-yl)-3-thiophenemalonamic acid disodium salt. Chemically, clavulanate potassium is potassium (Z)-(2R,5R)-3-(2-hydroxyethylidene)-7-oxo-4-oxa-1-azabicyclo [3.2.0]heptane-2-carboxylate).

2.4 Selection

*Agrobacterium*-mediated techniques typically result in gene delivery into a very limited number of cells in the targeted tissue. Especially for soybeans transformation efficiencies (without selection) are in general very low. This problem is overcome by the selection protocol based on D-alanine and/or D-serine metabolizing enzymes provided herein. Thus, after co-cultivation and—optionally—a recovery step (see below) the target tissue (e.g., the axillary meristematic tissue) is transferred to and incubated on a selection medium.

It is preferred that freshly transformed (co-cultivated) explants are incubated for a certain time from about 1 hour to about 10 days, preferably from 1 day to 8 days, more preferably from about 4 to about 7 days after co-cultivation (step (b) or (b1)) on a medium lacking the selection compound (D-alanine and/or D-serine or a derivative thereof in a phytotoxic concentration). Establishment of a reliable resistance level against said selection compound needs some time to prevent unintended damage by the selection compound even to the transformed cells and tissue. Accordingly, the method of the invention may comprise a step between co-cultivation and selection, which is carried out without a selection compound. During this recovery period shoot induction (see below) may already be initiated.

The selection medium comprises D-alanine and/or D-serine or a derivative thereof in a phytotoxic concentration (i.e., in a concentration which either terminates or at least retard the growth of the non-transformed cells). The term "phytotoxic", "phytotoxicity" or "phytotoxic effect" as used herein is intended to mean any measurable, negative effect on the physiology of a plant or plant cell resulting in symptoms including (but not limited to) for example reduced or impaired growth, reduced or impaired photosynthesis, reduced or impaired cell division, reduced or impaired regeneration (e.g., of a mature plant from a cell culture, callus, or shoot etc.), reduced or impaired fertility etc. Phytotoxicity may further include effects like e.g., necrosis or apoptosis. In a preferred embodiment results in a reduction of growth or regenerability of at least 50%, preferably at least 80%, more preferably at least 90% in comparison with a plant which was not treated with said phytotoxic compound.

The specific compound employed for selection is chosen depending on which marker protein is expressed. For example in cases where the *E. coli* D-serine ammonia-lyase is employed, selection is done on a medium comprising D-serine. In cases where the *Rhodotorula gracilis* D-amino acid oxidase is employed, selection is done on a medium comprising D-alanine and/or D-serine.

The fact that D-amino acids are employed does not rule out the presence of L-amino acid structures or L-amino acids. For some applications it may be preferred (e.g., for cost reasons) to apply a racemic mixture of D- and L-amino acids (or a mixture with enriched content of D-amino acids). Preferably, the ratio of the D-amino acid to the corresponding L-enantiomer is at least 1:1, preferably 2:1, more preferably 5:1, most preferably 10:1 or 100:1. The use of D-alanine has the advantage that racemic mixtures of D- and L-alanine can be applied without disturbing or detrimental effects of the L-enantiomer. Therefore, in an improved embodiment a racemic mixture of D/L-alanine is employed as compound The term "derivative" with respect to D-alanine or D-serine means chemical compound, which comprise the respective D-amino acid structure of D-alanine or D-serine, but are chemically modified. As used herein the term a "D-amino acid structure" (such as a "D-serine structure") is intended to include the D-amino acid, as well as analogues, derivatives and mimetics of the D-amino acid that maintain the functional activity of the compound. As used herein, a "derivative" also refers to a form of D-serine or D-alanine in which one or more reaction groups on the compound have been derivatized with a substituent group. The D-amino acid employed may be modified by an amino-terminal or a carboxy-terminal modifying group or by modification of the side-chain. The amino-terminal modifying group may be—for example—selected from the group consisting of phenylacetyl, diphenylacetyl, triphenylacetyl, butanoyl, isobutanoyl hexanoyl, propionyl, 3-hydroxybutanoyl, 4-hydroxybutanoyl, 3-hydroxypropionoyl, 2,4-dihydroxybutyroyl, 1-Adamantanecarbonyl, 4-methylvaleryl, 2-hydroxyphenylacetyl, 3-hydroxyphenylacetyl, 4-hydroxyphenylacetyl, 3,5-dihydroxy-2-naphthoyl, 3,7-dihydroxy-2-napthoyl, 2-hydroxycinnamoyl, 3-hydroxycinnamoyl, 4-hydroxycinnamoyl, hydrocinnamoyl, 4-formylcinnamoyl, 3-hydroxy-4-methoxycinnamoyl, 4-hydroxy-3-methoxycinnamoyl, 2-carboxycinnamoyl, 3,4-dihydroxyhydrocinnamoyl, 3,4-dihydroxycinnamoyl, trans-Cinnamoyl, (±)-mandelyl, (±)-mandelyl-(±)-mandelyl, glycolyl, 3-formylbenzoyl, 4-formylbenzoyl, 2-formylphenoxyacetyl, 8-formyl-1-napthoyl, 4-(hydroxymethyl)benzoyl, 3-hydroxybenzoyl, 4-hydroxybenzoyl, 5-hydantoinacetyl, L-hydroorotyl, 2,4-dihydroxybenzoyl, 3-benzoylpropanoyl, (±)-2,4-dihydroxy-3,3-dimethylbutanoyl, DL-3-(4-hydroxyphenyl)lactyl, 3-(2-hydroxyphenyl)propionyl, 4-(2-hydroxyphenyl)propionyl, D-3-phenyllactyl, 3-(4-hydroxyphenyl)propionyl, L-3-phenyllactyl, 3-pyridylacetyl, 4-pyridylacetyl, isonicotinoyl, 4-quinolinecarboxyl, 1-isoquinolinecarboxyl and 3-isoquinolinecarboxyl. The carboxy-terminal modifying group may be—for example—selected from the group consisting of an amide group, an alkyl amide group, an aryl amide group and a hydroxy group. The "derivative" as used herein is intended to include molecules which, mimic the chemical structure of a respective D-amino acid structure and retain the functional properties of the D-amino acid structure. Approaches to designing amino acid or peptide analogs, derivatives and mimetics are known in the art (e.g., see Farmer 1980; Ball 1990; Morgan 1989; Freidinger 1989; Sawyer 1995; Smith 1995; Smith 1994; Hirschman 1993). Other possible modifications include N-alkyl (or aryl) substitutions, or backbone crosslinking to construct lactams and other cyclic structures. Other derivatives include C-terminal hydroxymethyl derivatives, O-modified derivatives (e.g., C-terminal hydroxymethyl benzyl ether), N-terminally modified derivatives including substituted amides such as alkylamides and hydrazides. Furthermore, D-amino acid structure comprising herbicidal compounds may be employed. Such compounds are for example described in U.S. Pat. No. 5,059,239, and may include (but shall not be limited to) N-benzoyl-N-(3-chloro-4-fluorophenyl)-DL-alanine, N-benzoyl-N-(3-chloro-4-fluorophenyl)-DL-alanine methyl ester, N-benzoyl-N-(3-chloro-4-fluorophenyl)-DL-alanine ethyl ester, N-benzoyl-N-(3-chloro-4-fluorophenyl)-D-alanine, N-benzoyl-N-(3-chloro-4-fluorophenyl)-D-alanine methyl ester, or N-benzoyl-N-(3-chloro-4-fluorophenyl)-D-alanine isopropyl ester.

The selection compound (D-alanine and/or D-serine or a derivative thereof in a phytotoxic concentration) may be used in combination with other substances. For the purpose of application, the selection compound may also be used together with the adjuvants conventionally employed in the art of formulation, and are therefore formulated in known manner, e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions to be used, the methods of application, such as spraying, atomising, dusting, scattering, coating or pouring, are chosen in accordance with the intended objectives and the prevailing circumstances. However, more preferably the selection compound is directly applied to the medium. It is an advantage that stock solutions of the selection compound can be made and stored at room temperature for an extended period without a loss of selection efficiency.

The optimal concentration of the selection compound (i.e. D-alanine, D-serine, derivatives thereof or any combination thereof) may vary depending on the target tissue employed for transformation but in general (and preferably for transformation of axillary meristematic tissue) the total concentration (i.e. the sum in case of a mixture) of D-alanine, D-serine or derivatives thereof is in the range from about 0.5 mM to about 100 mM. For example in cases where the *E. coli* D-serine ammonia-lyase is employed, selection is done on a medium comprising D-serine (e.g., incorporated into agar-solidified MS media plates), preferably in a concentration from about 0.5 mM to about 100 mM, preferably about 1 mM to about 70 mM, more preferably about 2 mM to about 50 mM, most preferably about 3 mM to about 15 mM. In cases where the *Rhodotorula gracilis* D-amino acid oxidase is employed, selection is done on a medium comprising D-alanine and/or D-serine (e.g., incorporated into agar-solidified MS media plates), preferably in a total concentration from about 0.5 mM to 100 mM, preferably about 1 mM to about 70 mM, more preferably about 2 mM to about 50 mM, most preferably about 3 mM to about 15 mM. Preferably, D-alanine (e.g., if employed as only selection compound) is employed in a concentration of about 0.5 mM to about 100 mM, preferably about 1 mM to about 70 mM, more preferably about 2 mM to about 50 mM, most preferably about 3 mM to about 20 mM. Preferably, D-serine (e.g., if employed as only selection compound) is employed in a concentration of about 0.5 mM to about 100 mM, preferably about 1 mM to about 70 mM, more preferably about 2 mM to about 50 mM, most preferably about 3 mM to about 15 mM.

Also the selection time may vary depending on the target tissue used and the regeneration protocol employed. The selection pressure (by presence of the selection compound) by be hold for the entire regeneration process including shoot induction, shoot elongation, and rooting.

In general a selection time is at least about 5 days, preferably at least about 14 days. More specifically the total selection time under dedifferentiating conditions (i.e., callus or shoot induction) is from about 1 to about 10 weeks, preferably, about 3 to 7 weeks, more preferably about 3 to 4 weeks. However, it is preferred that the selection under the dedifferentiating conditions is employed for not longer than 70 days. Preferably, wherein selection is done using about 3 to about 20 mM D-alanine and/or D-serine for about 3 to 4 weeks under dedifferentiating conditions. In between the selection period the explants may be transferred to fresh selection medium one or more times. For the specific protocol provided herein it is preferred that two selection medium steps (e.g., one transfer to new selection medium) is employed. Preferably, the selection of step is done in two steps, using a first selection step for about 14 to 20 days, then transferring the surviving cells or tissue to a second selection medium with essentially the same composition than the first selection medium for additional 14 to 20 days. However, it is also possible to apply a single step selection. The presence of the D-amino acid metabolizing enzymes does not rule out that additional markers are employed.

2.5 Regeneration of Fertile Soybean Plants

After the co-cultivation step (and an optional recovery step) the co-cultivated explants are incubated on a shoot induction medium comprising at least one plant growth factor. Said incubation on shoot induction medium can be started immediately after the co-cultivation step (i.e. in parallel with step (b1) for inhibiting growth of the Agrobacteria) or after other intermediate steps such as (b1) (inhibiting growth of the Agrobacteria) and/or (b2) (regeneration without selection compound; see below).

The media employed for shoot induction (and/or shoot elongation) are preferably supplemented with one or more plant growth regulator, like e.g., cytokinin compounds (e.g., 6-benzylaminopurine) and/or auxin compounds (e.g., 2,4-D). The term "plant growth regulator" (PGR) as used herein means naturally occurring or synthetic (not naturally occurring) compounds that can regulate plant growth and development. PGRs may act singly or in consort with one another or with other compounds (e.g., sugars, amino acids). The term "auxin" or "auxin compounds" comprises compounds, which stimulate cellular elongation and division, differentiation of vascular tissue, fruit development, formation of adventitious roots, production of ethylene, and—in high concentrations— induce dedifferentiation (callus formation). The most common naturally occurring auxin is indoleacetic acid (IAA), which is transported polarly in roots and stems. Synthetic auxins are used extensively in modern agriculture. Synthetic auxin compounds comprise indole-3-butyric acid (IBA), naphthylacetic acid (NAA), and 2,4-dichlorophenoxyacetic acid (2,4-D). Compounds that induce shoot formation include, but not limited to, IAA, NAA, IBA, cytokinins, auxins, kinetins, glyphosate, and thiadiazuron. The term "cytokinin" or "cytokinin compound" comprises compounds, which stimulate cellular division, expansion of cotyledons, and growth of lateral buds. They delay senescence of detached leaves and, in combination with auxins (e.g. IAA), may influence formation of roots and shoots. Cytokinin compounds comprise, for example, 6-isopentenyladenine (IPA) and 6-benzyladenine/6-benzylaminopurine (BAP).

In one embodiment of the invention (especially for the method based on axillary meristematic tissue) the media of at least one of step (b) (co-cultivation), and/or (c) (shoot induction and selection), comprises a cytokinin (like e.g., 6-benzylaminopurine (BAP), preferably in a concentration equivalent to a concentration of about 1 μM to about 10 μM 6-benzylaminopurine. For the shoot induction medium a BAP concentration of about 1 to about 3 μM is preferred. Preferably, the BAP concentration is not higher than 5 μM.

Accordingly, in one embodiment, one or more phytohormone or cytokinins are added to the medium during co-cultivation. Preferably, the concentration of the phytohormone or cytokinins is between 0.1 and 20 microMolar, more preferred are between 1 and 10 microMolar. However, the person skilled in the art knows, starting from the provided data, how to adapted the concentrations to the specific conditions of the performed experiments, e.g. to the used medium, the incubation time, the temperature, the nature of the explants, etc. In one embodiment, BAP has a concentration of, e.g. in the range of around 1 to around 10 microMolar, for example around 7.5 microMolar. In one embodiment Kinetin is used, preferably in the range of around 1 microMolar to 10 microMolar, e.g. around, 1, 3, 5, or 7.5 microMolar. Preferred are between 1 and 8 microMolar Kinetin, e.g. 7.5 microMolar.

In another preferred embodiment, the media of at least one of step (b), (b1), (b2), and/or (c), comprises a cytokinin.

It is furthermore especially preferred, that the media of at least one of step (b), (b1), (b2), (c) and/or (c1), preferably at least (b) and (c1), comprises between about 0.1 µM and about 2 µM Gibberellic acid (GA3).

In another preferred embodiment, the media of at least one of step (b), (b1), (b2), and (c) comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate.

The explants are incubated on said shoot induction medium until shoots have been developed. The shoot primordia that form are usually no longer than 0.3 cm in size. Formation of shoot primordia begins around 1 week on shoot induction medium and, on average, such shoot initiation continues for about 3 to 4 weeks to reach maximum size. Accordingly, co-cultivated explants are incubated on said shoot induction medium for about 2 to 6 weeks, preferably about 3 to 4 weeks.

As described above shoot induction and the subsequent steps of regeneration are preferably carried out under selective conditions (e.g., supplementing the shoot induction medium, shoot elongation medium, rooting medium with D-serine or D-alanine at a concentration of from about 3 to 100 mM).

The tissue is grown upon this medium for a period of about 1 to about 4 weeks, preferably about 7 days until shoots have developed. Shoot formation begins in about 1 to about 2 weeks depending on treatment and co-cultivation conditions.

In a preferred embodiment all shoot primordia formed before transformation will be removed up to about 1 week after co-cultivation to stimulate new growth from the meristems. This helps to reduce chimerism in the primary transformant and increase amplification of transgenic meristematic cells. During this time the explant may or may not be cut into smaller pieces (i.e. detaching the node from the explant by cutting the epicotyl).

After 2 to 4 weeks (or until a mass of shoots has formed) on SIM medium (preferably with selection), the explants will be transferred to shoot elongation (SEM) medium that will stimulate shoot elongation (of the shoot primordia). This medium may or may not contain a selection compound, but preferably contains a selection compound (e.g., D-serine in a concentration from about 3 to about 20 mM). The tissue is grown upon this medium for a period of about 1 to about 8 weeks. The frequency and length of the elongated shoots are influenced by the hormone levels, in particular GA, in the SEM.

In another preferred embodiment of the invention, the media of at least one of step (c1) and/or (d) comprises between about 0.01 mg/l (0.057 M) and about 1 mg/l (5.7 µM) indole acetic acid (IAA), and/or between about 0.1 µM and about 4 µM Gibberellic acid (GA3), and/or between about 0.5 µM and about 6 µM trans-zeatin riboside acid.

Preferably, after every 2 to 3 weeks the explants are transferred to fresh SEM medium (preferably containing the selection compound) after carefully removing dead tissue. The explants should hold together and not fragment into pieces and remain somewhat healthy. Preferably, the explants will continue to be transferred until the explant dies or shoots elongate.

The elongated shoots are ready for harvest about 4 to 8 weeks after transfer to the shoot elongation medium. The shoots are evaluated for phenotypic regularity and health, and only shoots with elongated stems (approximately 1 inch or 2 cm) and full trifoliate leaf formation are harvested.

The collected shoots are placed on a rooting medium to induce root formation. Root formation takes approximately 1 to 4 weeks, following which the plants can be transferred to soil and grown to full maturity. The rooting medium may (also not explicitly preferred) also contain the selection compound. Preferably, elongated shoots (length larger than 3 cm) are removed and placed into rooting medium (RM) for about 1 week (Method B), or about 2 to 4 weeks depending on the cultivar (Method C) at which time roots begin to form. In the case of explants with roots, they are transferred directly into soil. Rooted shoots are transferred to soil and hardened in a growth chamber for 2 to 3 weeks before transferring to the greenhouse. Regenerated plants obtained using this method are fertile and have produced on average 500 seeds per plant.

The $T_0$ plants created by this technique are transgenic plants and are regularly recovered with quite reasonable yields. For Method C, the average regeneration time of a soybean plantlet using the propagated axillary meristem protocol is 14 weeks from explant inoculation. Therefore, this method has a quick regeneration time that leads to fertile, healthy soybean plants.

Transformed plant material (e.g., cells, tissues or plantlets), which express marker genes, are capable of developing in the presence of concentrations of a corresponding selection compound which suppresses growth of an untransformed wild type tissue. The resulting plants can be bred and hybridized in the customary fashion. Two or more generations should be grown in order to ensure that the genomic integration is stable and hereditary. Other important aspects of the invention include the progeny of the transgenic plants prepared by the disclosed methods, as well as the cells derived from such progeny, and the seeds obtained from such progeny.

Another embodiment of the invention relates to the soybean cells and plants made by the method provided hereunder. Thus, another embodiment relates to a soybean plant or cell comprising a DNA construct comprising a promoter active in said soybean plants or cells and operably linked thereto a nucleic acid sequence encoding an enzyme capable to metabolize D-alanine or D-serine, wherein said promoter is heterologous in relation to said enzyme encoding sequence. Preferably, the promoter and/or the enzyme capable to metabolize D-alanine or D-serine are defined as above. More preferably, said soybean plant or cell is further comprising at least one second expression construct conferring to said soybean plant an agronomically valuable trait. Other embodiments of the invention relate to parts of said soybean plant including but not limited to soybean seeds (soybeans) and their use for food, feed, and industrial purposes.

In one preferred embodiment the soybean plant selected from the group consisting of Jack, Resnik, Williams 82, Corsoy, Crawford, Hutcheson, Kunitz and Champ. Additional suitable soybean varieties are available from both academic and commercial institutions, such as—for example—the University of Guelph (Ontario Agricultural College; e.g. soybean varieties RCAT Staples, Westag 97, RCAT Bobcat, OAC Prudence, OAC Woodstock, OAC 9908), or soybean varieties from Daryland or Soygenetics. Additional suitable varieties are P1548402 (Peking), P1437654 (Er-hejjan), P1438489 (Chiquita), P1507354 (Tokei 421), P1548655 (Forrest), P1548988 (Pickett), P188788, P1404198 (Sun Huan Do), P1404166 (Krasnoarmejkaja), Hartwig, Manokin, Doles, Dyer, and Custer.

Other embodiments of the invention relate to parts, organs, cells, fruits, and other reproduction material of a soybean plant of the invention. Preferred parts are selected from the group consisting of tissue, cells, pollen, ovule, roots, leaves, seeds, microspores, and vegetative parts The resulting transgenic plants can be self pollinated or crossed with other soybean plants. T1 seeds are harvested, dried and stored properly with adequate label on the seed bags. Two or more generations should be grown in order to ensure that the genomic integration is stable and hereditary. For example transgenic events in T1 or T2 generations could be involved in pre breeding hybridization program for combining different transgenes (gene stacking). Other important aspects of the invention include the progeny of the transgenic plants prepared by the disclosed methods, as well as the cells derived from such progeny, and the seeds obtained from such progeny.

2.6 Generation of Descendants

After transformation, selection and regeneration of a transgenic plant (comprising the DNA construct of the invention) descendants are generated, which—because of the activity of the excision promoter—underwent excision and do not comprise the marker sequence(s) and expression cassette for the endonuclease.

Descendants can be generated by sexual or non-sexual propagation. Non-sexual propagation can be realized by introduction of somatic embryogenesis by techniques well known in the art. Preferably, descendants are generated by sexual propagation/fertilization. Fertilization can be realized either by selfing (self-pollination) or crossing with other transgenic or non-transgenic plants. The transgenic plant of the invention can herein function either as maternal or paternal plant. After the fertilization process, seeds are harvested, germinated and grown into mature plants. Isolation and identification of descendants, which underwent the excision process can be done at any stage of plant development. Methods for said identification are well known in the art and may comprise—for example—PCR analysis, Northern blot, Southern blot, or phenotypic screening (e.g., for an negative selection marker).

Descendants may comprise one or more copies of the agronomically valuable trait gene. Preferably, descendants are isolated which only comprise one copy of said trait gene.

Also in accordance with the invention are cells, cell cultures, parts—such as, for example, in the case of transgenic plant organisms, roots, leaves and the like—derived from the above-described transgenic organisms, and transgenic propagation material (such as seeds or fruits).

Genetically modified plants according to the invention, which can be consumed by humans or animals can also be used as food or feedstuffs, for example directly or following processing known per se. Here, the deletion of, for example, resistances to antibiotics and/or herbicides, as are frequently introduced when generating the transgenic plants, makes sense for reasons of customer acceptance, but also product safety.

A further subject matter of the invention relates to the use of the above-described transgenic organisms according to the invention and the cells, cell cultures, parts—such as, for example, in the case of transgenic plant organisms, roots, leaves and the like—derived from them, and transgenic propagation material such as seeds or fruits, for the production of food or feedstuffs, pharmaceuticals or fine chemicals. Fine chemicals is understood as meaning enzymes, vitamins, amino acids, sugars, fatty acids, natural and synthetic flavors, aromas and colorants. Especially preferred is the production of tocopherols and tocotrienols, and of carotenoids. Culturing the transformed host organisms, and isolation from the host organisms or from the culture medium, is performed by methods known to the skilled worker. The production of pharmaceuticals such as, for example, antibodies or vaccines, is described (e.g., by Hood 1999; Ma 1999).

3. Further Modifications 3.1 Counter Selection and Subsequent Marker Deletion

The first expression construct for the D-amino acid metabolizing enzyme can be preferably constructed in a way to allow for subsequent marker deletion, especially when said enzyme is a D-amino acid oxidase, which can be employed both for negative selection and counter selection (i.e. as a dual-function marker). When based on D-amino acid oxidases the method of the invention can be used as a combined selection/marker deletion scheme. Based on the D-amino acid employed, D-amino acid oxidases can act either as negative or counter selection marker. Such methods are in detail described in PCT/EP 2005/002734 (WO 2005/090581), hereby incorporated entirely by reference.

For this purpose the first expression cassette is preferably flanked by sequences, which allow for specific deletion of said first expression cassette. This embodiment of the invention makes use of the property of D-amino oxidase (DAAO) to function as dual-function markers, i.e., as markers which both allow (depending on the used substrate) as negative selection marker and counter selection marker. In contrast to D-amino acids like D-serine and D-alanine (which are highly phytotoxic to plants and are "detoxified" by the D-amino acid oxidase), D-valine and D-isoleucine are not toxic to wild-type plants but are converted to toxic compounds by plants expressing the D-amino acid oxidase DAAO. The findings that DAAO expression mitigated the toxicity of D-serine and D-alanine, but induced metabolic changes that made D-isoleucine and D-valine toxic, demonstrate that the enzyme could provide a substrate-dependent, dual-function, selectable marker in plants.

Accordingly, another embodiment of the invention relates to a method for providing soybean cells and plants (which are preferably marker free), said method comprises the steps of:

i) transforming a soybean plant cell with a first DNA construct comprising
  a) at least one first expression construct comprising a promoter active in said soybean plant and operably linked thereto a nucleic acid sequence encoding a D-amino acid oxidase enzyme, wherein said first expression cassette is flanked by sequences which allow for specific deletion of said first expression cassette, and
  b) at least one second expression cassette suitable for conferring to said plant an agronomically valuable trait, wherein said second expression cassette is not localized between said sequences which allow for specific deletion of said first expression cassette, and ii) treating said transformed soybean plant cells of step i) with a first compound selected from the group consisting of D-alanine, D-serine or derivatives thereof in a phytotoxic concentration and selecting plant cells comprising in their genome said first DNA construct, conferring resistance to said transformed plant cells against said first compound by expression of said D-amino acid oxidase, and iii) inducing deletion of said first expression cassette from the genome of said transformed plant cells and treating said plant cells with a second compound selected from the group consisting of D-isoleucine, D-valine and derivatives thereof in a concentration toxic to plant cells still comprising said first expression cassette, thereby selecting plant cells comprising said second expression cassette but lacking said first expression cassette.

Preferred promoters and D-amino acid oxidase sequences are described above. Preferably, deletion of the first expression cassette can be realized by various means known in the art, including but not limited to one or more of the following methods:

a) recombination induced by a sequence specific recombinase, wherein said first expression cassette is flanked by corresponding recombination sites in a way that recombination between said flanking recombination sites results in deletion of the sequences in-between from the genome, b) homologous recombination between homology sequences A and A' flanking said first expression cassette, preferably induced by a sequence-specific double-strand break between said homology sequences caused by a sequence specific endonuclease, wherein said homology sequences A and A' have sufficient length and homology in order to ensure homologous recombination between A and A', and having an orientation which—upon recombination between A and A'—will lead to excision of said first expression cassette from the genome of said plant.

Various means are available for the person skilled in art to combine the deletion/excision inducing mechanism with the DNA construct of the invention comprising the D-amino acid oxidase dual-function selection marker. Preferably, a recombinase or endonuclease employable in the method of the invention can be expressed by a method selected from the group consisting of:

a) incorporation of a second expression cassette for expression of the recombinase or sequence-specific endonuclease operably linked to a plant promoter into said DNA construct, preferably together with said first expression cassette flanked by said sequences which allow for specific deletion, b) incorporation of a second expression cassette for expression of the recombinase or sequence-specific endonuclease operably linked to a plant promoter into the plant cells or plants used as target material for the transformation thereby generating master cell lines or cells, c) incorporation of a second expression cassette for expression of the recombinase or sequence-specific endonuclease operably linked to a plant promoter into a separate DNA construct, which is transformed by way of co-transformation with said first DNA construct into said plant cells, d) incorporation of a second expression cassette for expression of the recombinase or sequence-specific endonuclease operably linked to a plant promoter into the plant cells or plants which are subsequently crossed with plants comprising the DNA construct of the invention.

In another preferred embodiment the mechanism of deletion/excision can be induced or activated in a way to prevent pre-mature deletion/excision of the dual-function marker. Preferably, thus expression and/or activity of an preferably employed sequence-specific recombinase or endonuclease can be induced and/or activated, preferably by a method selected from the group consisting of a) inducible expression by operably linking the sequence encoding said recombinase or endonuclease to an inducible promoter, b) inducible activation, by employing a modified recombinase or endonuclease comprising a ligand-binding-domain, wherein activity of said modified recombinase or endonuclease can by modified by treatment of a compound having binding activity to said ligand-binding-domain.

Preferably, thus the method of the inventions results in a plant cell or plant which is selection marker-free.

Another subject matter of the invention relates to DNA constructs, which are suitable for employing in the method of the invention. A DNA construct suitable for use within the present invention is preferably comprising a) a first expression cassette comprising a nucleic acid sequence encoding a D-amino acid oxidase operably linked with a promoter active in soybean plants (as defined above; preferably an ubiquitin promoter), wherein said first expression cassette is flanked by sequences which allow for specific deletion of said first expression cassette, and b) at least one second expression cassette suitable for conferring to said plant an agronomically valuable trait, wherein said second expression cassette is not localized between said sequences which allow for specific deletion of said first expression cassette.

Preferred promoters and D-amino acid oxidase sequences are described above.

For ensuring marker deletion/excision the expression cassette for the D-amino acid oxidase (the first expression construct) comprised in the DNA construct of the invention is flanked by recombination sites for a sequence specific recombinase in a way the recombination induced between said flanking recombination sites results in deletion of the said first expression cassette from the genome. Preferably said sequences which allow for specific deletion of said first expression cassette are selected from the group of sequences consisting of a) recombination sites for a sequences-specific recombinase arranged in a way that recombination between said flanking recombination sites results in deletion of the sequences in-between from the genome, and b) homology sequences A and A' having a sufficient length and homology in order to ensure homologous recombination between A and A', and having an orientation which—upon recombination between A and A'—results in deletion of the sequences in-between from the genome.

Preferably, the construct comprises at least one recognition site for a sequence specific nuclease localized between said sequences, which allow for specific deletion of said first expression cassette (especially for variant b above).

There are various recombination sites and corresponding sequence specific recombinases known in the art, which can be employed for the purpose of the invention. The person skilled in the art is familiar with a variety of systems for the site-directed removal of recombinantly introduced nucleic acid sequences. They are mainly based on the use of sequence specific recombinases. Various sequence-specific recombination systems are described, such as the Cre/lox system of the bacteriophage P1 (Dale 1991; Russell 1992; Osborne 1995), the yeast FLP/FRT system (Kilby 1995; Lyznik 1996), the Mu phage Gin recombinase, the *E. coli* Pin recombinase or the R/RS system of the plasmid pSR1 (Onouchi 1995; Sugita 2000). Also a system based on attP sites and bacteriophage Lambda recombinase can be employed (Zubko 2000). Further methods suitable for combination with the methods described herein are described in WO 97/037012 and WO 02/10415.

In a preferred embodiment, deletion/excision of the dual-marker sequence is deleted by homologous recombination induced by a sequence-specific double-strand break. The basic principles are disclosed in WO 03/004659, hereby incorporated by reference. For this purpose the first expression construct (encoding for the dual-function marker) is flanked by homology sequences A and A', wherein said homology sequences have sufficient length and homology in order to ensure homologous recombination between A and A', and having an orientation which—upon recombination between A and A'—will lead to an excision of first expression cassette from the genome. Furthermore, the sequence flanked by said homology sequences further comprises at least one recognition sequence of at least 10 base pairs for the site-directed induction of DNA double-strand breaks by a sequence specific DNA double-strand break inducing enzyme, preferably a sequence-specific DNA-endonuclease, more preferably a homing-endonuclease, most preferably an endonuclease selected from the group consisting of I-SceI, I-CeuI, I-CpaI, I-CpaII, I-CreI and I-ChuI or chimeras thereof with ligand-binding domains.

The expression cassette for the endonuclease or recombinase (comprising a sequence-specific recombinase or endonuclease operably linked to a plant promote) may be included in the DNA construct of the invention. Preferably, said second expression cassette is together with said first expression cassette flanked by said sequences which allow for specific deletion.

In another preferred embodiment, the expression and/or activity of said sequence-specific recombinase or endonuclease can be induced and/or activated for avoiding premature deletion/excision of the dual-function marker during a period where its action as a negative selection marker is still required. Preferably induction/activation can be realized by a method selected from the group consisting of
a) inducible expression by operably linking the sequence encoding said recombinase or endonuclease to an inducible promoter,
b) inducible activation, by employing a modified recombinase or endonuclease comprising a ligand-binding-domain, wherein activity of said modified recombinase or endonuclease can by modified by treatment of a compound having binding activity to said ligand-binding-domain.

Further embodiments of the inventions are related to transgenic vectors comprising a DNA construct of the invention. Transgenic cells or non-human organisms comprising a DNA construct or vector of the invention. Preferably said cells or non-human organisms are plant cells or plants, preferably plants, which are of agronomical use.

The present invention enables generation of marker-free transgenic cells and organisms, preferably plants, an accurately predictable manner with high efficiency.

The preferences for the counter selection step (ii) with regard to choice of compound, concentration, mode of application for D-alanine, D-serine, or derivatives thereof are described above in the context of the general selection scheme.

For the counter selection step (iii) the compound is selected from the group of compounds comprising a D-isoleucine or D-valine structure. More preferably the compound is selected from the group consisting of D-isoleucine and D-valine. Most preferably the compound or composition used for counter selection comprises D-isoleucine. When applied via the cell culture medium (e.g., incorporated into agar-solidified media plates), D-isoleucine can be employed in concentrations of about 0.5 mM to about 100 mM, preferably about 1 mM to about 50 mM, more preferably about 10 mM to about 30 mM. When applied via the cell culture medium (e.g., incorporated into agar-solidified media plates), D-valine can be employed in concentrations of about 1 to about 100 mM, preferably about 5 to 50 mM, more preferably about 15 mM to about 30 mM.

Thus, using the above described method it becomes possible to create a soybean plant, which is marker-free. The terms "marker-free" or "selection marker free" as used herein with respect to a cell or an organisms are intended to mean a cell or an organism which is not able to express a functional selection marker protein (encoded by expression cassette b; as defined above) which was inserted into said cell or organism in combination with the gene encoding for the agronomically valuable trait. The sequence encoding said selection marker protein may be absent in part or—preferably—entirely. Furthermore the promoter operably linked thereto may be dysfunctional by being absent in part or entirely. The resulting plant may however comprise other sequences which may function as a selection marker. For example the plant may comprise as a agronomically valuable trait a herbicide resistance conferring gene. However, it is most preferred that the resulting plant does not comprise any selection marker.

Various further aspects and embodiments of the present invention will be apparent to those skilled in the art in view of the present disclosure. All documents mentioned in this specification are incorporated herein in their entirety by reference. Certain aspects and embodiments of the invention will now be illustrated by way of example and with reference to the figure described below.

3.2 Gene Stacking

There is a shortage of efficient transformation systems and especially selection markers for soybean. This shortage refers especially to approaches, which rely on multiple subsequent transformation. One way to overcome this problem is the combined selection and marker deletion method provided above. Another method is based on combining different selection systems. The methods and compositions of the invention allow for subsequent transformation. The D-serine and/or D-alanine metabolizing enzymes are compatible and do not interfere with other selection marker and selection systems. It is therefore possible to transform existing transgenic plants comprising another selection marker with the constructs of the invention or to subsequently transform the plants obtained by the method of the invention (and comprising the expression constructs for the D-serine and/or D-alanine metabolizing enzyme) with another marker. In consequence, another embodiment of the invention relates to a method for subsequent transformation of at least two DNA constructs into a soybean plant comprising the steps of:
a) a transformation with a first construct said construct comprising at least one expression construct comprising a promoter active in said soybean plants (preferably a ubiquitin promoter as defined above) and operably linked thereto a nucleic acid sequence encoding an enzyme capable to metabolize D-alanine or D-serine, and
b) a transformation with a second construct said construct comprising a second selection marker gene, which is not conferring resistance against D-alanine or D-serine.

Preferably said second marker gene is a negative selection marker conferring a resistance to a biocidal compound such as a (non-D-amino acid) metabolic inhibitor (e.g., 2-deoxy-glucose-6-phosphate, WO 98/45456), antibiotics (e.g., kanamycin, G 418, bleomycin or hygromycin) or herbicides (e.g., phosphinothricin, sulfonylurea- and imidazolinone-type herbicides, or glyphosate). Examples are:

Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374)

5-enolpyruvylshikimate-3-phosphate synthase (EPSPS) conferring resistance to Glyphosate® (N-(phosphonomethyl)glycine) (Shah 1986; Della-Cioppa 1987a,b)

Glyphosate® degrading enzymes (Glyphosate® oxidoreductase; gox),

Dalapon inactivating dehalogenases (deh)

sulfonylurea- and/or imidazolinone-inactivating acetolactate synthases (ahas or ALS; for example mutated ahas/ALS variants with, for example, the S4, XI12, XA17, and/or Hra mutation Bromoxynil® degrading nitrilases (bxn)

Kanamycin- or. geneticin (G418) resistance genes (NPTII; NPTI) coding e.g., for neomycin phosphotransferases (Fraley 1983; Nehra 1994)

hygromycin phosphotransferase (HPT), which mediates resistance to hygromycin (Vanden Elzen 1985).

dihydrofolate reductase (Eichholtz 1987)

Various time schemes can be employed for the various negative selection marker genes. In case of resistance genes (e.g., against herbicides) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting. For example, with the phosphinotricin resistance gene (bar, PAT) as the selective marker, phosphinotricin or bialaphos at a concentration of from about 1 to 50 mg/l may be included in the medium.

Preferably said second marker is conferring resistance against at least one compound select from the group consisting of phosphinotricin, dicamba, glyphosate, sulfonylurea- and imidazolinone-type herbicides.

Also the products of said method as such are new and inventive over the art. Thus another embodiment of the invention relates to a soybean plant comprising a) a first expression construct comprising a promoter active in said soybean plants (preferably a ubiquitin promoter as defined above) and operably linked thereto a nucleic acid sequence encoding an enzyme capable to metabolize D-alanine or D-serine, and b) a second expression construct for a selection marker gene, which is not conferring resistance against D-alanine or D-serine.

Preferably, said second marker gene is defined as above and is most preferably conferring resistance against at least one compound select from the group consisting of phosphinotricin, dicamba, glyphosate, sulfonylurea- and imidazolinone-type herbicides.

The following combinations are especially preferred:

A first transformation with a selection marker conferring resistance against phosphinothricin followed by a second transformation with a dsdA selections marker gene;

A first transformation with a selection marker conferring resistance against phosphinothricin followed by a second transformation with a dao1 selection marker gene;

A first transformation with a dsdA selection marker gene followed by a second transformation with a selection marker conferring resistance against phosphinothricin;

A first transformation with a dao1 followed by a second transformation with a selection marker conferring resistance against phosphinothricin;

Beside the stacking with a second expression construct for a selection marker gene, which is not conferring resistance against D-alanine or D-serine, also the dsdA and dao1 genes can be stacked. For example a first selection can be made using the dsdA gene and D-serine as a selection agent and a second selection can be subsequently made by using dao1 gene and D-alanine as selection agent. Accordingly another embodiment of the invention relates to a method for subsequent transformation of at least two DNA constructs into a soybean plant comprising the steps of:

a) a transformation with a first construct said construct comprising an expression construct comprising a promoter active in said soybean plants and operably linked thereto a nucleic acid sequence encoding an dsdA enzyme and selecting with D-serine, and b) a transformation with a second construct said construct comprising an expression construct comprising promoter active in said soybean plants and operably linked thereto a nucleic acid sequence encoding a dao enzyme and selecting with D-alanine.

Also the products of said method are considered to be new and inventive over the art. Thus, another embodiment of the invention relates to a soybean plant comprising a) a first construct said construct comprising an expression construct comprising a promoter active in said soybean plants (preferably a ubiquitin promoter as defined above) and operably linked thereto a nucleic acid sequence encoding an dsdA enzyme, and b) a second construct said construct comprising an expression construct comprising promoter active in said soybean plants (preferably a ubiquitin promoter as defined above) and operably linked thereto a nucleic acid sequence encoding a dao enzyme.

More preferably, the promoter for said first and said second expression construct are not identical or the same. In the above mentioned constructs comprising two expression cassettes it is preferred that the two promoters active in soybean plants are not identical. Preferably one promoter (e.g., the promoter for expression of the D-alanine and/or D-serine metabolizing enzyme) is an ubiquitin promoter as defined above), while the other promoter is the actin promoter.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Further, the present invention relates to a composition for selection, regeneration, growing, cultivation or maintaining of a transgenic soy bean plant cells, a transgenic soy bean plant tissue, a transgenic soy bean plant organs or a transgenic soy bean plants or a part thereof comprising an effective amount of D-alanine, D-serine, or a derivative thereof allowing for selection of transgenic soy bean plant cells, soy bean plant tissue, soy bean plant organs or soy bean plants or a part thereof and a transgenic soy bean organism, a transgenic soy bean cell, a transgenic cell culture, a transgenic soy bean plant and/or a part thereof as well as to a cell culture comprising one or more embryogenic calli derived from the node located at the first set of leaves, and D-alanine and/or D-serine in a total concentration from around 5 to 10 mM.

The present invention also relates to selection medium comprising a soy bean target tissue and D-alanine and/or D-serine or a derivative thereof in a phytotoxic concentration.

The promoter data showed herein indicate that Parsley Ubiquitin worked well (2% TE) and both ScBV and ScBV with an intron (i.e. p-ScBV-iSuc UDP) worked with similar efficiency, 1.4%. *Glycine max* Ubiquitin showed also good efficiency (construct RLM434; 5% transformation efficiency; only 60 explants). Thus, for example, a strong constitutive promoter is used in combination with dsda or dao1. Strong constitutive promoters are e.g. the Actin2 promoter, the 35S or the 19S promoter as well as the Ubiquitin promoter as described above, e.g. the PcUbi or GmUbi promoter, or p-ScBV or p-ScBV-iSuc UDP promoters. The nos or "super-promoter" may be suitable as well, in particular for some tissue-specific expression. Thus, in one embodiment, the present invention relates to a construct comprising the PcUbi promoter operably linked to the dsda or dao1 gene and/or comprising the p-ScBV or p-ScBV-iSuc UDP promoter operably linked to the dsda or dao1 gene.

Sequences

1. SEQ ID NO: 1 Nucleotide sequence encoding *Escherichia coli* D-serine dehydratase [dsdA]
2. SEQ ID NO: 2 Amino acid sequence encoding *Escherichia coli* D-serine dehydratase [dsdA]
3. SEQ ID NO: 3 Nucleotide sequence encoding *Rhodotorula gracilis* (*Rhodosporidium toruloides*) D-amino acid oxidase
4. SEQ ID NO: 4 Amino acid sequence encoding *Rhodotorula gracilis* (*Rhodosporidium toruloides*) D-amino acid oxidase
5. SEQ ID NO. 5 Nucleotide sequence encoding a *Rhodotorula gracilis* (*Rhodosporidium toruloides*) D-amino acid oxidase codon optimized
6. SEQ ID NO. 6 Amino acid sequence encoding a *Rhodotorula gracilis* (*Rhodosporidium toruloides*) D-amino acid oxidase
7. SEQ ID NO: 7 Parsley (*Petroselinum crispum*) UBI4-2 promoter comprising part of 5'-untranslated region with internal intron (406-993); total length 996 bp.
8. SEQ ID NO: 8 Soybean (*Glycine max*) ubiquitin promoter comprising part of 5'-untranslated region with internal intron (1519-2031); total length 2031 bp.
9. SEQ ID NO: 9 Artificial construct: Bar-Selda Binary Vector RLM407: LB> <p-NOS::c-BAR::t-NOS p-PcUBI4-2:: c-dsdA/na::t-NOS> RB>.
10. SEQ ID NO: 10 Artificial construct: T-DNA insert of RLM274, a RLM407-type Bar-GUS Binary Vector: LB> <p-NOS::c-bar::t-NOS p-PcUBI::c-gusINT::t-NOS> RB>.
11. SEQ ID NO: 11 Artificial construct: T-DNA insert of RLM254, a RLM407-type Selda-GUS Binary Vector: LB> <p-sTPT::c-dsdA/na::t-NOS p-PcUBI::c-gusINT::t-NOS> RB>.
12. SEQ ID NO: 12 Artificial construct: T-DNA insert of REW008, a Bar-GUS Binary Vector: LB> <p-NOS::c-bar::t-NOS p-PcUBI::c-gusINT::t-NOS> RB>.
13. SEQ ID NO: 13 Artificial construct: T-DNA insert of RET063, a RLM407-type Selda-GUS Binary Vector: LB> <p-AtAct2i::c-dsdA/na::t-NOS p-PcUBI::c-gusINT::t-NOS> RB>.
14. SEQ ID NO: 14 Artificial construct: T-DNA insert of RET019, a RLM407-type Selda-GUS Binary Vector: LB> <p-AtAct2i::c-dao1/pa::t-NOS p-PcUBI::c-gusINT::t-NOS> RB>.
15. SEQ ID NO: 15 Artificial construct: T-DNA insert of RET017, a RLM407-type Selda-GUS Binary Vector: LB> <p-NOS:c-dsdA/na::t-NOS p-PcUBI::c-gusINT::t-NOS> RB>.
16. SEQ ID NO: 16 Artificial construct: T-DNA insert of RET015, a RLM407-type Selda-GUS Binary Vector: LB> <p-NOS:c-dao1/ko::t-NOS p-PcUBI::c-gusINT::t-NOS> RB>.
17. SEQ ID NO: 17 *Arabidopsis thaliana* Actin 2 promoter region with first intron (955-1397); total length: 1408 nucleotides.

EXAMPLES

Unless otherwise specified, all chemicals were from Mallinckrodt Baker, Inc. (Phillipsburg, N.J., USA), Phytotechnology Laboratories (Shawnee Mission, Kans., USA), EMD Chemicals, Inc. (Gibbstown, N.J., USA), Alfa Aesar and Sigma (St. Louis, Mo., USA).

A. Stocks Used in the Media:
1. B5 major salts (10× stock)
   a. 0.25 M $KNO_3$ (Potassium nitrate)
   b. 0.01 M $CaCl_2*2H_2O$ (Calcium chloride)
   c. 0.01 M $MgSO_4*7H_2O$ (Magnesium sulfate)
   d. 0.01 M $(NH_4)_2SO_4$ (Ammonium sulfate)
   e. 0.01 M $NaH_2PO_4*H_2O$ (Sodium phosphate)
2. B5 minor salts (100× stock)
   a. 5 mM $H_3BO_3$ (Boric acid)
   b. 10 mM $MnSO_4*H_2O$ (Manganese sulfate)
   c. 0.7 mM $ZnSO_4*7H_2O$ (Zinc sulfate)
   d. 0.45 mM Ki (Potassium iodide)
   e. 0.1 mM $Na_2MoO_4*2H_2O$ (Molybdic acid)
   f. 0.01 mM $CuSO_4*5H_2O$ (Cupric sulfate)
   g. 0.01 mM $COCl_2*6H_2O$ (Cobalt chloride)
3. B5 vitamins (100× stock)
   a. 0.055 M Myo-inositol
   b. 0.8 mM Nicotinic acid
   c. 0.5 mM Pyridoxine-HCl
   d. 3 mM Thiamine-HCl
4. MS major salts (10× stock)
   a. 0.2 M $NH_4NO_3$ (Ammonium nitrate)
   b. 0.2 M $KNO_3$ (Potassium nitrate)
   c. 30 mM $CaCl_2*2H_2O$ (Calcium chloride)
   d. 15 mM $MgSO_4*7H_2O$ (Magnesium sulfate)
   e. 12.5 mM $KH_2PO_4$ (Potassium phosphate)
5. MS minor salts (100× stock)
   a. 10 mM $H_3BO_3$ (Boric acid)
   b. 13 mM $MnSO_4*H_2O$ (Manganese sulfate)
   c. 3 mM $ZnSO_4*7H_2O$ (Zinc sulfate)
   d. 0.5 mM Ki (Potassium iodide)
   e. 0.1 mM $Na_2MoO_4*2H_2O$ (Molybdic acid)
   f. 0.01 mM $CuSO_4*5H_2O$ (Cupric sulfate)

g. 0.01 mM COCl$_2$*6H$_2$O (Cobalt chloride)
6. MSIII Iron (100× stock)
   a. 10 mM FeSO$_4$*7H$_2$O (Ferrous sulfate)
   b. 10 mM C$_{10}$H$_{14}$O$_8$Na$_2$N$_2$*2H$_2$O (NaEDTA)

B. Composition of Media

Unless indicated otherwise below the media can be employed for all three of the preferred explant tissues for the methods of the invention.

1. Germination medium GM (solid) in 25×100 mm Petri dish or Plantcon™ (Sigma) culture boxes:
   a. 1× B5 major salts,
   b. 1× B5 minor salts,
   c. 1×MSIII iron,
   d. 2% Sucrose,
   e. 1× B5 vitamins,
   f. 5 uM BAP (optional),
   g. 0.8% Purified Agar (Sigma);
   h. pH 5.8.
2. YEP medium (solid and liquid) in Erlenmeyer flask or 15×100 mm Petri dishes:
   a. 10 g/L Bacto-peptone (Difco; Becton Dickinson & Co., Cockeysville, Md., USA),
   b. 5 g/L Yeast-extract (Difco),
   c. 5 g/L NaCl,
   d. Appropriate antibiotics for selection,
   e. 1.2% Granulated agar (Difco) solid only;
   f. pH 7.0.
3. Propagation medium MODPROP (solid) in 25×100 mm Petri dish: (METHOD C)
   a. 1×MS major salts,
   b. 1×MS minor salts,
   c. 1×MSIII iron,
   d. 1× B5 vitamins,
   e. 3% Sucrose
   f. 0.22 to 1.12 mg/L (1 μM to 5 μM) BAP (preferably about 1 μM)
   g. 0.8% Purified Agar (Sigma)
   g. pH 5.8
4. Co-cultivation medium CCM (liquid):
   a. ⅒× B5 major salts,
   b. ⅒× B5 minor salts,
   c. ⅒×MSIII iron,
   d. 1× B5 vitamins
   e. 3% Sucrose,
   f. 20 mM 2-[N-morpholino]ethanesulfonic acid (MES; M$_W$=213.26 g/Mol),
   g. 200 μM acetosyringone (AS),
   h. 0.72 μM to 1.44 μM GA$_3$ (Gibberellic acid; M$_w$=346.38 g/Mol)
   i. BAP (6-benzylaminopurine; M$_W$=225.25 g/mol): 7.5 μM.
   j. Method C only: 400 mg/L L-cysteine (3.3 mM) (Sigma)
   k. pH 5.4.
5. Co-cultivation medium CCM (solid) in 15×100 mm Petri dishes:
   a. ⅒× B5 major salts,
   b. ⅒× B5 minor salts,
   c. ⅒×MSIII iron,
   d. 1× B5 vitamins,
   e. 3% Sucrose,
   f. 20 mM 2-[N-morpholino]ethanesulfonic acid (MES)
   g. 200 μM acetosyringone AS,
   h. 0.72 μM to 1.44 μM GA$_3$ (Gibberellic acid; M$_w$=346.38 g/Mol)
   i. BAP (6-benzylaminopurine; M$_W$=225.25 g/mol): 7.5 μM.
   j. Thiol compounds,
      (i). 100 to 1000 g/L L-cysteine (M$_W$=121.16 g/Mol; Sigma); preferably: Method B and C: 400 mg/L L-cysteine (3.3 mM); Method A: 1 g/l (8.25 mM) L-cysteine
      (ii). 0 to 1 mM or 154.2 mg/L DTT (Fisher Scientific, Fair Lawn, N.J., USA),
      (iii). 0 to 1 mM sodium thiolsulfate anhydrous (158.1 mg/L) or sodium thiolsulfate pentahydrate 245 mg/L (Mallinckrodt, Paris, Ky., USA), Method A: 1 mM dithiothreitol, 1 mM sodium thiosulfate
   k. 0.5% Purified Agar;
   l. pH 5.4.
6. Washing medium Modwash (liquid):
   a. 1× B5 major salts,
   b. 1× B5 minor salts,
   c. 1×MSIII iron,
   d. 3% Sucrose,
   e. 1× B5 vitamins
   f. 30 mM MES,
   g. 350 mg/L Timentin™
   h. pH 5.6
6. Shoot induction medium SIM (liquid):
   a. 1× B5 major salts,
   b. 1× B5 minor salts,
   c. 1×MSIII iron,
   d. 1× B5 vitamins,
   e. 3% Sucrose,
   f. 3 mM MES,
   g. 1 μM to 7.5 μM (preferably 1 μM) BAP
   h. 250 mg/L Timentin™
   i. 0.8% Purified Agar;
   j. pH 5.6.
5. Shoot induction medium SIM (solid) in 20×100 mm Petri dishes:
   a. 1× B5 major salts,
   b. 1× B5 minor salts,
   c. 1×MSIII iron,
   d. 1× B5 vitamins,
   e. 3% Sucrose,
   f. 3 mM MES,
   g. 1 μM to 7.5 μM (preferably about 1 μM) BAP.
   h. 5 μM Kinetin
   i. 250 mg/L Timentin™
   j. Selection compound when appropriate,
   k. 0.8% Purified Agar;
   l. pH 5.6.
7. Shoot elongation medium SEM (solid) in 20×100 mm Petri dishes:
   a. 1×MS major salts,
   b. 1×MS minor salts,
   c. 1×MSIII iron,
   d. 1× B5 vitamins,
   e. 3% Sucrose,
   f. 3 mM MES,
   g. 50 mg/L L-asparagine (0.378 mM),
   h. 100 mg/L L-pyroglutamic acid (0.775 mM),
   i. 0.1 mg/L IAA (0.57 μM),
   j. 0.5 mg/L GA3 (1.44 μM),
   k. 1 mg/L trans-zeatin riboside (2.85 μM),
   l. 250 mg/L Timentin™
   m. Selection compound when appropriate,
   n. 0.8% Purified Agar;
   o. pH 5.6.
7. Rooting medium RM (solid) in 25×100 mm Petri dish or Plantcon™ (Sigma) culture boxes:
   a. ½× B5 major salts,
   b. ½× B5 minor salts,
   c. 1×MSIII iron, d. 2% sucrose,
e. 3 mM MES,
f. 1 mg/L (5 µM) Indole-butyric acid (IBA, $M_w$=203.24 g/Mol)
g. g. 0.8% Purified Agar; Method C only: 250 mg/L Timentin
h. pH 5.6.

Example 1

Sterilization and Germination of Soybean Seeds

Virtually any seed of any soybean variety can be employed in the method of the invention. A variety of soybean cultivar (including Jack, Williams 82, and Resnik) is appropriate for soybean transformation. Soybean seeds are sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds are removed and approximately 18 to 20 seeds are plated on solid GM medium with or without 5 µM 6-benzyl-aminopurine (BAP) in 25×100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µM/m2 s) at 25° C. are used for explant material for the three-explant types. At this time, the seed coat has split, and the epicotyl with the unifoliate leaves has grown to, at minimum, the length of the cotyledons. The epicotyl should be at least 0.5 cm to avoid the cotyledonary-node tissue (since soybean cultivars and seed lots may vary in the developmental time a description of the germination stage is more accurate than a specific germination time).

Example 2

Growth and Preparation of *Agrobacterium* Culture

*Agrobacterium* cultures are prepared by streaking *Agrobacterium* (e.g., *A. tumefaciens* or *A. rhizogenes*) carrying the desired binary vector onto solid YEP growth medium and incubating at 25° C. until colonies appear (about 2 days). Depending on the selectable marker genes present on the Ti or Ri plasmid, the binary vector, and the bacterial chromosomes, different selection compounds will be used for *A. tumefaciens* and rhizogenes selection in the YEP solid and liquid media. Various *Agrobacterium* strains can be used for the transformation method After approximately two days, a single colony (with a sterile toothpick) is picked and 50 ml of liquid YEP is inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP are inoculated with 5 µl to 3 ml of working *Agrobacterium* stock in a 500 ml Erlenmeyer flask. Shake the flask overnight at 25° C. until the $OD_{600}$ is between 0.8 and 1.0. Before preparing the soybean explants, pellet the Agrobacteria by centrifugation for 10 min at 5,500×g at 20° C. Resuspend the pellet in liquid CCM to the desired density ($OD_{600}$ 0.5-2.0) and place at room temperature at least 30 min before use.

Example 3

Explant Preparation and Co-Cultivation (Inoculation)

Seedlings at this time have elongated epicotyls from at least 0.5 cm but generally between 0.5 and 2 cm. Elongated epicotyls up to 4 cm in length have been successfully employed. Explants are then prepared with:
i) with or without some roots,
ii) with a partial, one or both cotyledons, all preformed leaves are removed including apical meristem, and the node located at the first set of leaves is injured with several cuts using a sharp scalpel.

This cutting at the node not only induces *Agrobacterium* infection but also distributes the axillary meristem cells and damages pre-formed shoots. After wounding and preparation, the explants are set aside in a Petri dish and subsequently co-cultivated with the liquid CCM/*Agrobacterium* mixture for 30 minutes. The explants are then removed from the liquid medium and plated on top of a sterile filter paper on 15×100 mm Petri plates with solid co-cultivation medium. The wounded target tissues are placed such that they are in direct contact with the medium.

Example 4

Shoot Induction

After 3 to 5 days co-cultivation in the dark at 25° C., the explants are rinsed in liquid SIM medium (to remove excess *Agrobacterium*) before placing on the solid SIM medium. Approximately 5 explants are placed such that the target tissue is in direct contact with the medium. During the first 2 weeks, the explants can be cultured with or without selective medium. Preferably, explants are transferred onto SIM without selection for one week.

Wrap plates with 3M micropore tape (3M, St. Paul, Minn., USA) and place in a growth chamber for two weeks with a temperature averaging 25° C. under 18 h light/6 h dark cycle at 70-100 µE/m² s. Various light intensities and wavelengths, selection regimes, and SIM have been tested for this explant. The explants will remain on the SIM medium with or without selection until de novo shoot growth occurs at the target area (e.g., axillary meristems at the first node above the epicotyl). Transfers to fresh medium can occur during this time. Explants are transferred from the SIM with or without selection to SIM with selection after about one week. At this time, there is considerable de novo shoot development at the primary node for seedling explants.

Preferably, all shoots formed before transformation will be removed up to 2 weeks after co-cultivation to stimulate new growth from the meristems. This helps to reduce chimerism in the primary transformant and increase amplification of transgenic meristematic cells. During this time the explant may or may not be cut into smaller pieces (i.e. detaching the node from the explant by cutting the epicotyl).

Example 5

Shoot Elongation

After 2 to 4 weeks (or until a mass of shoots has formed) on SIM medium (preferably with selection), the explants will be transferred to SEM medium that will stimulate shoot elongation of the shoot primordia. This medium may or may not contain a selection compound.

After every 2 to 3 weeks, transfer the explants to fresh SEM medium (preferably containing selection) after carefully removing dead tissue. The explants should hold together and not fragment into pieces and retain somewhat healthy. The explants will continue to be transferred until the explant dies or shoots elongate. Elongated shoots >3 cm are removed and placed into RM medium for about 1 week at which time roots begin to form. In the case of explants with roots, they are transferred directly into soil. Rooted shoots are transferred to soil and hardened in a growth chamber for 2 to 3 weeks before transferring to the greenhouse. Regenerated plants obtained using this method are fertile and have produced on average 500 seeds per plant.

Transient GUS expression after 5 days of co-cultivation with Agrobacterium tumefaciens is widespread on the seedling axillary meristem explants especially in the regions wounding during explant preparation. Explants were placed into shoot induction medium without selection to see how the primary-node responds to shoot induction and regeneration. Thus far, greater than 70% of the explants have formed new shoots at this region. Expression of the GUS gene is stable after 14 days on SIM, implying integration of the T-DNA into the soybean genome. In addition, preliminary experiments have resulted in the formation of GUS positive shoots forming after 3 weeks on SIM.

Example 6

Killing Curve on Non-Inoculated Seedling Axillary Meristem Explant

Figure 1:
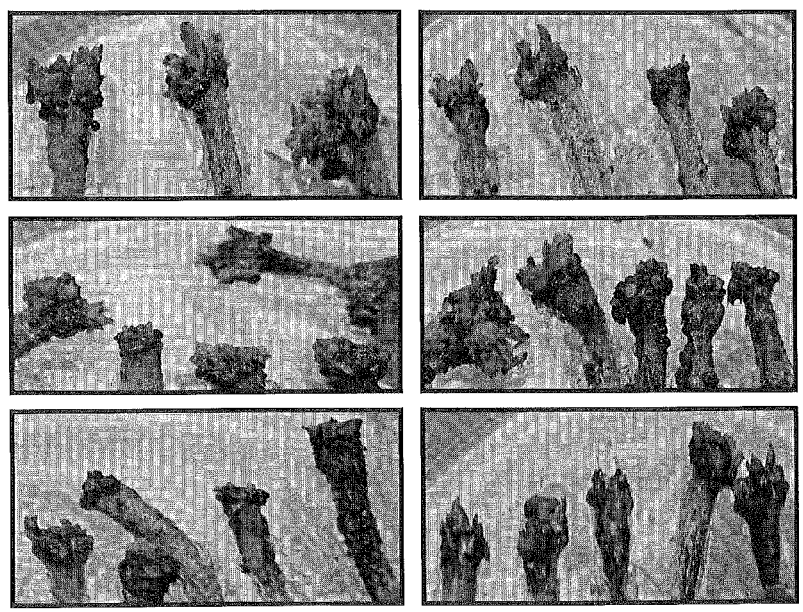
FIG. 1 Shoot induction at 3 weeks on D-Serine.

Killing curves for D-serine toxicity on non-Agrobacterium infected soybean tissues were performed on axillary meristem explants. Thirty explants were prepared as described above in example 1 and cultured on SIM containing either 0 mM, 3 μM, 30 μM, 300 μM, 3 mM, 30 mM, or 60 mM D-serine for a total of 4 weeks. After this time, the percent of explants with new shoot primordia, i.e. appearance of multiple shoots, were counted. In this experiment, a reduction in regeneration occurred between 3 and 30 mM and only 30% regeneration on explants exposed to 60 mM D-serine was seen (FIG. 1).

Example 7

Figure 2:
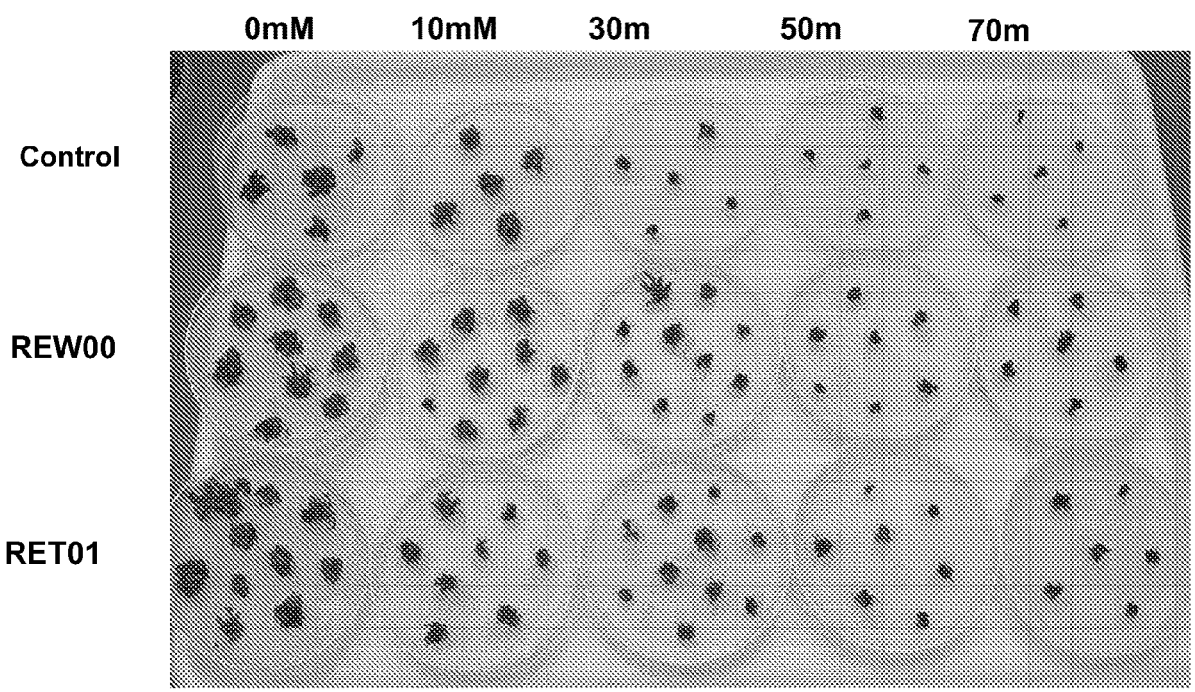

Killing Curve for D-Serine on Agrobacterium-Inoculated Seedling Axillary Meristem Explants Killing curves for D-serine selection seedling axillary meristem (SAM) for 3 soybean cultivars were performed with and without Agrobacterium infection at shoot induction level. For each cultivar, 10 explants were cut and inoculated with A. tumefaciens strain AGL1/pREW008 (no dsdAgene control), 10 explants inoculated with AGL1/pRET017 (nosP-dsda-nosT), and 5 explants were uninoculated. After co-cultivation, the SAM explants were transferred onto shoot induction media with 0, 10, 30, 50, or 70 mM D-serine. The survival of the explants after 4 weeks on shoot induction was noted and the appropriate selection levels of D-serine were found to be between 30 and 50 mM (FIG. 2).

Example 8a

Establishing Kill Curve with D-Serine on Inoculated Axillary Meristem Explants

In order to establish an effective level of selection during shoot induction and elongation a broad range of D-Serine concentrations was initially explored. Soybean axillary meristem explants were prepared from 7 day-old-seedlings from the Dairyland cultivar 98043, as described above in Examples 1 and 3.

Agrobacterium rhizogenes strain SHA017 with the Super Vir pSB1 plasmid and containing the binary plasmids pRET017 or pREW008 were prepared as described in example 2. pRET017 contains nosP-c-dsdA/na-nosT and pPcUBI-gusINT-nosT (Example 9). pREW008 contains nosP-bar-nosT and pPcUBI-gusINT-nosT and was used as a control vector (Example 9).

Explants were handled as described above in example 4. After one week on shoot induction medium (SIM) medium with no selection, explants were transferred to SIM medium containing various concentrations of D-serine ranging from 0 to 15 to 30 to 45 mM. All regenerating explants (shoot pads) were transferred to shoot elongation media (SEM) containing 3 mM D-serine after three and six weeks of incubation. Elongating shoots were transferred to rooting medium (RM) medium and screened by GUS expression and Taqman analysis.

TABLE 1

Percent of explants per construct regenerating on various D-serine concentrations after 3 weeks in shoot induction (SIM) medium.

| | D-Ser in SIM: | | | |
|---|---|---|---|---|
| | 0 mM | 15 mM | 30 mM | 45 mM |
| REW008 | 79.0 | 76.9 | 55.3 | 21.9 |
| RET017 | 74.4 | 78.1 | 61.2 | 25.5 |

TABLE 2

Percent of explants per construct surviving after three weeks in shoot elongation (SEM) + 3 mM D-serine.

| | D-Ser in SIM: | | | |
|---|---|---|---|---|
| | 0 mM | 15 mM | 30 mM | 45 mM |
| REW008 | 94.7 | 72.1 | 34.5 | 2.6 |
| RET017 | 82.8 | 74.1 | 33.6 | 4.9 |

Increasing levels of D-serine in shoot induction medium decreased the percentage of explants that regenerated and formed shoot pads (FIG. 3). The size of the shoot-pads that formed decreased as levels of D-serine increased. Additionally, formation of a brown friable callus increased with increasing D-serine concentrations. Little difference was observed in shoot-pad morphology between the dsdA-containing (RET017) and control (REW008) constructs during shoot induction (FIG. 3). There was no shoot elongation at 3 mM D-Ser on those explants coming from 30 or 45 mM D-Ser during shoot induction. Few shoots elongated from those explants that were exposed to 15 mM D-Ser during shoot induction (data not shown). GUS assays conducted throughout the experiments showed GUS positive sectors in the shoot pads produced after 3 weeks in shoot induction media from both pRET017 and pREW008. GUS assays and Taqman (uidA and dsdA) analysis were all negative on the few elongated shoots that formed at 15 mM D-Serine during shoot induction and were transferred to 3 mM D-Serine at shoot elongation. No elongated shoots were observed after incubation at higher concentrations than 15 mM D-Serine during shoot induction.

Example 8b

D-Alanine and D-Alanine/D-Serine Killing Curves Using Primary Node Explants

Kill curves for D-alanine selection with and without 7.5 mM D-serine were conducted for future experiments using dao1 as a selectable marker gene. The combination of using D-alanine and D-serine was also performed for the dao1 gene which can metabolize both D-alanine and D-serine. The binary plasmids RET019 (Pactin-dao1, Pubi-gus) and REW008 (Pnos-bar, Pubi-gus) were used as a positive and a negative control, respectively, and the T-DNA mobilized into soybean using *Agrobacterium rhizogenes* strain SHA017pSB1.

Explants were inoculated with *Agrobacterium*, co-cultivated for 5 days, then moved onto shoot induction medium with or without selection for one week. After that time, explants were transferred onto new SIM with selection.

In experiment 1, D-alanine was added to the SIM medium at the following concentrations: 0, 3, 7.5, 10, 20, 30, and 50 mM.

In experiment 2, D-alanine was added in the same concentrations with 7.5 mM D-serine.

The experimental design was as follows: T(treatment)1: 7 explants inoculated with REW008 with 1 week recovery; T2: 7 explants inoculated with REW008 with no recovery; The results of the experiment are shown in Table 2b. The regeneration frequency does not drop below 70% until the explants were exposed to 30 mM D-alanine immediately after co-cultivation. This drop was not seen on explants with recovery until 20 mM D-alanine. When in combination with D-serine, the explants do have reduced regeneration at lower concentrations, between 7.5 and 10 mM.

TABLE 2b

Results of D-alanine kill curve based on regeneration after 3 weeks on SIM with corresponding treatment.

| T | 0 mM | 3 mM | 7.5 mM | 10 mM | 20 mM | 30 mM | 50 mM |
|---|---|---|---|---|---|---|---|
| Experiment 1: D-alanine Kill Curve-regeneration (%) after 3 weeks on SIM | | | | | | | |
| T1 | 100 | 100 | 100 | 100 | 100 | 29 | 0 |
| T2 | 100 | 71 | 86 | 71 | 27 | 0 | 0 |
| Experiment 2: D-alanine + 7.5 mM D-serine Kill Curve-regeneration (%) after 3 weeks on SIM | | | | | | | |
| T1 | 100 | 100 | 100 | 71 | 57 | 0 | 0 |
| T2 | 100 | 100 | 71 | 57 | 0 | 14 | 0 |

Example 9

Transformation Vectors Used for Evaluating dsdA and dao1 Genes

Several transformation vectors were made containing either dsdA or dao1 gene. A construct comprising the bar selection marker was used as a control in the transformation experiments (Table 3). Most vectors were developed using the pSUN3 binary vector as background with the exception of pLM407 and pLM274 that have a Gateway background (Table 3). The DSDA protein uses the D-Serine only as the substrate, in contrast to the DAO1 protein that enzymatically oxidizes a broader range of D-Amino acids, e.g. D-Ser and D-Ala.

TABLE 3

Description of transformation vectors used for the experiments in establishing transformation with dsdA and dao1 genes as the selection marker.

| Vector | SEQ ID NO: | LB-Selection marker | Reporter/Selection marker-RB |
|---|---|---|---|
| pRET017 | 15 | p-Nos::EcdsdA::t-NOS | p-PcUbi4-2::gusINT::t-NOS |
| pRLM407 | 9 | p-PcUbi4-2::EcdsdA::t-OCS | p-Nos::bar::t-NOS |
| pRET063 | 13 | p-AtAct::EcdsdA::t-OCS | p-PcUbi4-2::gusINT::t-NOS |
| pET019 | 14 | p-AtAct::dao1/ko::t-OCS | p-PcUbi4-2::gusINT::t-NOS |
| RET015 | 16 | p-Nos::dao1/ko | p-PcUbi4-2::gusINT::t-NOS |
| pLM254 | 11 | p-STPT::EcdsdA::t-OCS | p-PcUbi4-2::gusINT::t-NOS |
| pLM274 | 10 | p-Nos::bar::t-NOS | p-PcUbi4-2::gusINT::t-NOS |
| pREW008 | 12 | p-Nos::bar::t-NOS | p-PcUbi4-2::gusINT::t-NOS | pRLM274 control for pRLM407 (gateway background) and pREW008 control for all remaining constructs (pSUN 3 background)
EcdsdA = *E. coli*
dsdA; dao1 = D-Amino acid oxidase gene;
bar = phosphinothricin acetyltransferase;
p-PcUbi4-2 = Parsley ubi promoter;
STPT = Triose phosphate translocator from *Arabidopsis*;
pNos = Nopaline synthase promoter;
p-AtACT = *Arabidopsis thaliana* actin promoter;
t-OCS3' = OCS3' terminator;
t-NOS = nos terminator.

Example 10a

Effect of D-Serine Selection when Using the dsdA or dao1 Genes Under Different Promoters Soybean axillary meristem explants were prepared from 7 day-old-seedlings from the Dairyland cultivar 93061, as described above in Examples 1 and 3. *Agrobacterium rhizogenes* strain SHA017 with the Super Vir pSB1 plasmid and containing the binary plasmids described in Table 3 were prepared as described in example 2.

Explants were handled as described in Example 4. After one week on shoot induction medium (SIM) with no selection, explants were transferred to SIM containing 7.5 mM D-serine. All regenerating explants (shoot pads) were transferred to shoot elongation media (SEM) containing 5 mM D-serine after three and six weeks of incubation. Elongating shoots were transferred to rooting medium (RM) medium and screened by GUS expression and/or Taqman analysis.

As described in Table 4 the Parsley ubiquitin promoter works more effectively to drive the expression of the dsdA gene. It is known that the Parsley ubiquitin promoter is a highly constitutive promoter in soybean axillary seedlings based on gene expression analysis of the uidA reporter gene. The *Arabidopsis* actin promoter was also able to confer resistant levels of expression to soybean cells when using the dsdA gene but at a significantly lower efficiency than the Parsley ubiquitin promoter (Table 4). No transgenic shoots have been obtained when using the dsdA gene under the control of the NOS or STPT promoters. The *Arabidopsis* actin and NOS promoters were able to confer resistant levels to soybean cells when using the dao1/ko gene. In this case the combination of NOS promoter and the dao1/ko gene seems to have two-fold greater efficiency when compared to AtActin::dao1/ko.

TABLE 4

Summary of transformation experiments conducted on evaluating constructs with different promoters driving dsdA and dao1 genes under D-Serine selection.

| Vector | SEQ ID NO: | Marker description | # explants | # elongated shoots | # of positive shoots* |
|---|---|---|---|---|---|
| RET017 | 15 | p-Nos::EcdsdA | 455 | 17 | 0 |
| RLM407 | 9 | p-PcUbi4-2::EcdsdA | 672 | 38 | 24 |
| RET063 | 13 | p-AtAct::EcdsdA | 268 | 29 | 1 |
| RET019 | 14 | p-AtAct::dao1/ko | 597 | 58 | 4 |
| RLM254 | 11 | p-STPT::EcdsdA | 306 | 44 | 0 |
| RET015 | 16 | p-Nos::dao1/ko | 284 | N/A | 4 |
| REW008 | 12 | p-Nos::bar | 426 | 5 | 0 |
| RLM274 | 10 | p-Nos::bar | 228 | 0 | 0 |

*Positive shoots based on GUS or dsdA Taqman analysis.
RLM274 control for RLM407 (gateway background) and REW008 control for all remaining constructs (pSUN 3 background)

It appears that soybean requires a highly constitutive promoter to select transgenic plants with the dsdA selection system. The use of the Parsley ubiquitin promoter results in a consistently higher transformation efficiency than other promoters normally used in dicot plants, such as the *Arabidopsis thaliana* Actin or the STP promoters. In comparison with these promoters, transformation efficiency with the Parsley ubiquitin promoter was significantly higher. It is known that optimal selection needs expression of the selection marker in the relevant cells of the target tissue (which later dedifferentiate and regenerate into the transgenic plants), at the right time and the right concentration.

Example 10b

SELDA Selection and Promoter-dsda Combinations

The effect of the promoter driving the dsda gene on transformation efficiency was tested in the transformation protocol. An experiment with 6 repetitions over time (cutting experiments with 2 researchers) was completed with 4 promoter-dsda combinations (treatments), RLM407, RLM431, RLM432, RLM433, and a minimum of 50 explants per treatment (Table 4a). In 2 of the repetitions, RLM254 was included, and in one repetition, RLM434 was included. The explants were prepared and randomly divided into one of the 6 treatments (plasmids carried in *A. rhizogenes* strain SHA017/pSB1) for 30 minutes. After inoculation, the explants were co-cultivated for 5 days in the dark on solid co-cultivation medium containing 5 µM kinetin. The protocol was followed as stated above with the D-serine selection regime: one week on shoot induction without selection, 3 weeks on shoot induction medium with 7.5 mM D-serine, then 5 mM D-serine throughout shoot elongation. Only one shoot per explant was removed to eliminate regeneration of clones. Putative transformants were confirmed for the presence of the dsda gene using quantitative PCR (TaqMan) and the transformation efficiency (TE) was calculated using the formula: [(number of dsda positive TaqMan confirmed independent events/total number of explants inoculated (n))*100].

Transgenic events were recovered from all promoter-dsda combinations tested (Table 4b). The constructs containing the ubiquitin-dsda combinations, RLM407 and RLM434, gave the highest transformation efficiencies in this study.

TABLE 4a

Promoters used for driving dsda gene in 6 constructs.

| | Seq ID No: | Promoter::Ecdsda |
|---|---|---|
| RLM407 | 9 | p-PcUbi |
| RLM431 | | p-ScBV-iSuc UDP |
| RLM432 | | p-ScBV |
| RLM433 | | p-STPT (3 bp) |
| RLM254 | 11 | p-STPT |
| RLM434 | | p-GmUbi |

TABLE 4b

Transformation efficiencies for explants inoculated with different promoter-dsda combinations and D-serine selection.

| Construct | Number of explants (n) | Confirmed events | Ave TE (%) | TE range (%) |
|---|---|---|---|---|
| RLM407 | 702 | 15 | 2 | 0.8-4.4 |
| RLM431 | 478 | 7 | 1.4 | 0-6.67 |
| RLM432 | 467 | 7 | 1.4 | 0-3.33 |
| RLM433 | 470 | 2 | 0.3 | 0-0.9 |
| RLM254 | 106 | 1 | 0.8 | 0-1.7 |
| RLM434 | 60 | 3 | 5 | — |

Example 11

Comparison of Two Selectable Markers: dsdA and Bar

Transformation experiments were conducted to compare transformation efficiencies with two selection systems, i.e dsdA/D-Serine, bar/phosphinothricin (Table 5). Binary vector LM407 carries both selectable markers, dsdA and bar under pPcUbi and pNos promoters respectively. Vector LM274 harbors the bar gene under the control of the pNos promoter and it has been successfully used with the soybean axillary transformation method in conjunction with phosphinothricin selection.

Soybean axillary meristem explants were prepared from 7 day-old-seedlings from the Dairyland cultivar 93061, as described above in Examples 1 and 3.

*Agrobacterium rhizogenes* strain SHA017 with the Super Vir pSB1 plasmid and containing the binary plasmids described in Table 3 were prepared as described in example 2.

Explants were handled as described in Example 4. After one week on shoot induction medium (SIM) with no selection, explants were transferred to SIM containing 7.5 mM D-Serine or 3 mg/l phosphinothricin. All regenerating explants (shoot pads) were transferred to shoot elongation media (SEM) containing 5 mM D-serine or 5 mg/l phosphinothricin after three weeks of incubation in SIM. Elongating shoots were transferred to rooting medium (RM) medium and screened by Taqman analysis.

TABLE 5

Comparison on evaluating two constructs and two selection systems.

| Vector | Marker description | Explants infected | Selection | Independent + elongated shoots | Independent events in GH | TE (%) |
|---|---|---|---|---|---|---|
| pRLM407 (SEQ ID NO: 9) | p-PcUbi4-2::EcdsdA/ pNos::bar | 220 | D-Serine | 10 | 8 | 3.6 |
| pRLM407 | p-PcUbi4-2::EcdsdA/ pNos::bar | 170 | PPT | 5 | 2 | 1.2 |

A two-fold increase transformation efficiency was obtained when using the same construct pRLM407 with D-Serine selection. However, it is worth mentioning that this represents a small size number of explants that were used for transformation.

Example 11

SELDA Selection and Co-Cultivation Hormones

In the first experiment, the experimental design included 10 repetitions over time (cutting experiments by 3 researchers) with 4 different co-cultivation media (treatments) per repetition and a minimum of 50 explants per treatment. Solid co-cultivation was prepared as stated earlier except the hormone, BAP, was replaced with one of the 4 following hormones: 7.5 μM BAP, 1.0 μM kinetin, 5.0 μM kinetin, or 7.5 μM kinetin. In the second experiment, the experimental design included 3 repetitions over time (cutting experiments by 1 researcher) with 5 different co-cultivation media (treatments) per repetition and a minimum of 50 explants per treatment. Solid co-cultivation was prepared by replacing BAP with one of the 5 following hormones: 7.5 μM BAP, 1.0 μM kinetin, 3 μM kinetin, 5 μM kinetin, or 7 μM kinetin.

For both experiments, explants were prepared, inoculated with 50 mL of liquid co-cultivation medium containing SHA017/pSB1 carrying vector RLM407 for 30 minutes, and then randomly placed onto 1 of 4 or 5 solid co-cultivation media treatments, respectively. The protocol was followed as stated above with the D-serine selection regime: one week on shoot induction without selection, 3 weeks on shoot induction medium with 7.5 mM D-serine, then 5 mM D-serine throughout shoot elongation. Only one shoot per explant was removed to eliminate regeneration of clones. Putative transformants were confirmed for the presence of the dsda gene using quantitative PCR (TaqMan) and the transformation efficiency (TE) was calculated using the formula: [(number of dsda positive TaqMan confirmed independent events/total number of explants inoculated (n))*100].

In both experiments, transgenic events were recovered from all treatments tested (Table 6 and 7). In addition, the presence of kinetin in the co-cultivation media resulted in higher average transformation efficiencies than when explants were co-cultivated in the presence of BAP.

TABLE 6

Transformation efficiency of explants co-cultivated on co-cultivation media containing 4 different hormone regimes.

| | Number of explants (n) | Confirmed events | Ave TE (%) | TE range (%) |
|---|---|---|---|---|
| 7.5 uM BAP | 761 | 3 | 0.4 | 0-2.5 |
| 1 uM Kinetin | 728 | 10 | 1.4 | 0-6.4 |
| 5 uM Kinetin | 481 | 9 | 2.3 | 0-4.2 |
| 7.5 uM Kinetin | 825 | 19 | 2.7 | 0-9.8 |

TABLE 7

Transformation efficiency of explants co-cultivated on co-cultivation media containing 5 different hormone regimes.

| | Number of explants (n) | Confirmed events | Ave TE (%) | TE range (%) |
|---|---|---|---|---|
| 7.5 uM BAP | 227 | 3 | 1.3 | 0-2.5 |
| 1 uM Kinetin | 207 | 8 | 3.7 | 1.3-8.1 |
| 3 uM Kinetin | 238 | 6 | 2.5 | 2.3-2.7 |
| 5 uM Kinetin | 228 | 4 | 1.8 | 1.2-3 |
| 7 uM Kinetin | 231 | 5 | 2.2 | 0-5.2 |

REFERENCES

1. An et al. Plant J 1996 10(1):107-121
2. Ausubel F M et al. (1987) Current Protocols in Molecular Biology, Greene Publishing Assoc. and Wiley Interscience
3. Baker et al. (1987) EMBO J 6: 1547-1554
4. Ball. J. B. and Alewood, P. F. (1990) J. Mol. Recognition 3:55
5. Bäumlein et al. (1991a) Mol Gen Genet 225(3):459-467
6. Bäumlein et al. (1991b) Mol Gen Genet 225:121-128;
7. Bechtold, et al. (1998) Meth. Mol. Biol. 82, 259-266
8. Becker et al. (1992) Plant Mol. Biol. 20: 49
9. Becker et al. (1994) Plant J. 5: 299-307
10. Benfey et al. (1989) EMBO J 8:2195-2202
11. Bevan et al. (1984) Nucl Acid Res 12, 8711-8720
12. Broothaerts W et al. (2005) Nature 433:629-633
13. Bustos et al. (1989) Plant Cell 1(9):839-53
14. Callis et al. (1990) J Biol Chem 265(21):12486-12493
15. Callis et al., "Ubiquitin and Ubiquitin Genes in Higher Plants," Oxford Surveys of Plant Molecular & Cell Biology, vol. 6, pp. 1-30 (1989)
16. Chui et al. (1996) Curr Biol 6:325-330
17. Crameri et al. (1997) Nature Biotech. 15:436
18. Crameri et al., Nature, 391:288 (1998)
19. Cushman et al. (2000) Curr Opin Plant Biol 3(2):117-24
20. Dale & Ow (1991) Proc Nat'l Acad Sci USA 88:10558-10562
21. Dandekar et al. (1989) J Tissue Cult Meth 12:145
22. de Block et al. (1987) EMBO J 6:2513-2518
23. de Bruijn et al. (1996) Rep-PCR Genomic Fingerprinting of Plant-Associated Bacteria and Computer-Assisted Phylogenetic Analyses In: Biology of Plant-Microbe Interaction; Proceedings of the 8th International Congress of Molecular Plant-Microbe Interactions (G. Stacey, B. Mullin and P. Gresshoff, Eds.) APS Press, 497-502
24. Deblaere et al. (1985) Nucl Acids Res 13:4777-4788
25. Della-Cioppa et al. (1987) Plant Physiology 84:965-968
26. Della-Cioppa et al. Bio/Technology 5:579-584 (1987)
27. Dixon M & Kleppe *Biochim. Biophys. Acta* 96 (1965c) 383-389
28. Dixon M & Kleppe K *Biochim. Biophys. Acta* 96 (1965b) 368-382
29. Dixon M & Kleppe K. *Biochim. Biophys. Acta* 96 (1965a) 357-367
30. Dunwell J M (2000) J Exp Bot 51 Spec No: 487-96
31. Ebinuma et al. (2000a) Proc Natl Acad Sci USA 94:2117-2121
32. Ebinuma et al. (2000b) Selection of Marker-free transgenic plants using the oncogenes (ipt, rol A, B, C) of *Agrobacterium* as selectable markers, In Molecular Biology of Woody Plants. Kluwer Academic Publishers)
33. Eichholtz et al. (1987) Somatic Cell and Molecular Genetics 13: 67-76
34. EP-A 0 120 516
35. EP-A 0 175 966
36. EP-A 0 270 356
37. EP-A 0 290 395
38. EP-A 0 331 083
39. EP-A 0 333 033
40. EP-A0 335 528
41. EP-A 0 434 616
42. EP-A 0 444 882
43. EP-A 0 601 092
44. Erikson et al. (2004) Nature Biotechnology 22: 455-458
45. Farmer, P. S. in Drug Design (E. J. Ariens, ed.) Academic Press, New York, 1980, vol. 10, pp. 119-143
46. Farrand et al. (2003) Int. J. Systematic & Evolutionary Microbiology 53:1681-1687
47. Finer and McMullen (1991) In Vitro Cell Dev Biol 27P: 175-182
48. Fire A. et al (1998) Nature 391:806-811
49. Fraley et al. Proc Natl Acad Sci USA 80: 4803 (1983)
50. Franck et al. (1980) Cell 21:285-294;
51. Freeman et al. (1984) Plant Cell Physiol 2 9:1353
52. Freidinger, R. M. (1989) Trends Pharmacol. Sci. 10:270
53. Fromm et al. (1985) Proc Natl Acad Sci USA 82:5824
54. Gabler M et al. (2000) *Enzyme Microb. Techno.* 27, 605-611
55. Gallie et al. (1987) Nucl Acids Res 15:8693-8711
56. Garbarino et al. (1992) Plant Mol Biol 20:235-244
57. Gardner et al. (1986) Plant Mol Biol 6:221-228
58. Gatz et al. (1991) Mol Gen Genetics 227:229-237
59. Gatz et al. (1992) Plant J 2:397-404
60. Gatz et al. (1994) Mol Gen Genetics 243:32-38
61. Gatz et al. (1997) Annu Rev Plant Physiol Plant Mol Biol 48:89-108
62. Gelvin et al. (Eds) (1990) Plant Molecular Biology Manual; Kluwer Academic Publisher, Dordrecht, The Netherlands
63. Genschick et al. (1994) Gene, 148:195-202
64. Goeddel; Gene Expression Technology: Methods in Enzymology 185, Academic Press, San Diego, Calif. (1990)
65. Green et al. (1987) Plant Tissue and Cell Culture, Academic Press
66. Gruber et al. (1993) "Vectors for Plant Transformation," in METHODS IN PLANT MOLECULAR BIOLOGY AND BIOTECHNOLOGY; CRC Press, Boca Raton, Fla., eds.: Glick and Thompson, Chapter 7, pp. 89-119.
67. Hajdukiewicz et al. (1994) Plant Mol Biol 25:989-994
68. Haseloff et al. (1997) Proc Natl Acad Sci USA 94(6): 2122-2127
69. Henikoff & Henikoff, Proc. Natl. Acad. Sci. USA, 89:10915 (1989).
70. Hershey et al. (1991) Mol Gen Genetics 227:229-237
71. Higo et al. (1999) Nucl Acids Res 27(1): 297-300
72. Hinchee et al. (1988) Bio/Technology 6:915-922
73. Hirschman, R., et al. (1993) J. Am. Chem. Soc. 115: 12550-12568
74. Hoekema (1985) In: The Binary Plant Vector System, Offsetdrukkerij Kanters B. V., Alblasserdam, Chapter V
75. Hoekema et al. (1983) Nature 303:179-181
76. Hoffman et al. (1991) Mol Biol 17:1189-1201
77. Holsters et al. (1978) Mol Gen Genet 163:181-187
78. Holtorf S et al. (1995) Plant Mol Biol 29: 637-747
79. Hood et al. (1986) J Bacteriol 168:1291-1301
80. Hooykaas P J J et al. (1977) J Gen Microbiol 98:477-484
81. Jefferson (1987b) Plant Mol. Bio. Rep., 5:387-405
82. Jefferson et al. (1987a) EMBO J 6:3901-3907
83. Joseffson et al. (1987) J Biol Chem 262:12196-12201
84. Kado (1991) Crit Rev Plant Sci 10:1
85. Karlin and Altschul, Proc. Natl. Acad Sci. USA, 87:2264 (1990).
86. Karlin and Altschul, Proc. Natl. Acad. Sci. USA, 90:5873 (1993).
87. Kawalleck et al. (1993) Mol Biol 21:673-684
88. Kilby N J et al. (1995) Plant J 8:637-652
89. Klapwijk et al. (1980) J. Bacteriol., 141, 128-136
90. Klein & Klein (1953) J Bacteriol. 66 (2): 220-228;
91. Klein et al. (1987) Nature 327:70-73
92. Koncz & Schell (1986) Mol Gen Genet 204:383-396
93. Koprek et al. (1999) Plant J 19: 719-726
94. Laboratory guide for identification of plant pathogenic bacteria, 3rd edition. (2001) Schaad, Jones, and Chun (eds.) ISBN 0890542635
95. Last et al. (1991) Theor. Appl. Genet. 81, 581-588
96. Lawson et al. (1994) Mol Gen Genet 245:608-615
97. Lazzeri P (1995) Methods Mol Biol 49:95-106
98. Leffel et al. (1997) Biotechniques 23(5):912-8
99. Lescot et al. Nucleic Acids Res 30(1):325-7 (2002)
100. Li et al. (1992) Plant Mol Biol 20:1037-1048
101. Llob et al. (2003) Europ J Plant Pathol 109:381-389
102. Lysnik et al. (1993) NAR 21:969-975
103. Lyznik L A et al. (1996) Nucleic Acids Res 24:3784-3789
104. Maniatis T, Fritsch E F and Sambrook J (1989) Molecular Cloning: A Laboratory Manual, 2nd Ed., Cold Spring Harbor Laboratory, Cold Spring Harbor (NY)
105. Massey V et al. *Biochim. Biophys. Acta* 48 (1961) 1-9
106. Matzke M A et al. (2000) Plant Mol Biol 43:401-415
107. Meister A & Wellner D Flavoprotein amino acid oxidase. In: Boyer, P. D., Lardy, H. and Myrbäck, K. (Eds.), *The Enzymes,* 2nd ed., vol. 7, Academic Press, New York, 1963, p. 609-648
108. Melchers et al. (2000) Curr Opin Plant Biol 3(2):147-52
109. Mett et al. PNAS 90: 4567-4571 (1993)
110. Miki et al. (1993) "Procedures for Introducing Foreign DNA into Plants" in METHODS IN PLANT MOLECULAR BIOLOGY AND BIOTECHNOLOGY; pp. 67-88
111. Miyano M et al. (1991) J Biochem 109:171-177
112. Mol J N et al. (1990) FEBS Lett 268(2):427-430
113. Moloney et al. (1989) Plant Cell Reports 8: 238
114. Moore et al. (1997) J. Mol. Biol., 272:336

115. Morgan, B. A. and Gainor, J. A. (1989) Ann. Rep. Med. Chem. 24:243;
116. Mozo & Hooykaas (1991) Plant Mol. Biol. 16:917-918
117. Murai et al., Science 23: 476-482 (1983)
118. Myers and Miller, CABIOS, 4:11 (1988).
119. Needleman and Wunsch, J. Mol. Biol., 48:443-453 (1970).
120. Nehra et al. (1994) Plant J. 5:285-297
121. Odell et al. (1985) Nature 313:810-812;
122. Odell et al. (1990) Mol Gen Genet 223:369-378
123. Olhoft et al. (2001) Plant Cell Rep 20: 706-711
124. Onouchi et al. (1995) Mol Gen Genet 247:653-660
125. Osborne et al. (1995) Plant J. 7, 687-701
126. Paszkowski et al. (1984) EMBO J 3:2717-2722
127. Pearson and Lipman, Proc. Natl. Acad. Sci., 85:2444 (1988).
128. Perl A et al. (1996) Nature Biotechnol 14: 624-628
129. Reichel et al. (1996) Proc Natl Acad Sci USA 93(12): 5888-5893
130. Rouster J et al. (1998) Plant J 15:435-440
131. Russell et al. (1992) Mol Gene Genet 234: 49-59
132. Saijo et al. (2000) Plant J 23(3): 319-327
133. Sakamoto et al. (2000) J Exp Bot 51(342):81-8
134. Sauer B (1998) Methods 14(4):381-92
135. Sawada et al. (1993) International Journal of Systematic Bacteriology 43(4):694-702
136. Sawyer, T. K. (1995) "Peptidomimetic Design and Chemical Approaches to Peptide Metabolism" in Taylor, M. D. and Amidon, G. L. (eds.) Peptide-Based Drug Design Controlling Transport and Metabolism, Chapter 17
137. Schena et al. (1991) Proc Nat'l Acad Sci USA 88:10421
138. Schenborn, Groskreutz (1999) Mol Biotechnol 13(1): 29-44)
139. Schlaman and Hooykaas (1997) Plant J 11:1377-1385)
140. Sengupta-Gopalan et al., (1985) Proc. Natl. Acad. Sci. USA 82: 3320-3324
141. Shah et al. (1986) Science 233: 478
142. Sheehy et al. (1988) Proc Natl Acad Sci USA 85: 8805-8809
143. Sheen et al. (1995) Plant J 8(5):777-784
144. Shewmaker et al. (1985) Virology 140:281-288
145. Shimamoto et al. (1992) Nature 338:274-276
146. Shirsat et al. (1989) Mol Gen Genet 215:326-331
147. Silhavy T J, Berman M L and Enquist L W (1984) Experiments with Gene Fusions, Cold Spring Harbor Laboratory, Cold Spring Harbor (NY)
148. Simpson et al. (1985) EMBO J 4:2723-2729
149. Smith et al., Adv. Appl. Math., 2:482. (1981).
150. Smith, A. B. 3rd, et al. (1994) J. Am. Chem. Soc. 116: 9947-9962
151. Smith, A. B. 3rd, et al. (1995) J. Am. Chem. Soc. 117: 11113-11123
152. Stalberg et al. (1996) Planta 199:515-519
153. Stemmer (1994a) Nature, 370:389-391
154. Stemmer (1994b) Proc Natl Acad. Sci USA 91:10747-10751
155. Sugita K et al. (2000) Plant J. 22:461-469
156. Suzuki (2001) Gene. January 24; 263(1-2):49-58
157. The Maize Handbook, Chapter 116, Freeling and Walbot, Eds., Springer, New York (1994)
158. Thompson J D et al., NAR 22(22):4673-4680 (1994).
159. Tian et al. (1997) Plant Cell Rep 16:267-271
160. Timko et al. (1985) Nature 318: 579-582
161. Trick et al. (1997) Plant Tissue Cult Biotechnol 3:9-26
162. Trieu, et al. (2000) The Plant Journal 22(6), 531-541)).
163. Twell et al. (1983) Sex. Plant Reprod. 6: 217-224
164. Twell et al. (1989b) Mol Gen Genet 217:240-245
165. U.S. Pat. No. 4,801,340
166. U.S. Pat. No. 4,940,838
167. U.S. Pat. No. 4,962,028
168. U.S. Pat. No. 4,975,374
169. U.S. Pat. No. 5,059,239
170. U.S. Pat. No. 5,100,792
171. U.S. Pat. No. 5,225,341
172. U.S. Pat. No. 5,352,605
173. U.S. Pat. No. 5,510,474
174. U.S. Pat. No. 5,605,793
175. U.S. Pat. No. 5,608,152;
176. U.S. Pat. No. 5,683,439
177. U.S. Pat. No. 5,811,238
178. U.S. Pat. No. 5,830,721
179. U.S. Pat. No. 5,837,458
180. US2001034888
181. US2005102711
182. U.S. Pat. No. 5,504,200
183. U.S. Pat. No. 5,584,807
184. Van Laerebeke et al. (1974) Nature 252, 169-170
185. van Veen R J M et al. (1988) Mol Plant Microb Interact 1(6):231-234
186. Vanden Elzen et al. (1985) Plant Mol Biol. 5:299
187. Vasil et al. (1992) Bio/Technology, 10:667-674
188. Vasil et al. (1993) Bio/Technology, 11:1153-1158
189. Velten et al. (1984) EMBO J. 3(12): 2723-2730
190. Vernade et al. (1988) J. Bacteriol. 170: 5822-5829
191. Vinuesa et al. (1998) *Appl. Envir. Microbiol.* 64:2096-2104
192. Wader et al. 1987 Tomato Technology 189-198 Alan R. Liss, Inc.
193. Wan & Lemaux (1994) Plant Physiol. 104:3748
194. Ward et al. (1993) Plant Mol Biol 22:361-366
195. Waterhouse P M et al. (1998) Proc Natl Acad Sci USA 95:13959-64
196. Watson et al. (1975) J. Bacteriol 123, 255-264
197. Watson et al. (1985) EMBO J 4(2):277-284
198. Weeks et al. (1993) Plant Physiol. 102: 1077-1084
199. Wingender E et al. Nucleic Acids Res 29(1):281-3 (2001)
200. WO 00/26388
201. WO 00/58484
202. WO 02/00900
203. WO 02/10415
204. WO 03/004659
205. WO 03/060133
206. WO 03/102198
207. WO 87/06614
208. WO 91/13980
209. WO 92/09696
210. WO 93/01294
211. WO 93/21334
212. WO 93/24640
213. WO 94/00583
214. WO 95/19443
215. WO 97/037012
216. WO 97/41228
217. WO 98/45456
218. WO 98/45461
219. WO 00/44895
220. WO 00/44914
221. WO 00/49035
222. WO 00/63364
223. WO 00/68374
224. WO 99/32619
225. WO 99/53050
226. Yeo et al. (2000) Mol Cells 10(3):263-8
227. Young et al. (2003) Int. J. Systematic & Evolutionary Microbiology 51:89-103
228. Zhang et al. (1997) Proc. Natl. Acad. Sci. USA, 94:4504
229. Zubko et al. (2000) Nature Biotech 18(4):442-445
230. Zupan et al. (2000) Plant J 23(1):11-2

What is claimed is:

1. A method for generating a transgenic soybean plant comprising the steps of:
   a) introducing into a soybean cell or tissue a DNA construct comprising at least one first expression construct comprising a promoter active in said soybean plant and operably linked thereto a nucleic acid sequence encoding an enzyme capable of metabolizing D-serine, and
   b) incubating said soybean cell or tissue of step a) on a selection medium comprising D-serine and/or a derivative thereof in a total concentration from about 0.5 mM to about 100 mM for a time period of at least 5 days, and
   c) transferring said soybean cell or tissue of step b) to a regeneration medium and regenerating and selecting soybean plants comprising said DNA construct, wherein the promoter active in the soybean plant is selected from the group consisting of:
   i) a nucleotide sequence comprising the sequence as described by SEQ ID NO: 7 or 8,
   ii) a nucleotide sequence comprising at least one fragment of at least 50 consecutive base pairs of the sequence as described by SEQ ID NO: 7 or 8, and having promoter activity in soybean,
   iii) a nucleotide sequence comprising a sequence having at least 60% identity to the sequence as described by SEQ ID NO: 7 or 8, and having promoter activity in soybean, and
   iv) a nucleotide sequence comprising a sequence capable of hybridizing under conditions equivalent or equal to hybridization in 30% formamide, 1 M NaCl, 1% SDS at 37° C., and a wash in 2×SSC at 50° C. to the sequence as described by SEQ ID NO: 7 or 8, and having promoter activity in soybean.

2. The method of claim 1, wherein the method comprises the following steps:
   (a) providing an axillary meristematic tissue of a primary or higher leaf node of a soybean seedling,
   (b) co-cultivating said axillary meristematic tissue with a Rhizobiaceae bacterium comprising a transgenic T-DNA, wherein said transgenic T-DNA comprises said DNA construct,
   (c) transferring said co-cultivated axillary meristematic tissue on a shoot induction and selection medium comprising:
      (i) at least one plant growth factor in a concentration suitable to induce de novo shoot induction from said axillary meristematic tissue, and
      (ii) D serine and/or a derivative thereof in a total concentration from about 3 mM to about 100 mM, and
      (iii) optionally one or more antibiotics suitable to inhibit Rhizobiaceae bacterium growth,
   and cultivating said co-cultivated axillary meristematic tissue for a period of at least 5 days on said medium until shoots are induced and developed therefrom and isolating said shoots, and
   (d) transferring said isolated shoots to a rooting medium and cultivating said shoots on said rooting medium until said shoots have formed roots, and further regenerating the so derived plantlets into mature plants, which comprise inserted into their genome said transgenic T-DNA.

3. The method of claim 2, wherein the axillary meristematic tissue of the primary or higher node is provided in a form selected from the group consisting of:
   i) the seedling axillary meristem as provided by substantially the entire seedling,
   ii) the leaf axillary meristem as provided by dissecting the primary or higher leafs in a way that the axillary meristematic tissue remains attached to the petioles of the leafs, and
   iii) propagated axillary meristem.

4. The method of claim 2, wherein the media of step (b), and/or (c), comprises:
   a) a cytokinin in a concentration equivalent to a concentration of about 1 µM to about 10 µM 6-benzylaminopurine, and/or
   b) between about 0.1 µM and about 2 µM Gibberellic acid (GA3), and/or
   c) at least one thiol compound.

5. The method of claim 4, wherein the cytokinin is kinetin at a concentration of 1 µM to 10 µM.

6. The method of claim 1, wherein the enzyme capable of metabolizing D-serine is selected from the group consisting of:
   i) the D-serine ammonia-lyases as shown in Table 1,
   ii) enzymes having the same enzymatic activity and an identity of at least 80% to the amino acid sequence of any of the D-serine ammonia-lyases as shown in Table 1,
   iii) enzymes having the same enzymatic activity and encoded by a nucleic acid sequence having an identity of at least 80% to the nucleic acid sequence encoding any of the D-serine ammonia-lyases as shown in Table 1, and
   iv) enzymes encoded by a nucleic acid sequence capable of hybridizing under conditions equivalent or equal to hybridization in 30% formamide, 1 M NaCl, 1% SDS at 37° C., and a wash in 2×SSC at 50° C. to the complement of the nucleic acid sequence encoding any one of the D-serine ammonia-lyases as shown in Table 1,
   wherein selection is done on a medium comprising D-serine in a concentration from 3 mM to 100 mM.

7. The method of claim 1, wherein the enzyme capable of metabolizing D-serine is a D-serine ammonia-lyases (EC 4.3.1.18).

8. The method of claim 1, wherein the enzyme capable of metabolizing D-serine is selected from the group consisting of:
   i) the *E. coli* D-serine ammonia-lyase as described by SEQ ID NO: 2,
   ii) enzymes having the same enzymatic activity and an identity of at least 60% to the sequence as described by SEQ ID NO: 2, and
   ii) enzymes encoded by a nucleic acid sequence capable of hybridizing under conditions equivalent or equal to hybridization in 30% formamide, 1 M NaCl, 1% SDS at 37° C., and a wash in 2×SSC at 50° C. to the complement of the sequence described by SEQ ID NO: 1,
   wherein selection is done on a medium comprising D-serine in a concentration from about 0.5 mM to about 100 mM.

9. The method of claim 1, wherein the selection is done using about 30 to 50 mM D-serine for about 3 to 4 weeks under dedifferentiating conditions.

10. The method of claim 1, wherein the selection after transformation with a dsda gene comprises the following steps:
    a) 5 to 10 days on shoot induction without selection,
    b) 2 to 4 weeks on shoot induction medium with 5 mM to 10 mM D-serine, and
    c) 2 mM to 7 mM D-serine throughout shoot elongation.

11. The method of claim 1, wherein introduction of said DNA construct is mediated by Rhizobiaceae bacterium mediated transformation.

12. The method of claim 11, wherein the Rhizobiaceae bacterium is a disarmed *Agrobacterium tumefaciens* or *Agrobacterium rhizogenes* bacterium.

13. The method of claim 11, wherein the *Agrobacterium* strain is a disarmed *Agrobacterium rhizogenes* K599 strain.

14. The method of claim 1, further comprising one or more of the following steps:
    a) sterilizing the seedlings;
    b) growing the seedlings for 3 to 10 days, in light;
    c) growing the epicotyl with the unifoliate leaves to the length of the cotyledons or longer;
    d) growing the epicotyl to between 0.5 cm and 4 cm;
    e) removing all preformed leaves including apical meristem;
    f) injuring the node located at the first set of leaves with several cuts;
    g) co-cultivating wounded node with *Agrobacterium* for 0.1 to 1 hour, in liquid medium;
    h) co-cultivating node with *Agrobacterium* for 3 to 5 days in the dark on solid co-cultivation medium;
    i) placing the explants for selection under a 18 h light/6 h dark cycle at 70 to 100 microE/m²s until the axillary merstems grow at the first node above the epicotyl;
    j) removing shoots formed before transformation up to 2 weeks after co-cultivation and optionally cutting during this time the explant into smaller pieces;
    k) transferring the explants to shoot primordia elongation medium after 2 to 4 weeks after co-cultivation and transferring the explants every 2 to 3 weeks to fresh medium with selection agent after removing dead tissue till shoots elongate;

l) removing shoots 3 cm or larger from the explant and placing into root inducing medium for a week till roots begin to form; and m) transferring rooted shoots to soil and hardened in a growth chamber for 2 to 3 weeks before transferring the rooted shoots to greenhouse.

15. The method of claim 1, wherein the DNA construct of step a) is introduced via co-cultivation with *Agrobacterium* and selection pressure is applied after co-cultivation
during on shoot induction,
throughout shoot elongation, or during shoot induction and throughout shoot elongation.

16. The method of claim 1, wherein the promoter comprises a nucleotide sequence having at least 80% identity to the sequence as described by SEQ ID NO: 7 or 8 and having promoter activity in soybean.

17. The method of claim 1, wherein the promoter comprises a nucleotide sequence having at least 95% identity to the sequence as described by SEQ ID NO: 7 or 8 and having promoter activity in soybean.

18. A heterologous nucleotide sequence comprising:
a) a promoter selected from the group consisting of a soybean ubiquitin promoter, an Actin2 promoter from a dicotyledonous plant species, and a p-ScBV or p-ScBV-iSuc UDP promoter, and operably linked thereto
b) a nucleic acid sequence encoding an enzyme capable of metabolizing D-serine,
wherein said promoter is heterologous with respect to said nucleic acid sequence.

19. A soybean plant or cell comprising the heterologous nucleotide sequence according to claim 18.

20. A part or seed of the soybean plant of claim 19.

21. A heterologous nucleotide sequence comprising:
a) a promoter selected from the group consisting of:
i) sequences comprising the sequence as described by SEQ ID NO: 7 or 8, and
ii) sequences comprising at least one fragment of at least 50 consecutive base pairs of the sequence as described by SEQ ID NO: 7 or 8, and having promoter activity in soybean, and
iii) sequences comprising a sequence having at least 60% identity to the sequence as described by SEQ ID NO: 7 or 8, and having promoter activity in soybean, and
iv) sequences comprising a sequence capable of hybridizing under conditions equivalent or equal to hybridization in 30% formamide, 1 M NaCl, 1% SDS at 37° C., and a wash in 2×SSC at 50° C. to the sequence as described by SEQ ID NO: 7 or 8, and having promoter activity in soybean, and
b) a nucleic acid sequence encoding an enzyme capable of metabolizing D-serine according to Table 1,
wherein said promoter is heterologous with respect to said nucleic acid sequence.

22. A soybean plant or cell comprising a DNA construct comprising a promoter active in said soybean plant or cell and operably linked thereto a nucleic acid sequence encoding an enzyme capable of metabolizing D-serine, wherein said promoter is heterologous in relation to said enzyme encoding sequence.

23. A method for subsequent transformation of at least two DNA constructs into a soybean plant comprising the steps of:
a) transforming a first construct comprising at least one expression construct comprising a promoter active in said soybean plant and operably linked thereto a nucleic acid sequence encoding an enzyme capable of metabolizing D-serine, and
b) transforming a second construct comprising a second selection marker gene, which does not confer resistance against D serine.

24. The method of claim 23, wherein said second marker gene confers resistance against at least one compound selected from the group consisting of phosphinotricin, dicamba, glyphosate, sulfonylurea- and imidazolinone-type herbicides, and an antibiotic.

25. A soybean plant comprising
a) a first expression construct comprising a promoter active in said soybean plant and operably linked thereto a nucleic acid sequence encoding an enzyme capable of metabolizing D-serine, and
b) a second expression construct comprising a selection marker gene, which does not confer resistance against D serine.

* * * * *

SEQUENCE LISTING

<160> NUMBER OF SEQ ID NOS: 18

<210> SEQ ID NO 1
<211> LENGTH: 1329
<212> TYPE: DNA
<213> ORGANISM: Escherichia coli
<220> FEATURE:
<221> NAME/KEY: CDS
<222> LOCATION: (1)..(1329)
<223> OTHER INFORMATION: E.coli D-serine dehydratase [dsdA] gene/CDS

<400> SEQUENCE: 1

```
atg gaa aac gct aaa atg aac tcg ctc atc gcc cag tat ccg ttg gta      48
Met Glu Asn Ala Lys Met Asn Ser Leu Ile Ala Gln Tyr Pro Leu Val
1               5                   10                  15 aag gat ctg gtt gct ctt aaa gaa acc acc tgg ttt aat cct ggc acg      96
Lys Asp Leu Val Ala Leu Lys Glu Thr Thr Trp Phe Asn Pro Gly Thr
            20                  25                  30 acc tca ttg gct gaa ggt tta cct tat gtt ggc ctg acc gaa cag gat     144
Thr Ser Leu Ala Glu Gly Leu Pro Tyr Val Gly Leu Thr Glu Gln Asp
        35                  40                  45 gtt cag gac gcc cat gcg cgc tta tcc cgt ttt gca ccc tat ctg gca     192
Val Gln Asp Ala His Ala Arg Leu Ser Arg Phe Ala Pro Tyr Leu Ala
    50                  55                  60 aaa gca ttt cct gaa act gct gcc act ggg ggg att att gaa tca gaa     240
Lys Ala Phe Pro Glu Thr Ala Ala Thr Gly Gly Ile Ile Glu Ser Glu
65                  70                  75                  80 ctg gtt gcc att cca gct atg caa aaa cgg ctg gaa aaa gaa tat cag     288
Leu Val Ala Ile Pro Ala Met Gln Lys Arg Leu Glu Lys Glu Tyr Gln
                85                  90                  95 caa ccg atc agc ggg caa ctg tta ctg aaa aaa gat agc cat ttg ccc     336
Gln Pro Ile Ser Gly Gln Leu Leu Leu Lys Lys Asp Ser His Leu Pro
            100                 105                 110 att tcc ggc tcc ata aaa gca cgc ggc ggg att tat gaa gtc ctg gca     384
Ile Ser Gly Ser Ile Lys Ala Arg Gly Gly Ile Tyr Glu Val Leu Ala
        115                 120                 125 cac gca gaa aaa ctg gct ctg gaa gcg ggg ttg ctg acg ctt gat gat     432
His Ala Glu Lys Leu Ala Leu Glu Ala Gly Leu Leu Thr Leu Asp Asp
    130                 135                 140 gac tac agc aaa ctg ctt tct ccg gag ttt aaa cag ttc ttt agc caa     480
Asp Tyr Ser Lys Leu Leu Ser Pro Glu Phe Lys Gln Phe Phe Ser Gln
145                 150                 155                 160 tac agc att gct gtg ggc tca acc gga aat ctg ggg tta tca atc ggc     528
Tyr Ser Ile Ala Val Gly Ser Thr Gly Asn Leu Gly Leu Ser Ile Gly
                165                 170                 175 att atg agc gcc cgc att ggc ttt aag gtg aca gtt cat atg tct gct     576
Ile Met Ser Ala Arg Ile Gly Phe Lys Val Thr Val His Met Ser Ala
            180                 185                 190 gat gcc cgg gca tgg aaa aaa gcg aaa ctg cgc agc cat ggc gtt acg     624
Asp Ala Arg Ala Trp Lys Lys Ala Lys Leu Arg Ser His Gly Val Thr
        195                 200                 205 gtc gtg gaa tat gag caa gat tat ggt gtt gcc gtc gag gaa gga cgt     672
Val Val Glu Tyr Glu Gln Asp Tyr Gly Val Ala Val Glu Glu Gly Arg
    210                 215                 220 aaa gca gcg cag tct gac ccg aac tgt ttc ttt att gat gac gaa aat     720
Lys Ala Ala Gln Ser Asp Pro Asn Cys Phe Phe Ile Asp Asp Glu Asn
225                 230                 235                 240 tcc cgc acg ttg ttc ctt ggg tat tcc gtc gct ggc cag cgt ctt aaa     768
Ser Arg Thr Leu Phe Leu Gly Tyr Ser Val Ala Gly Gln Arg Leu Lys
                245                 250                 255
```

```
gcg caa ttt gcc cag caa ggc cgt atc gtc gat gct gat aac cct ctg      816
Ala Gln Phe Ala Gln Gln Gly Arg Ile Val Asp Ala Asp Asn Pro Leu
        260                 265                 270 ttt gtc tat ctg ccg tgt ggt gtt ggc ggt ggt cct ggt ggc gtc gca      864
Phe Val Tyr Leu Pro Cys Gly Val Gly Gly Gly Pro Gly Gly Val Ala
            275                 280                 285 ttc ggg ctt aaa ctg gcg ttt ggc gat cat gtt cac tgc ttt ttt gcc      912
Phe Gly Leu Lys Leu Ala Phe Gly Asp His Val His Cys Phe Phe Ala
        290                 295                 300 gaa cca acg cac tcc cct tgt atg ttg tta ggc gtc cat aca gga tta      960
Glu Pro Thr His Ser Pro Cys Met Leu Leu Gly Val His Thr Gly Leu
305                 310                 315                 320 cac gat cag att tct gtt cag gat att ggt atc gac aac ctt acc gca     1008
His Asp Gln Ile Ser Val Gln Asp Ile Gly Ile Asp Asn Leu Thr Ala
                325                 330                 335 gcg gat ggc ctt gca gtt ggt cgc gca tca ggc ttt gtc ggg cgg gca     1056
Ala Asp Gly Leu Ala Val Gly Arg Ala Ser Gly Phe Val Gly Arg Ala
            340                 345                 350 atg gag cgt ctg ctg gat ggc ttc tat acc ctt agc gat caa acc atg     1104
Met Glu Arg Leu Leu Asp Gly Phe Tyr Thr Leu Ser Asp Gln Thr Met
        355                 360                 365 tat gac atg ctt ggc tgg ctg gcg cag gaa gaa ggt att cgt ctt gaa     1152
Tyr Asp Met Leu Gly Trp Leu Ala Gln Glu Glu Gly Ile Arg Leu Glu
370                 375                 380 cct tcg gca ctg gcg ggt atg gcc gga cct cag cgc gtg tgt gca tca     1200
Pro Ser Ala Leu Ala Gly Met Ala Gly Pro Gln Arg Val Cys Ala Ser
385                 390                 395                 400 gta agt tac caa cag atg cac ggt ttc agc gca gaa caa ctg cgt aat     1248
Val Ser Tyr Gln Gln Met His Gly Phe Ser Ala Glu Gln Leu Arg Asn
                405                 410                 415 acc act cat ctg gtg tgg gcg acg gga ggt gga atg gtg ccg gaa gaa     1296
Thr Thr His Leu Val Trp Ala Thr Gly Gly Gly Met Val Pro Glu Glu
            420                 425                 430 gag atg aat caa tat ctg gca aaa ggc cgt taa                         1329
Glu Met Asn Gln Tyr Leu Ala Lys Gly Arg
        435                 440

<210> SEQ ID NO 2
<211> LENGTH: 442
<212> TYPE: PRT
<213> ORGANISM: Escherichia coli

<400> SEQUENCE: 2

Met Glu Asn Ala Lys Met Asn Ser Leu Ile Ala Gln Tyr Pro Leu Val
1               5                   10                  15

Lys Asp Leu Val Ala Leu Lys Glu Thr Thr Trp Phe Asn Pro Gly Thr
            20                  25                  30

Thr Ser Leu Ala Glu Gly Leu Pro Tyr Val Gly Leu Thr Glu Gln Asp
        35                  40                  45

Val Gln Asp Ala His Ala Arg Leu Ser Arg Phe Ala Pro Tyr Leu Ala
    50                  55                  60

Lys Ala Phe Pro Glu Thr Ala Ala Thr Gly Gly Ile Ile Glu Ser Glu
65                  70                  75                  80

Leu Val Ala Ile Pro Ala Met Gln Lys Arg Leu Glu Lys Glu Tyr Gln
                85                  90                  95

Gln Pro Ile Ser Gly Gln Leu Leu Leu Lys Lys Asp Ser His Leu Pro
            100                 105                 110

Ile Ser Gly Ser Ile Lys Ala Arg Gly Gly Ile Tyr Glu Val Leu Ala
        115                 120                 125
```

```
His Ala Glu Lys Leu Ala Leu Glu Ala Gly Leu Leu Thr Leu Asp Asp
            130                 135                 140

Asp Tyr Ser Lys Leu Leu Ser Pro Glu Phe Lys Gln Phe Phe Ser Gln
145                 150                 155                 160

Tyr Ser Ile Ala Val Gly Ser Thr Gly Asn Leu Gly Leu Ser Ile Gly
                165                 170                 175

Ile Met Ser Ala Arg Ile Gly Phe Lys Val Thr Val His Met Ser Ala
            180                 185                 190

Asp Ala Arg Ala Trp Lys Lys Ala Lys Leu Arg Ser His Gly Val Thr
        195                 200                 205

Val Val Glu Tyr Glu Gln Asp Tyr Gly Val Ala Val Glu Glu Gly Arg
    210                 215                 220

Lys Ala Ala Gln Ser Asp Pro Asn Cys Phe Phe Ile Asp Asp Glu Asn
225                 230                 235                 240

Ser Arg Thr Leu Phe Leu Gly Tyr Ser Val Ala Gly Gln Arg Leu Lys
                245                 250                 255

Ala Gln Phe Ala Gln Gln Gly Arg Ile Val Asp Ala Asp Asn Pro Leu
            260                 265                 270

Phe Val Tyr Leu Pro Cys Gly Val Gly Gly Pro Gly Gly Val Ala
        275                 280                 285

Phe Gly Leu Lys Leu Ala Phe Gly Asp His Val His Cys Phe Phe Ala
    290                 295                 300

Glu Pro Thr His Ser Pro Cys Met Leu Leu Gly Val His Thr Gly Leu
305                 310                 315                 320

His Asp Gln Ile Ser Val Gln Asp Ile Gly Ile Asp Asn Leu Thr Ala
                325                 330                 335

Ala Asp Gly Leu Ala Val Gly Arg Ala Ser Gly Phe Val Gly Arg Ala
            340                 345                 350

Met Glu Arg Leu Leu Asp Gly Phe Tyr Thr Leu Ser Asp Gln Thr Met
        355                 360                 365

Tyr Asp Met Leu Gly Trp Leu Ala Gln Glu Glu Gly Ile Arg Leu Glu
    370                 375                 380

Pro Ser Ala Leu Ala Gly Met Ala Gly Pro Gln Arg Val Cys Ala Ser
385                 390                 395                 400

Val Ser Tyr Gln Gln Met His Gly Phe Ser Ala Glu Gln Leu Arg Asn
                405                 410                 415

Thr Thr His Leu Val Trp Ala Thr Gly Gly Gly Met Val Pro Glu Glu
            420                 425                 430

Glu Met Asn Gln Tyr Leu Ala Lys Gly Arg
        435                 440

<210> SEQ ID NO 3
<211> LENGTH: 1107
<212> TYPE: DNA
<213> ORGANISM: Rhodosporidium toruloides
<220> FEATURE:
<221> NAME/KEY: CDS
<222> LOCATION: (1)..(1107)
<223> OTHER INFORMATION: Rhodosporidium toruloides D-amino acid oxidase
      CDS

<400> SEQUENCE: 3 atg cac tcg cag aag cgc gtc gtt gtc ctc gga tca ggc gtt atc ggt      48
Met His Ser Gln Lys Arg Val Val Val Leu Gly Ser Gly Val Ile Gly
1               5                   10                  15 ctg agc agc gcc ctc atc ctc gct cgg aag ggc tac agc gtg cat att     96
Leu Ser Ser Ala Leu Ile Leu Ala Arg Lys Gly Tyr Ser Val His Ile
            20                  25                  30
```

-continued

| | | | | | | | | | | | | | | | |
|---|---|---|---|---|---|---|---|---|---|---|---|---|---|---|---|
| ctc | gcg | cgc | gac | ttg | ccg | gag | gac | gtc | tcg | agc | cag | act | ttc | gct | tca | 144 |
| Leu | Ala | Arg | Asp | Leu | Pro | Glu | Asp | Val | Ser | Ser | Gln | Thr | Phe | Ala | Ser | |
| | | 35 | | | | 40 | | | | 45 | | | | | | |

| cca | tgg | gct | ggc | gcg | aat | tgg | acg | cct | ttc | atg | acg | ctt | aca | gac | ggt | 192 |
| Pro | Trp | Ala | Gly | Ala | Asn | Trp | Thr | Pro | Phe | Met | Thr | Leu | Thr | Asp | Gly | |
| 50 | | | | | 55 | | | | | 60 | | | | | | |

| cct | cga | caa | gca | aaa | tgg | gaa | gaa | tcg | act | ttc | aag | aag | tgg | gtc | gag | 240 |
| Pro | Arg | Gln | Ala | Lys | Trp | Glu | Glu | Ser | Thr | Phe | Lys | Lys | Trp | Val | Glu | |
| 65 | | | | | 70 | | | | | 75 | | | | | 80 | |

| ttg | gtc | ccg | acg | ggc | cat | gcc | atg | tgg | ctc | aag | ggg | acg | agg | cgg | ttc | 288 |
| Leu | Val | Pro | Thr | Gly | His | Ala | Met | Trp | Leu | Lys | Gly | Thr | Arg | Arg | Phe | |
| | | | | 85 | | | | | 90 | | | | | 95 | | |

| gcg | cag | aac | gaa | gac | ggc | ttg | ctc | ggg | cac | tgg | tac | aag | gac | atc | acg | 336 |
| Ala | Gln | Asn | Glu | Asp | Gly | Leu | Leu | Gly | His | Trp | Tyr | Lys | Asp | Ile | Thr | |
| | | | 100 | | | | | 105 | | | | | 110 | | | |

| cca | aat | tac | cgc | ccc | ctc | cca | tct | tcc | gaa | tgt | cca | cct | ggc | gct | atc | 384 |
| Pro | Asn | Tyr | Arg | Pro | Leu | Pro | Ser | Ser | Glu | Cys | Pro | Pro | Gly | Ala | Ile | |
| | | | 115 | | | | | 120 | | | | | 125 | | | |

| ggc | gta | acc | tac | gac | acc | ctc | tcc | gtc | cac | gca | cca | aag | tac | tgc | cag | 432 |
| Gly | Val | Thr | Tyr | Asp | Thr | Leu | Ser | Val | His | Ala | Pro | Lys | Tyr | Cys | Gln | |
| | 130 | | | | | 135 | | | | | 140 | | | | | |

| tac | ctt | gca | aga | gag | ctg | cag | aag | ctc | ggc | gcg | acg | ttt | gag | aga | cgg | 480 |
| Tyr | Leu | Ala | Arg | Glu | Leu | Gln | Lys | Leu | Gly | Ala | Thr | Phe | Glu | Arg | Arg | |
| 145 | | | | | 150 | | | | | 155 | | | | | 160 | |

| acc | gtt | acg | tcg | ctt | gag | cag | gcg | ttc | gac | ggt | gcg | gat | ttg | gtg | gtc | 528 |
| Thr | Val | Thr | Ser | Leu | Glu | Gln | Ala | Phe | Asp | Gly | Ala | Asp | Leu | Val | Val | |
| | | | | 165 | | | | | 170 | | | | | 175 | | |

| aac | gct | acg | gga | ctt | ggc | gcc | aag | tcg | att | gcg | ggc | atc | gac | gac | caa | 576 |
| Asn | Ala | Thr | Gly | Leu | Gly | Ala | Lys | Ser | Ile | Ala | Gly | Ile | Asp | Asp | Gln | |
| | | | 180 | | | | | 185 | | | | | 190 | | | |

| gcc | gcc | gag | cca | atc | cgc | ggg | caa | acc | gtc | ctc | gtc | aag | tcc | cca | tgc | 624 |
| Ala | Ala | Glu | Pro | Ile | Arg | Gly | Gln | Thr | Val | Leu | Val | Lys | Ser | Pro | Cys | |
| | | 195 | | | | | 200 | | | | | 205 | | | | |

| aag | cga | tgc | acg | atg | gac | tcg | tcc | gac | ccc | gct | tct | ccc | gcc | tac | atc | 672 |
| Lys | Arg | Cys | Thr | Met | Asp | Ser | Ser | Asp | Pro | Ala | Ser | Pro | Ala | Tyr | Ile | |
| | 210 | | | | | 215 | | | | | 220 | | | | | |

| att | ccc | cga | cca | ggt | ggc | gaa | gtc | atc | tgc | ggc | ggg | acg | tac | ggc | gtg | 720 |
| Ile | Pro | Arg | Pro | Gly | Gly | Glu | Val | Ile | Cys | Gly | Gly | Thr | Tyr | Gly | Val | |
| 225 | | | | | 230 | | | | | 235 | | | | | 240 | |

| gga | gac | tgg | gac | ttg | tct | gtc | aac | cca | gag | acg | gtc | cag | cgg | atc | ctc | 768 |
| Gly | Asp | Trp | Asp | Leu | Ser | Val | Asn | Pro | Glu | Thr | Val | Gln | Arg | Ile | Leu | |
| | | | | 245 | | | | | 250 | | | | | 255 | | |

| aag | cac | tgc | ttg | cgc | ctc | gac | ccg | acc | atc | tcg | agc | gac | gga | acg | atc | 816 |
| Lys | His | Cys | Leu | Arg | Leu | Asp | Pro | Thr | Ile | Ser | Ser | Asp | Gly | Thr | Ile | |
| | | | 260 | | | | | 265 | | | | | 270 | | | |

| gaa | ggc | atc | gag | gtc | ctc | cgc | cac | aac | gtc | ggc | ttg | cga | cct | gca | cga | 864 |
| Glu | Gly | Ile | Glu | Val | Leu | Arg | His | Asn | Val | Gly | Leu | Arg | Pro | Ala | Arg | |
| | | | 275 | | | | | 280 | | | | | 285 | | | |

| cga | ggc | gga | ccc | cgc | gtt | gag | gca | gaa | cgg | atc | gtc | ctg | cct | ctc | gac | 912 |
| Arg | Gly | Gly | Pro | Arg | Val | Glu | Ala | Glu | Arg | Ile | Val | Leu | Pro | Leu | Asp | |
| | | 290 | | | | | 295 | | | | | 300 | | | | |

| cgg | aca | aag | tcg | ccc | ctc | tcg | ctc | ggc | agg | ggc | agc | gca | cga | gcg | gcg | 960 |
| Arg | Thr | Lys | Ser | Pro | Leu | Ser | Leu | Gly | Arg | Gly | Ser | Ala | Arg | Ala | Ala | |
| 305 | | | | | 310 | | | | | 315 | | | | | 320 | |

| aag | gag | aag | gag | gtc | acg | ctt | gtg | cat | gcg | tat | ggc | ttc | tcg | agt | gcg | 1008 |
| Lys | Glu | Lys | Glu | Val | Thr | Leu | Val | His | Ala | Tyr | Gly | Phe | Ser | Ser | Ala | |
| | | | | 325 | | | | | 330 | | | | | 335 | | |

| gga | tac | cag | cag | agt | tgg | ggc | gcg | gcg | gag | gat | gtc | gcg | cag | ctc | gtc | 1056 |
| Gly | Tyr | Gln | Gln | Ser | Trp | Gly | Ala | Ala | Glu | Asp | Val | Ala | Gln | Leu | Val | |
| | | | 340 | | | | | 345 | | | | | 350 | | | |

```
gac gag gcg ttc cag cgg tac cac ggc gcg gcg cgg gag tcg aag ttg    1104
Asp Glu Ala Phe Gln Arg Tyr His Gly Ala Ala Arg Glu Ser Lys Leu
        355                 360                 365 tag                                                                 1107

<210> SEQ ID NO 4
<211> LENGTH: 368
<212> TYPE: PRT
<213> ORGANISM: Rhodosporidium toruloides

<400> SEQUENCE: 4

Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
                35                  40                  45

Pro Trp Ala Gly Ala Asn Trp Thr Pro Phe Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
                100                 105                 110

Pro Asn Tyr Arg Pro Leu Pro Ser Ser Glu Cys Pro Pro Gly Ala Ile
                115                 120                 125

Gly Val Thr Tyr Asp Thr Leu Ser Val His Ala Pro Lys Tyr Cys Gln
        130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
                180                 185                 190

Ala Ala Glu Pro Ile Arg Gly Gln Thr Val Leu Val Lys Ser Pro Cys
                195                 200                 205

Lys Arg Cys Thr Met Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
                260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Val Leu Pro Leu Asp
        290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350
```

Asp Glu Ala Phe Gln Arg Tyr His Gly Ala Ala Arg Glu Ser Lys Leu
         355                 360                 365

<210> SEQ ID NO 5
<211> LENGTH: 1104
<212> TYPE: DNA
<213> ORGANISM: Rhodosporidium toruloides
<220> FEATURE:
<221> NAME/KEY: CDS
<222> LOCATION: (1)..(1104)
<223> OTHER INFORMATION: Rhodosporidium toruloides D-amino acid oxidase
      [dao1] cds, [Genbank #U60066]. codon optimized

<400> SEQUENCE: 5

```
atg cac tct caa aaa cgc gtt gta gta ttg ggt tcg gga gtc ata ggt      48
Met His Ser Gln Lys Arg Val Val Val Leu Gly Ser Gly Val Ile Gly
1               5                   10                  15 ctt tct tct gct ctt ata ctt gca cgc aag ggc tat tct gtt cat att      96
Leu Ser Ser Ala Leu Ile Leu Ala Arg Lys Gly Tyr Ser Val His Ile
                20                  25                  30 ttg gca cgc gat ctc cca gag gac gta tct agc caa act ttc gct tcc     144
Leu Ala Arg Asp Leu Pro Glu Asp Val Ser Ser Gln Thr Phe Ala Ser
            35                  40                  45 ccc tgg gct ggt gcg aat tgg aca cca ttt atg aca ttg act gac ggc     192
Pro Trp Ala Gly Ala Asn Trp Thr Pro Phe Met Thr Leu Thr Asp Gly
    50                  55                  60 cct aga cag gca aaa tgg gaa gag agt acc ttt aaa aaa tgg gtt gag     240
Pro Arg Gln Ala Lys Trp Glu Glu Ser Thr Phe Lys Lys Trp Val Glu
65                  70                  75                  80 ttg gtc cct acc gga cat gct atg tgg ctg aag gga act cgt cgc ttt     288
Leu Val Pro Thr Gly His Ala Met Trp Leu Lys Gly Thr Arg Arg Phe
                85                  90                  95 gca cag aat gaa gac ggc ttg ctt gga cat tgg tac aaa gat ata acc     336
Ala Gln Asn Glu Asp Gly Leu Leu Gly His Trp Tyr Lys Asp Ile Thr
                100                 105                 110 ccg aat tac cgc ccc ctt ccc tcg tct gaa tgt cca cca ggc gca att     384
Pro Asn Tyr Arg Pro Leu Pro Ser Ser Glu Cys Pro Pro Gly Ala Ile
            115                 120                 125 ggc gtg act tat gac aca ctc tct gta cac gct cct aaa tat tgt cag     432
Gly Val Thr Tyr Asp Thr Leu Ser Val His Ala Pro Lys Tyr Cys Gln
    130                 135                 140 tat ctt gcc aga gaa ctt cag aaa ctc ggt gca act ttt gaa aga cgg     480
Tyr Leu Ala Arg Glu Leu Gln Lys Leu Gly Ala Thr Phe Glu Arg Arg
145                 150                 155                 160 acg gtt acc tca ctg gaa cag gca ttc gac ggt gca gac ctc gtg gtg     528
Thr Val Thr Ser Leu Glu Gln Ala Phe Asp Gly Ala Asp Leu Val Val
                165                 170                 175 aat gca aca gga ctg gga gca aag agc ata gca ggc ata gat gat caa     576
Asn Ala Thr Gly Leu Gly Ala Lys Ser Ile Ala Gly Ile Asp Asp Gln
                180                 185                 190 gct gcg gag cca att aga ggc cag acc gtg ctg gta aaa tca cca tgc     624
Ala Ala Glu Pro Ile Arg Gly Gln Thr Val Leu Val Lys Ser Pro Cys
            195                 200                 205 aaa aga tgt acg atg gat agt agt gac cca gcg agt cca gct tat att     672
Lys Arg Cys Thr Met Asp Ser Ser Asp Pro Ala Ser Pro Ala Tyr Ile
    210                 215                 220 ata ccg aga ccg ggt ggc gaa gtt ata tgc gga gga act tac gga gtg     720
Ile Pro Arg Pro Gly Gly Glu Val Ile Cys Gly Gly Thr Tyr Gly Val
225                 230                 235                 240 ggt gat tgg gat ctt agc gtt aac ccc gaa aca gtc caa cgg att ctg     768
Gly Asp Trp Asp Leu Ser Val Asn Pro Glu Thr Val Gln Arg Ile Leu
                245                 250                 255
```

```
aag cat tgc ctc cgc ctt gac cca acc ata tca tct gac gga acc att      816
Lys His Cys Leu Arg Leu Asp Pro Thr Ile Ser Ser Asp Gly Thr Ile
            260                 265                 270 gag gga atc gaa gta ctt agg cat aat gtt ggt ctt agg ccc gct cgt      864
Glu Gly Ile Glu Val Leu Arg His Asn Val Gly Leu Arg Pro Ala Arg
        275                 280                 285 aga gga gga cca cgt gta gaa gct gag aga att gta ttg ccc ctc gat      912
Arg Gly Gly Pro Arg Val Glu Ala Glu Arg Ile Val Leu Pro Leu Asp
    290                 295                 300 aga acc aaa agc ccc ctt tcg ctt gga aga gga agc gca cgt gca gct      960
Arg Thr Lys Ser Pro Leu Ser Leu Gly Arg Gly Ser Ala Arg Ala Ala
305                 310                 315                 320 aag gaa aaa gaa gtc aca ctg gta cat gca tat ggt ttt agt agt gcc     1008
Lys Glu Lys Glu Val Thr Leu Val His Ala Tyr Gly Phe Ser Ser Ala
                325                 330                 335 gga tat cag caa tca tgg ggt gct gca gaa gat gtt gct cag ttg gtg     1056
Gly Tyr Gln Gln Ser Trp Gly Ala Ala Glu Asp Val Ala Gln Leu Val
            340                 345                 350 gac gag gca ttc caa aga tac cac ggt gca gcg aga gag tca aaa ctt     1104
Asp Glu Ala Phe Gln Arg Tyr His Gly Ala Ala Arg Glu Ser Lys Leu
        355                 360                 365

<210> SEQ ID NO 6
<211> LENGTH: 368
<212> TYPE: PRT
<213> ORGANISM: Rhodosporidium toruloides

<400> SEQUENCE: 6

Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Asn Trp Thr Pro Phe Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
```

```
                   225                 230                 235                 240
Gly Asp Trp Asp Leu Ser Val Asn Pro Glu Thr Val Gln Arg Ile Leu
                245                 250                 255
Lys His Cys Leu Arg Leu Asp Pro Thr Ile Ser Ser Asp Gly Thr Ile
            260                 265                 270
Glu Gly Ile Glu Val Leu Arg His Asn Val Gly Leu Arg Pro Ala Arg
        275                 280                 285
Arg Gly Gly Pro Arg Val Glu Ala Glu Arg Ile Val Leu Pro Leu Asp
    290                 295                 300
Arg Thr Lys Ser Pro Leu Ser Leu Gly Arg Gly Ser Ala Arg Ala Ala
305                 310                 315                 320
Lys Glu Lys Glu Val Thr Leu Val His Ala Tyr Gly Phe Ser Ser Ala
                325                 330                 335
Gly Tyr Gln Gln Ser Trp Gly Ala Ala Glu Asp Val Ala Gln Leu Val
            340                 345                 350
Asp Glu Ala Phe Gln Arg Tyr His Gly Ala Ala Arg Glu Ser Lys Leu
        355                 360                 365

<210> SEQ ID NO 7
<211> LENGTH: 996
<212> TYPE: DNA
<213> ORGANISM: Petroselinum crispum
<220> FEATURE:
<221> NAME/KEY: promoter
<222> LOCATION: (1)..(996)
<223> OTHER INFORMATION: MTX Parsley UBI4-2 promoter with internal
      intron; 99% homology to #PCCUBI42 P.crispum gene Pcubi4-2 for
      polyubiquitin.
<220> FEATURE:
<221> NAME/KEY: Intron
<222> LOCATION: (406)..(993)
<223> OTHER INFORMATION: MTX Parsley UBI4-2 promoter's internal intron;
      99% homology to #PCCUBI42 P.crispum gene Pcubi4-2 for
      polyubiquitin.

<400> SEQUENCE: 7
cttgactaga gaattcgaat ccaaaaatta cggatatgaa tataggcata tccgtatccg      60
aattatccgt ttgacagcta gcaacgattg tacaattgct tctttaaaaa aggaagaaag     120
aaagaaagaa aagaatcaac atcagcgtta acaaacggcc ccgttacggc ccaaacggtc     180
atatagagta acggcgttaa gcgttgaaag actcctatcg aaatacgtaa ccgcaaacgt     240
gtcatagtca gatcccctct tccttcaccg cctcaaacac aaaaataatc ttctacagcc     300
tatatataca accccccctt ctatctctcc tttctcacaa ttcatcatct ttctttctct     360 accccccaatt ttaagaaatc ctctcttctc ctcttcattt tcaaggtaaa tctctctctc     420
tctctctctc tctgttattc cttgttttaa ttaggtatgt attattgcta gtttgttaat     480
ctgcttatct tatgtatgcc ttatgtgaat atctttatct tgttcatctc atccgtttag     540
aagctataaa tttgttgatt tgactgtgta tctacacgtg gttatgttta tatctaatca     600
gatatgaatt tcttcatatt gttgcgtttg tgtgtaccaa tccgaaatcg ttgatttttt     660
tcatttaatc gtgtagctaa ttgtacgtat acatatggat ctacgtatca attgttcatc     720
tgtttgtgtt tgtatgtata cagatctgaa acatcactt ctctcatctg attgtgttgt     780
tacatacata gatatagatc tgttatatca tttttttttat taattgtgta tatatatatg     840
tgcatagatc tggattacat gattgtgatt atttacatga ttttgttatt tacgtatgta     900
tatatgtaga tctggacttt ttggagttgt tgacttgatt gtatttgtgt gtgtatatgt     960
gtgttctgat cttgatatgt tatgtatgtg cagccc                               996
```

```
<210> SEQ ID NO 8
<211> LENGTH: 2031
<212> TYPE: DNA
<213> ORGANISM: Glycine max
<220> FEATURE:
<221> NAME/KEY: promoter
<222> LOCATION: (1)..(999)
<223> OTHER INFORMATION: putative promoter region of soybean ubiquitin
      gene TATA box: 950-964
<220> FEATURE:
<221> NAME/KEY: TATA_signal
<222> LOCATION: (950)..(964)
<223> OTHER INFORMATION: putative TATA box
<220> FEATURE:
<221> NAME/KEY: Intron
<222> LOCATION: (1519)..(2031)
<223> OTHER INFORMATION: first intron located in 5' UTR

<400> SEQUENCE: 8
aaatgaaaga aaaggtatt cacgctctta aaataaatta gtaagcagaa attccaaaat      60
tttcagttag tccttactaa ttattaaatt atagtattaa tccaatgtga ttgcggttac    120
atcatgtacg gaaaataat tctaatcctt gatttaaatt tgatcttgac tatttattta    180
ttctttattt cattttgtaa atcattttat gtatctcctg gcaagcaatt ttatccacct    240
tgcaccaaca ccttcgggtt ccataatcaa accaccttaa cttcacacca tgctgtaact    300
cacaccgccc agcatctcca atgtgaaaga agctaaaatt taataaacaa tcatacgaag    360
cagtgacaaa ataccagatg gtattaatgc tttgataaaa ttaattggaa agtataaaat    420
ggtagaaaat aataaattat aattaattta aataagataa aaaataatta aaaactaaaa    480
tgttaaaatt ttaaaaaaat tattttaaat aatatttaaa aacattaaaa atcattttaa    540
aaaatttatt tatagaacaa ttaaataaat atttcagcta ataaaaaaca aaagcttacc    600
tagccttaga agacaacttg tccaacaatt agatgatacc cattgcccctt acgttttctt    660 taacatcaat tattgttttt gtcaacaagc tatcttttag ttttattta ttggtaaaaa    720 atatgtcgcc ttcaagttgc atcatttaac acatctcgtc attagaaaaa taaaactctt    780
ccctaaacga ttagtagaaa aaatcattcg ataataaata agaaagaaaa attagaaaaa    840
aataacttca ttttaaaaaa atcattaagg ctatatttt taaatgacta attttatata    900
gactgtaact aaaagtatac aatttattat gctatgtatc ttagagaatt acttataaaa    960
atctacggaa gaatatctta caaagtgaaa aacaaatgag aaagaattta gtgggatgat   1020
tatgatttta tttgaaaatt gaaaaaataa ttattaaaga ctttagtgga gtaagaaagc   1080
tttcctatta gtcttttctt atccataaaa aaaaaaaaa aaatctagcg tgacagcttt   1140
tccatagatt ttaataatgt aaaatactgg tagcagccga ccgttcaggt aatggacact   1200
gtggtcctaa cttgcaacgg gtgcgggccc aatttaataa cgccgtggta acagataaag   1260
ccaagcgtga agcggtgaag gtacatctct gactccgtca agattacgaa accgtcaact   1320
acgaaggact ccccgaaata tcatctgtgt cataaacacc aagtcacacc atacatgggc   1380
acgcgtcaca atatgattgg agaacggttc caccgcatat gctataaaat gcccccacac   1440
ccctcgaccc taatcgcact tcaattgcaa tcaaattagt tcattctctt tgcgcagttc   1500
cctacctctc ctttcaaggt tcgtagattt cttctgtttt tttttcttct tctttattgt   1560
ttgttctaca tcagcatgat gttgatttga ttgtgttttc tatcgtttca tcgattataa   1620
attttcataa tcagaagatt cagcttttat taatgcaaga acgtccttaa ttgatgattt   1680
tataaccgta aattaggtct aattagagtt ttttcataa agattttcag atccgtttac   1740
agcaagcctt aattgttgat tctgtagtcg tagattaagg ttttttttcat gaactacttc   1800
```

```
agatccgtta acaacagcc ttatttgttg atacttcagt cgtttttcaa gaaattgttc    1860
agatccgttg ataaaagcct tattcgttga ttctgtatgg tatttcaaga gatattgctc    1920
aggtccttta gcaactacct tatttgttga ttctgtggcc atagattagg atttttttttc   1980 acgaaattgc ttcttgaaat tacgtgatgg attttgattc tgatttatct t             2031
```

```
<210> SEQ ID NO 9
<211> LENGTH: 10096
<212> TYPE: DNA
<213> ORGANISM: Artificial sequence
<220> FEATURE:
<223> OTHER INFORMATION: Bar-Selda Binary Vector RLM407: LB>
      <p-NOS::c-BAR::t-NOS p-PcUBI4-2::c-dsdA/na::t-NOS> RB>.
<220> FEATURE:
<221> NAME/KEY: misc_feature
<222> LOCATION: (1)..(215)
<223> OTHER INFORMATION: Left T-DNA border (full) similar to #TIP37TD1
      Ti plasmid (from A.tumefaciens, nopaline strain T37).
<220> FEATURE:
<221> NAME/KEY: misc_feature
<222> LOCATION: (47)..(71)
<223> OTHER INFORMATION: Left T-DNA Border repeat region; similar to
      #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
      poly-A terminator.
<220> FEATURE:
<221> NAME/KEY: misc_feature
<222> LOCATION: (527)..(1078)
<223> OTHER INFORMATION: Complement of CDS for BAR gene; 100% homologous
      to #SHBARPA Streptomyces hygroscopicus bar gene for
      phosphinothricin acetyl transferase.
<220> FEATURE:
<221> NAME/KEY: promoter
<222> LOCATION: (1092)..(1379)
<223> OTHER INFORMATION: Complement of promoter from the noplaine
      synthase gene (Depicker et al. 1982, J.Mol.Appl.Genet. 1:561-573)
      EMBL no: V00087.
<220> FEATURE:
<221> NAME/KEY: promoter
<222> LOCATION: (1746)..(2741)
<223> OTHER INFORMATION: Parsley UBI4-2 promoter with internal intron;
      99% homology to #PCCUBI42 P.crispum gene Pcubi4-2 for
      polyubiquitin; from QC28-6/JB010.
<220> FEATURE:
<221> NAME/KEY: misc_feature
<222> LOCATION: (2826)..(4154)
<223> OTHER INFORMATION: E. coli D-serine deaminase [dsdA] gene/CDS;
      from QC78-6/SUH405. [GenBank J01603]
<220> FEATURE:
<221> NAME/KEY: terminator
<222> LOCATION: (4230)..(4482)
<223> OTHER INFORMATION: Agrobacterium Nopaline Synthase poly-A
      terminator.
<220> FEATURE:
<221> NAME/KEY: misc_feature
<222> LOCATION: (4564)..(4710)
<223> OTHER INFORMATION: Right T-DNA Border; similar to genbank#TIP37TD2
      Ti plasmid (from A. tumefaciens, nopaline strain T37) T-DNA 3'
      (right) border.
<220> FEATURE:
<221> NAME/KEY: misc_feature
<222> LOCATION: (4647)..(4670)
<223> OTHER INFORMATION: Right T-DNA Border repeat region; similar to
      #TIP37TD2; from pCambia2301.
<220> FEATURE:
<221> NAME/KEY: misc_feature
<222> LOCATION: (4875)..(5669)
<223> OTHER INFORMATION: nptII gene/CDS; confers Kanamycin resistance;
      99% homologous to #AY181092 Synthetic construct S1 promoter-nptII
      gene-S3 terminator cassette.
<220> FEATURE:
<221> NAME/KEY: rep_origin
<222> LOCATION: (5967)..(6648)
```

<223> OTHER INFORMATION: ColEI replication origin
<220> FEATURE:
<221> NAME/KEY: rep_origin
<222> LOCATION: (7057)..(9651)
<223> OTHER INFORMATION: pVS1 origin of replication

<400> SEQUENCE: 9

```
gtgattttgt gccgagctgc cggtcgggga gctgttggct ggctggtggc aggatatatt      60
gtggtgtaaa caaattgacg cttagacaac ttaataacac attgcggacg tctttaatgt     120
actgaattaa catccgtttg atacttgtct aaaattggct gatttcgagt gcatctatgc     180
ataaaaacaa tctaatgaca attattacca agcaggatcc tctagaattc ccgatctagt     240
aacatagatg acaccgcgcg cgataattta tcctagtttg cgcgctatat tttgttttct     300
atcgcgtatt aaatgtataa ttgcgggact ctaatcataa aaacccatct cataaataac     360
gtcatgcatt acatgttaat tattacatgc ttaacgtaat tcaacagaaa ttatatgata     420
atcatcgcaa gaccggcaac aggattcaat cttaagaaac tttattgcca atgtttgaa     480
cgatcgggga aattcgagct cgccggcgtc gacgatatcc tgcaggtcaa atctcggtga     540
cgggcaggac cggacggggc ggtaccggca ggctgaagtc cagctgccag aaacccacgt     600
catgccagtt cccgtgcttg aagccggccg cccgcagcat gccgcggggg gcatatccga     660
gcgcctcgtg catgcgcacg ctcggtcgt tgggcagccc gatgacagcg accacgctct     720
tgaagccctg tgcctccagg gacttcagca ggtgggtgta gagcgtggag cccagtcccg     780
tccgctggtg gcgggggag acgtacacgg tcgactcggc cgtccagtcg taggcgttgc     840
gtgccttcca ggggcccgcg taggcgatgc cggcgacctc gccgtccacc tcggcgacga     900
gccaggata gcgctcccgc agacggacga ggtcgtccgt ccactcctgc ggttcctgcg     960
gctcggtacg gaagttgacc gtgcttgtct cgatgtagtg gttgacgatg gtgcagaccg    1020
ccggcatgtc cgcctcggtg cacggcgga tgtcggccgg cgtcgttct gggctcatgg    1080
cgcgccagat ctggattgag agtgaatatg agactctaat tggataccga ggggaattta    1140
tggaacgtca gtggagcatt tttgacaaga aatatttgct agctgatagt gaccttaggc    1200
gactttttgaa cgcgcaataa tggtttctga cgtatgtgct tagctcatta aactccagaa    1260
acccgcggct gagtggctcc ttcaacgttg cggttctgtc agttccaaac gtaaaacggc    1320
ttgtcccgcg tcatcggcgg gggtcataac gtgactccct taattctccg ctcatgatct    1380
tgatcccctg cgccatcaga tccttggcgg caagaaagcc atccagttta ctttgcaggg    1440
cttcccaacc ttaccagagg gcgccccagc tggcaattcc ggttcgcttg ctgtccataa    1500
aaccgcccag tctagctatc gccatgtaag cccactgcaa gctacctgct ttctctttgc    1560
gcttgcgttt tcccttgtcc agatagccca gtagctgaca ttcatccggg gtcagcaccg    1620
tttctgcgga ctggctttct acgtgttccg cttcctttag cagcccttgc gccctgagtg    1680
cttgcggcag cgtgaagctt gctatcaact ttgtatcgaa aagttggctc cgaattcgcc    1740
cttagcttga ctagagaatt cgaatccaaa aattacggat atgaatatag gcatatccgt    1800
atccgaatta tccgtttgac agctagcaac gattgtacaa ttgcttcttt aaaaaaggaa    1860
gaaagaaaga aagaaaagaa tcaacatcag cgttaacaaa cggccccgtt acggcccaaa    1920
cggtcatata gagtaacggc gttaagcgtt gaaagactcc tatcgaaata cgtaaccgca    1980
aacgtgtcat agtcagatcc cctcttcctt caccgcctca aacacaaaaa taatcttcta    2040
cagcctatat atacaacccc ccttctatc tctcctttct cacaattcat catctttctt    2100
tctctacccc caatttttaag aaatcctctc ttctcctctt cattttcaag gtaaatctct    2160
```

```
ctctctctct ctctctctgt tattccttgt tttaattagg tatgtattat tgctagtttg    2220
ttaatctgct tatcttatgt atgccttatg tgaatatctt tatcttgttc atctcatccg    2280
tttagaagct ataaatttgt tgatttgact gtgtatctac acgtggttat gtttatatct    2340
aatcagatat gaatttcttc atattgttgc gtttgtgtgt accaatccga aatcgttgat    2400
ttttttcatt taatcgtgta gctaattgta cgtatacata tggatctacg tatcaattgt    2460
tcatctgttt gtgtttgtat gtatacagat ctgaaaacat cacttctctc atctgattgt    2520
gttgttacat acatagatat agatctgtta tatcattttt tttattaatt gtgtatatat    2580
atatgtgcat agatctggat tacatgattg tgattattta catgattttg ttatttacgt    2640
atgtatatat gtagatctgg acttttttgga gttgttgact tgattgtatt tgtgtgtgta    2700
tatgtgtgtt ctgatcttga tatgttatgt atgtgcagcc cggatcaagg gcgaattcga    2760
cccaagtttg tacaaaaaag caggctggcg cgccggatcc tcatctaagc gcaaagagac    2820
gtactatgga aaacgctaaa atgaactcgc tcatcgccca gtatccgttg gtaaaggatc    2880
tggttgctct taaagaaacc acctggttta atcctggcac gacctcattg gctgaaggtt    2940
taccttatgt tggcctgacc gaacaggatg ttcaggacgc ccatgcgcgc ttatcccgtt    3000
ttgcacccta tctggcaaaa gcatttcctg aaactgctgc cactgggggg attattgaat    3060
cagaactggt tgccattcca gctatgcaaa acggctgga aaagaatat cagcaaccga    3120 tcagcgggca actgttactg aaaaaagata gccatttgcc catttccggc tccataaaag    3180
cacgcggcgg gatttatgaa gtcctggcac acgcagaaaa actggctctg gaagcggggt    3240
tgctgacgct tgatgatgac tacagcaaac tgctttctcc ggagtttaaa cagttcttta    3300
gccaatacag cattgctgtg ggctcaaccg gaaatctggg gttatcaatc ggcattatga    3360
gcgcccgcat tggctttaag gtgacagttc atatgtctgc tgatgcccgg gcatggaaaa    3420
aagcgaaact gcgcagccat ggcgttacgg tcgtggaata tgagcaagat tatggtgttg    3480
ccgtcgagga aggacgtaaa gcagcgcagt ctgacccgaa ctgtttcttt attgatgacg    3540
aaaattcccg cacgttgttc cttgggtatt ccgtcgctgg ccagcgtctt aaagcgcaat    3600
ttgcccagca aggccgtatc gtcgatgctg ataaccctct gtttgtctat ctgccgtgtg    3660
gtgttggcgg tggtcctggt ggcgtcgcat tcgggcttaa actggcgttt ggcgatcatg    3720
ttcactgctt ttttgccgaa ccaacgcact cccttgtat gttgttaggc gtccatacag    3780
gattacacga tcagatttct gttcaggata ttggtatcga caaccttacc gcagcggatg    3840
gccttgcagt tggtcgcgca tcaggctttg tcgggcgggc aatggagcgt ctgctggatg    3900
gcttctatac ccttagcgat caaaccatgt atgacatgct tggctggctg gcgcaggaag    3960
aaggtattcg tcttgaacct tcggcactgg cgggtatggc cggacctcag cgcgtgtgtg    4020
catcagtaag ttaccaacag atgcacggtt tcagcgcaga acaactgcgt aataccactc    4080
atctggtgtg ggcgacggga ggtggaatgg tgccggaaga agagatgaat caatatctgg    4140
caaaaggccg ttaataacgt ttcaacgcag catggatcgt accgagctcc tgcagggggg    4200
acccagcttt cttgtacaaa gtggagctcg atcgttcaaa catttggcaa taaagtttct    4260
taagattgaa tcctgttgcc ggtcttgcga tgattatcat ataatttctg ttgaattacg    4320
ttaagcatgt aataattaac atgtaatgca tgacgttatt tatgagatgg ttttttatga    4380
ttagagtccc gcaattatac atttaatacg cgatagaaaa caaaatatag cgcgcaaact    4440
aggataaatt atcgcgcgcg gtgtcatcta tgttactaga tcggccggcc aactttatta    4500
tacatagttg ataagcgatc gcagcttggc gtaatcatgg tcatagctgt ttcctactag    4560
```

```
atctgattgt cgtttcccgc cttcagttta aactatcagt gtttgacagg atatattggc    4620
gggtaaacct aagagaaaag agcgtttatt agaataatcg gatatttaaa agggcgtgaa    4680
aaggtttatc cgttcgtcca tttgtatgtc catgtgtttt atggacagca agcgaaccgg    4740
aattgccagc tggggcgccc tctggtaagg ttgggaagcc ctgcaaagta aactggatgg    4800
cttttcttgcc gccaaggatc tgatggcgca ggggatcaag atctgatcaa gagacaggat    4860
gaggatcgtt tcgcatgatt gaacaagatg gattgcacgc aggttctccg gccgcttggg    4920
tggagaggct attcggctat gactgggcac aacagacaat cggctgctct gatgccgccg    4980
tgttccggct gtcagcgcag gggcgcccgg ttcttttttgt caagaccgac ctgtccggtg    5040
ccctgaatga actgcaggac gaggcagcgc ggctatcgtg gctggccacg acgggcgttc    5100
cttgcgcagc tgtgctcgac gttgtcactg aagcgggaag ggactggctg ctattgggcg    5160
aagtgccggg gcaggatctc ctgtcatccc accttgctcc tgccgagaaa gtatccatca    5220
tggctgatgc aatgcggcgg ctgcatacgc ttgatccggc tacctgccca ttcgaccacc    5280
aagcgaaaca tcgcatcgag cgagcacgta ctcggatgga agccggtctt gtcgatcagg    5340
atgatctgga cgaagagcat caggggctcg cgccagccga actgttcgcc aggctcaagg    5400
cgcgcatgcc cgacggcgag gatctcgtcg tgacccatgg cgatgcctgc ttgccgaata    5460
tcatggtgga aaatggccgc ttttctggat tcatcgactg tggccggctg ggtgtggcgg    5520
accgctatca ggacatagcg ttggctaccc gtgatattgc tgaagagctt ggcggcgaat    5580
gggctgaccg cttcctcgtg ctttacggta tcgccgctcc cgattcgcag cgcatcgcct    5640
tctatcgcct tcttgacgag ttcttctgaa ttgaaaaagg aagaatgcat gaccaaaatc    5700
ccttaacgtg agttttcgtt ccactgagcg tcagaccccg tagaaaagat caaaggatct    5760
tcttgagatc ctttttttct gcgcgtaatc tgctgcttgc aaacaaaaaa accaccgcta    5820
ccagcggtgg tttgtttgcc ggatcaagag ctaccaactc tttttccgaa ggtaactggc    5880
ttcagcagag cgcagatacc aaatactgtc cttctagtgt agccgtagtt aggccaccac    5940
ttcaagaact ctgtagcacc gcctacatac ctcgctctgc taatcctgtt accagtggct    6000
gctgccagtg gcgataagtc gtgtcttacc gggttggact caagacgata gttaccggat    6060
aaggcgcagc ggtcgggctg aacggggggt tcgtgcacac agcccagctt ggagcgaacg    6120
acctacaccg aactgagata cctacagcgt gagctatgag aaagcgccac gcttcccgaa    6180
gggagaaagg cggacaggta tccggtaagc ggcagggtcg gaacaggaga gcgcacgagg    6240
gagcttccag ggggaaacgc ctggtatctt tatagtcctg tcgggtttcg ccacctctga    6300
cttgagcgtc gatttttgtg atgctcgtca gggggcgga gcctatggaa aaacgccagc    6360
aacgcggcct ttttacggtt cctggccttt tgctggcctt tgctcacat gttctttcct    6420
gcgttatccc ctgattctgt ggataaccgt attaccgcct ttgagtgagc tgataccgct    6480
cgccgcagcc gaacgaccga gcgcagcgag tcagtgagcg aggaagcgga agagcgcctg    6540
atgcggtatt ttctccttac gcatctgtgc ggtatttcac accgcatatg gtgcactctc    6600
agtacaatct gctctgatgc cgcatagtta agccagtata cactccgcta tcgctacgtg    6660
actgggtcat ggctgcgccc cgacacccgc caacacccgc tgacgcgccc tgacgggctt    6720
gtctgctccc ggcatccgct tacagacaag ctgtgaccgt ctccgggagc tgcatgtgtc    6780
agaggttttc accgtcatca ccgaaacgcg cgaggcaggg tgccttgatg tgggcgccgg    6840
cggtcgagtg gcgacggcgc ggcttgtccg cgccctggta gattgcctgg ccgtaggcca    6900
gccattttg agcggccagc ggccgcgata ggccgacgcg aagcggcggg gcgtagggag    6960
```

```
cgcagcgacc gaagggtagg cgcttttgc agctcttcgg ctgtgcgctg ccagacagt    7020
tatgcacagg ccaggcgggt tttaagagtt ttaataagtt ttaaagagtt ttaggcggaa    7080
aaatcgcctt ttttctcttt tatatcagtc acttacatgt gtgaccggtt cccaatgtac    7140
ggctttgggt tcccaatgta cgggttccgg ttcccaatgt acggctttgg gttcccaatg    7200
tacgtgctat ccacaggaaa gagacctttt cgacctttt ccctgctag gcaatttgc    7260
cctagcatct gctccgtaca ttaggaaccg gcggatgctt cgccctcgat caggttgcgg    7320
tagcgcatga ctaggatcgg gccagcctgc cccgcctcct ccttcaaatc gtactccggc    7380
aggtcatttg acccgatcag cttgcgcacg gtgaaacaga acttcttgaa ctctccggcg    7440
ctgccactgc gttcgtagat cgtcttgaac aaccatctgg cttctgcctt gcctgcggcg    7500
cggcgtgcca ggcggtagag aaaacggccg atgccgggat cgatcaaaaa gtaatcgggg    7560
tgaaccgtca gcacgtccgg gttcttgcct tctgtgatct cgcggtacat ccaatcagct    7620
agctcgatct cgatgtactc cggccgcccg gtttcgctct ttacgatctt gtagcggcta    7680
atcaaggctt caccctcgga taccgtcacc aggcggccgt tcttggcctt cttcgtacgc    7740
tgcatggcaa cgtgcgtggt gtttaaccga atgcaggttt ctaccaggtc gtctttctgc    7800
tttccgccat cggctcgccg gcagaacttg agtacgtccg caacgtgtgg acggaacacg    7860
cggccgggct tgtctccctt cccttccggg tatcggttca tggattcggt tagatgggaa    7920
accgccatca gtaccaggtc gtaatcccac acactggcca tgccggccgg ccctgcggaa    7980
acctctacgt gcccgtctgg aagctcgtag cggatcacct cgccagctcg tcggtcacgc    8040
ttcgacagac ggaaaacggc cacgtccatg atgctgcgac tatcgcgggt gcccacgtca    8100
tagagcatcg gaacgaaaaa atctggttgc tcgtcgccct tgggcggctt cctaatcgac    8160
ggcgcaccgg ctgccggcgg ttgccgggat tctttgcgga ttcgatcagc ggccgcttgc    8220
cacgattcac cggggcgtgc ttctgcctcg atgcgttgcc gctgggcggc ctgcgcggcc    8280
ttcaacttct ccaccaggtc atcacccagc gccgcgccga tttgtaccgg gccggatggt    8340
ttgcgaccgc tcacgccgat tcctcgggct tggggggttcc agtgccattg cagggccggc    8400
agacaaccca gccgcttacg cctggccaac cgcccgttcc tccacacatg gggcattcca    8460
cggcgtcggt gcctggttgt tcttgatttt ccatgccgcc tcctttagcc gctaaaattc    8520
atctactcat ttattcattt gctcatttac tctggtagct gcgcgatgta ttcagatagc    8580
agctcggtaa tggtcttgcc ttggcgtacc gcgtacatct tcagcttggt gtgatcctcc    8640
gccggcaact gaaagttgac ccgcttcatg gctggcgtgt ctgccaggct ggccaacgtt    8700
gcagccttgc tgctgcgtgc gctcggacgg ccggcactta gcgtgtttgt gcttttgctc    8760
attttctctt tacctcatta actcaaatga gttttgattt aatttcagcg gccagcgcct    8820
ggacctcgcg ggcagcgtcg ccctcgggtt ctgattcaag aacggttgtg ccggcggcgg    8880
cagtgcctgg gtagctcacg cgctgcgtga tacgggactc aagaatgggc agctcgtacc    8940
cggccagcgc ctcggcaacc tcaccgccga tgcgcgtgcc tttgatcgcc cgcgacacga    9000
caaaggccgc ttgtagcctt ccatccgtga cctcaatgcg ctgcttaacc agctccacca    9060
ggtcggcggt ggcccatatg tcgtaagggc ttggctgcac cggaatcagc acgaagtcgg    9120
ctgccttgat cgcggacaca gccaagtccg ccgcctgggg cgctccgtcg atcactacga    9180
agtcgcgccg gccgatggcc ttcacgtcgc ggtcaatcgt cgggcggtcg atgccgacaa    9240
cggttagcgg ttgatcttcc cgcacggccg cccaatcgcg ggcactgccc tggggatcgg    9300
aatcgactaa cagaacatcg gccccggcga gttgcagggc gcgggctaga tgggttgcga    9360
```

```
tggtcgtctt gcctgacccg cctttctggt taagtacagc gataaccttc atgcgttccc    9420
cttgcgtatt tgtttattta ctcatcgcat catatacgca gcgaccgcat gacgcaagct    9480
gttttactca aatacacatc acctttttag acggcggcgc tcggtttctt cagcggccaa    9540
gctggccggc caggccgcca gcttggcatc agacaaaccg gccaggattt catgcagccg    9600
cacggttgag acgtgcgcgg gcggctcgaa cacgtacccg gccgcgatca tctccgcctc    9660
gatctcttcg gtaatgaaaa acggttcgtc ctggccgtcc tggtgcggtt tcatgcttgt    9720
tcctcttggc gttcattctc ggcggccgcc agggcgtcgg cctcggtcaa tgcgtcctca    9780
cggaaggcac cgcgccgcct ggcctcggtg ggcgtcactt cctcgctgcg ctcaagtgcg    9840
cggtacaggg tcgagcgatg cacgccaagc agtgcagccg cctctttcac ggtgcggcct    9900
tcctggtcga tcagctcgcg ggcgtgcgcg atctgtgccg gggtgagggt agggcggggg    9960
ccaaacttca cgcctcgggc cttggcggcc tcgcgcccgc tccgggtgcg gtcgatgatt   10020
agggaacgct cgaactcggc aatgccggcg aacacggtca acaccatgcg gccggccggc   10080
gtggtggtaa cgcgtg                                                   10096
```

<210> SEQ ID NO 10
<211> LENGTH: 6600
<212> TYPE: DNA
<213> ORGANISM: Artificial sequence
<220> FEATURE:
<223> OTHER INFORMATION: T-DNA of RLM274, a RLM407-type Bar-GUS Binary
      Vector: LB> <p-NOS::c-bar::t-NOS p-PcUBI::c-gusINT::t-NOS> RB>.
<220> FEATURE:
<221> NAME/KEY: misc_feature
<222> LOCATION: (1)..(215)
<223> OTHER INFORMATION: Left T-DNA border (full) similar to #TIP37TD1
      Ti plasmid (from A.tumefaciens, nopaline strain T37).
<220> FEATURE:
<221> NAME/KEY: misc_feature
<222> LOCATION: (47)..(71)
<223> OTHER INFORMATION: Left T-DNA Border repeat region; similar to
      #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
      poly-A terminator.
<220> FEATURE:
<221> NAME/KEY: misc_feature
<222> LOCATION: (527)..(1078)
<223> OTHER INFORMATION: Complement of BAR gene/CDS; 99% homologous to
      #SHBARPA Streptomyces hygroscopicus bar gene for phosphinothricin
      acetyl transferase; from QC25-3/EW105.
<220> FEATURE:
<221> NAME/KEY: promoter
<222> LOCATION: (1092)..(1379)
<223> OTHER INFORMATION: Complement of promoter from the noplaine
      synthase gene (Depicker et al. 1982, J.Mol.Appl.Genet. 1:561-573)
      EMBL no: V00087.
<220> FEATURE:
<221> NAME/KEY: promoter
<222> LOCATION: (1822)..(2817)
<223> OTHER INFORMATION: Parsley UBI4-2 promoter with internal intron;
      99% homology to #PCCUBI42 P.crispum gene Pcubi4-2 for
      polyubiquitin; from QC28-6/JB010.
<220> FEATURE:
<221> NAME/KEY: misc_feature
<222> LOCATION: (2843)..(4843)
<223> OTHER INFORMATION: gusINT CDS comprise of the E. coli gusA CDS
      containing and internal PIV2 intron.
<220> FEATURE:
<221> NAME/KEY: terminator
<222> LOCATION: (4914)..(5166)
<223> OTHER INFORMATION: Agrobacterium Nopaline Synthase poly-A
      terminator.
<220> FEATURE:
<221> NAME/KEY: misc_feature
<222> LOCATION: (5252)..(5397)

<223> OTHER INFORMATION: Right T-DNA Border; similar to genbank#TIP37TD2
    Ti plasmid (from A. tumefaciens, nopaline strain T37) T-DNA 3'
    (right) border.
<220> FEATURE:
<221> NAME/KEY: misc_feature
<222> LOCATION: (5292)..(5315)
<223> OTHER INFORMATION: Right T-DNA Border repeat region; similar to
    #TIP37TD2; from pCambia2301.

<400> SEQUENCE: 10

```
gtgattttgt gccgagctgc cggtcgggga gctgttggct ggctggtggc aggatatatt      60
gtggtgtaaa caaattgacg cttagacaac ttaataacac attgcggacg tcttttaatgt   120 actgaattaa catccgtttg atacttgtct aaaattggct gatttcgagt gcatctatgc    180
ataaaaacaa tctaatgaca attattacca agcaggatcc tctagaattc ccgatctagt    240
aacatagatg acaccgcgcg cgataattta tcctagtttg cgcgctatat tttgttttct    300
atcgcgtatt aaatgtataa ttgcgggact ctaatcataa aaacccatct cataaataac    360
gtcatgcatt acatgttaat tattacatgc ttaacgtaat tcaacagaaa ttatatgata    420
atcatcgcaa gaccggcaac aggattcaat cttaagaaac tttattgcca aatgtttgaa    480
cgatcgggga aattcgagct cgccggcgtc gacgatatcc tgcaggaatc ccgccctaca   540
acttcgactc ccgcgccgcg ccgtggtacc gctggaacgc ctcgtcgacg agctgcgcga    600
catcctccgc cgcgccccaa ctctgctggt atcccgcact cgagaagcca tacgcatgca    660
caagcgtgac ctccttctcc ttcgccgctc gtgcgctgcc cctgccgagc gagaggggcg    720
actttgtccg gtcgagaggc aggacgatcc gttctgcctc aacgcggggt ccgcctcgtc    780
gtgcaggtcg caagccgacg ttgtggcgga ggacctcgat gccttcgatc gttccgtcgc    840
tcgagatggt cgggtcgagg cgcaagcagt gcttgaggat ccgctggacc gtctctgggt    900
tgacagacaa gtcccagtct cccacgccgt acgtcccgcc gcagatgact tcgccacctg    960 gtcgggaat gatgtaggcg ggagaagcgg ggtcggacga gtccatcgtg catcgcttgc    1020
atggggactt gacgaggacg gtttgcccgc ggattggctc ggcggcttgg tcgtcgatgc    1080
ccgcaatcga cttggcgcca agtcccgtag cgttgaccac caaatccgca ccgtcgaacg    1140
cctgctcaag cgacgtaacg gtccgtctct caaacgtcgc gccgagcttc tgcagctctc    1200
ttgcaaggta ctggcagtac tttggtgcgt ggacggagag ggtgtcgtag gttacgccga    1260
tagcgccagg tggacattcg gaagatggga ggggcggta atttggcgtg atgtccttgt    1320
accagtgccc gagcaagccg tcttcgttct gcgcgaaccg cctcgtcccc ttgagccaca    1380
tggcatggcc cgtcgggacc aactcgaccc acttcttgaa agtcgattct tcccattttg    1440
cttgtcgagg accgtctgta agcgtcatga aaggcgtcca attcgcgcca gcccatggtg    1500
aagcgaaagt ctggctcgag acgtcctccg gcaagtcgcg cgcgagaata tgcacgctgt    1560
agcccttccg agcgaggatg agggcgctgc tcagaccgat aacgcctgat ccgaggacaa    1620
cgacgcgctt ctgcgagtgc atggtggccc gggatccggc gcgccttttt tttatgagct    1680
gcaaacacac aaaagagtt caatacagtc aaataaaccc tgattgaatc agaaatagct    1740
ttctgttcaa cgtacgacac tacaaatcct aaagtttcga agaatctata cacaaacttc    1800
atctaacctt aaacagtgtt cagattcaat ctaacattga cagtgttcag attcaatcta    1860
acttcaacag ttcagatttc aattcacata tacaaatcat ttcccaggta acatgaacat    1920
ggatctctcc atcaaggtca agccaaattc tggtagctat aatcgagcta actgatcggt    1980
caacttagat cgattctagt aaaaccaaaa gatttagtgg aggttcacag atccaaatta    2040
aacgaattcc agatctcaag gaaattgaga aaacaagatc gagatccagc aaataaagta    2100
```

```
gatccagaaa gttcctatta ccttggaaag aaagagcgga agaagatgag attgaggaag    2160
attcaaaacg gagaatgaat ctcctggatt atctcttact ttctctctta gtcttcttcc    2220
ttgttcttct ctgtcaagtc gccggagatt caaaacggct gatgaaagtg aggaggacaa    2280
cgagacaatt caaagcggag aggaaaatat atgaatttat ataggcgggt ttatctctta    2340
caactttatt ttcggccttt caaaaaaata attaaaatcg acagacacga atcatttcga    2400
ccacaggtaa agataacgtg acctggctgt cagacagcct ttttcctcgt gttaactaat    2460
ttttaaacta attaatcatc tcagcccttg gattagttct tttgctttga tggcttcatg    2520
actgtgacct gctcgatccg cgtgttacat gacagctccg ttttttttagt ggttaactta    2580 aaccgagtca atccaggcaa cgttagtcgt cgtcgtggtt ggcttgttca attagatttc    2640
atacaattca acgtaattta attcgttttc tattagaatt gtatcataat taattcagac    2700
cgtgaaagaa agtgtctttc atgatgtgtt tatggatatt tatacaataa gatacaatgt    2760
ttcatcatat tcactattca cgattagtat gtacattaaa taatggctac tactacatcc    2820
gaactcgtca aaacgattct gaatcaatta tacatatgct gactcttgca tacataaaaa    2880
atagttgttt aaattttgtc taactaatgt ttggtataag tataatgttg agttgagata    2940
ccaattacat cgagtctagc cattttgtcg tgccatattc gtcaaaactt tcttacataa    3000
tgataaccta gatctagatg agatatgtat caatgtattt gagatcataa ttaagttcgt    3060
tctaaatttt gtcgaaacca acgcaagctt gactagagaa ttcgaatcca aaaattacgg    3120
atatgaatat aggcatatcc gtatccgaat tatccgtttg acagctagca acgattgtac    3180
aattgcttct ttaaaaaagg aagaaagaaa gaaagaaaag aatcaacatc agcgttaaca    3240
aacggccccg ttacggccca aacggtcata tagagtaacg gcgttaagcg ttgaaagact    3300
cctatcgaaa tacgtaaccg caaacgtgtc atagtcagat cccctcttcc ttcaccgcct    3360
caaacacaaa aataatcttc tacagcctat atatacaacc cccccttcta tctctccttt    3420
ctcacaattc atcatctttc tttctctacc cccaattttta agaaatcctc tcttctcctc    3480
ttcattttca aggtaaatct ctctctctct ctctctctct gttattcctt gtttttaatta    3540 ggtatgtatt attgctagtt tgttaatctg cttatcttat gtatgcctta tgtgaatatc    3600
tttatcttgt tcatctcatc cgtttagaag ctataaattt gttgatttga ctgtgtatct    3660
acacgtggtt atgtttatat ctaatcagat atgaatttct tcatattgtt gcgtttgtgt    3720
gtaccaatcc gaaatcgttg attttttttca tttaatcgtg tagctaattg tacgtataca    3780
tatggatcta cgtatcaatt gttcatctgt ttgtgttttgt atgtatacag atctgaaaac    3840
atcacttctc tcatctgatt gtgttgttac atacatagat atagatctgt tatatcattt    3900
tttttattaa ttgtgtatat atatatgtgc atagatctgg attacatgat tgtgattatt    3960
tacatgattt tgttatttac gtatgtatat atgtagatct ggactttttg gagttgttga    4020
cttgattgta tttgtgtgtg tatatgtgtg ttctgatctt gatatgttat gtatgtgcag    4080
cccggatctc cgggtaggtc agtccccttat gttacgtcct gtagaaaccc caacccgtga    4140
aatcaaaaaa ctcgacggcc tgtgggcatt cagtctggat cgcgaaaact gtggaattgg    4200
tcagcgttgg tgggaaagcg cgttacaaga aagccgggca attgctgtgc caggcagttt    4260
taacgatcag ttcgccgatg cagatattcg taattatgcg gcaacgtct ggtatcagcg    4320 cgaagtcttt ataccgaaag gttgggcagg ccagcgtatc gtgctgcgtt tcgatgcggt    4380
cactcattac ggcaaagtgt gggtcaataa tcaggaagtg atggagcatc agggcggcta    4440
tacgccattt gaagccgatg tcacgccgta tgttattgcc gggaaaagtg tacgtaagtt    4500
```

```
tctgcttcta cctttgatat atatataata attatcatta attagtagta atataatatt    4560
tcaaatattt ttttcaaaat aaaagaatgt agtatatagc aattgctttt ctgtagttta    4620
taagtgtgta tattttaatt tataacttttt ctaatatatg accaaaattt gttgatgtgc   4680
aggtatcacc gtttgtgtga acaacgaact gaactggcag actatcccgc cgggaatggt    4740
gattaccgac gaaaacggca agaaaaagca gtcttacttc catgatttct ttaactatgc    4800
cggaatccat cgcagcgtaa tgctctacac cacgccgaac acctgggtgg acgatatcac    4860
cgtggtgacg catgtcgcgc aagactgtaa ccacgcgtct gttgactggc aggtggtggc    4920
caatggtgat gtcagcgttg aactgcgtga tgcggatcaa caggtggttg caactggaca    4980
aggcactagc gggactttgc aagtggtgaa tccgcacctc tggcaaccgg gtgaaggtta    5040
tctctatgaa ctgtgcgtca cagccaaaag ccagacagag tgtgatatct acccgcttcg    5100
cgtcggcatc cggtcagtgg cagtgaaggg cgaacagttc ctgattaacc acaaaccgtt    5160
ctactttact ggctttggtc gtcatgaaga tgcggacttg cgtggcaaag gattcgataa    5220
cgtgctgatg gtgcacgacc acgcattaat ggactggatt ggggccaact cctaccgtac    5280
ctcgcattac ccttacgctg aagagatgct cgactgggca gatgaacatg gcatcgtggt    5340
gattgatgaa actgctgctg tcggctttaa cctctcttta ggcattggtt tcgaagcggg    5400
caacaagccg aaagaactgt acagcgaaga ggcagtcaac ggggaaactc agcaagcgca    5460
cttacaggcg attaaagagc tgatagcgcg tgacaaaaac cacccaagcg tggtgatgtg    5520
gagtattgcc aacgaaccgg ataccgtcc gcaaggtgca cggaatatt tcgcgccact     5580 ggcggaagca acgcgtaaac tcgacccgac gcgtccgatc acctgcgtca atgtaatgtt    5640
ctgcgacgct cacaccgata ccatcagcga tctctttgat gtgctgtgcc tgaaccgtta    5700
ttacggatgg tatgtccaaa gcggcgattt ggaaacggca gagaaggtac tggaaaaaga    5760
acttctggcc tggcaggaga aactgcatca gccgattatc atcaccgaat acggcgtgga    5820
tacgttagcc gggctgcact caatgtacac cgacatgtgg agtgaagagt atcagtgtgc    5880
atggctggat atgtatcacc gcgtctttga tcgcgtcagc gccgtcgtcg gtgaacaggt    5940
atggaatttc gccgattttg cgacctcgca aggcatattg cgcgttggcg gtaacaagaa    6000
agggatcttc actcgcgacc gcaaaccgaa gtcggcggct tttctgctgc aaaaacgctg    6060
gactggcatg aacttcggtg aaaaaccgca gcagggaggc aaacaatgaa tcaacaactc    6120
tcctggcgca ccatcgtcgg ctacagcctc gggaattgct accgagctcg aatttccccg    6180
atcgttcaaa catttggcaa taaagtttct taagattgaa tcctgttgcc ggtcttgcga    6240
tgattatcat ataatttctg ttgaattacg ttaagcatgt aataattaac atgtaatgca    6300
tgacgttatt tatgagatgg gttttatga ttagagtccc gcaattatac atttaatacg    6360
cgatagaaaa caaatatag cgcgcaaact aggataaatt atcgcgcgcg gtgtcatcta    6420
tgttactaga tcgggaattg gcgatcgcag cttggcgtaa tcatggtcat agctgtttcc    6480
tactagatct gattgtcgtt tcccgccttc agtttaaact atcagtgttt gacaggatat    6540
attggcgggt aaacctaaga gaaaagagcg tttattagaa taatcggata tttaaaaggg    6600
```

<210> SEQ ID NO 11
<211> LENGTH: 6820
<212> TYPE: DNA
<213> ORGANISM: Artificial sequence
<220> FEATURE:
<223> OTHER INFORMATION: T-DNA of RLM254, a RLM407-type Selda-GUS Binary
     Vector: LB> <p-sTPT::c-dsdA/na::t-NOS p-PcUBI::c-gusINT::t-NOS>
     RB>.

```
<220> FEATURE:
<221> NAME/KEY: misc_feature
<222> LOCATION: (1)..(215)
<223> OTHER INFORMATION: Left T-DNA border (full) similar to #TIP37TD1
      Ti plasmid (from A.tumefaciens, nopaline strain T37).
<220> FEATURE:
<221> NAME/KEY: misc_feature
<222> LOCATION: (47)..(71)
<223> OTHER INFORMATION: Left T-DNA Border repeat region; similar to
      #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
      poly-A terminator.
<220> FEATURE:
<221> NAME/KEY: misc_feature
<222> LOCATION: (561)..(1329)
<223> OTHER INFORMATION: Complement of CDS for E.coli D-serine
      dehydratase; GenBank Acc.-No.: J01603.
<220> FEATURE:
<221> NAME/KEY: promoter
<222> LOCATION: (1913)..(3230)
<223> OTHER INFORMATION: Complement of short Triose Phosphate
      Translocator [sTPT] promoter.
<220> FEATURE:
<221> NAME/KEY: promoter
<222> LOCATION: (3273)..(4268)
<223> OTHER INFORMATION: Parsley UBI4-2 promoter with internal intron;
      99% homology to #PCCUBI42 P.crispum gene Pcubi4-2 for
      polyubiquitin; from QC28-6/JB010.
<220> FEATURE:
<221> NAME/KEY: misc_feature
<222> LOCATION: (4294)..(6294)
<223> OTHER INFORMATION: gusINT CDS comprise of the E. coli gusA CDS
      containing and internal PIV2 intron.
<220> FEATURE:
<221> NAME/KEY: terminator
<222> LOCATION: (6365)..(6617)
<223> OTHER INFORMATION: Agrobacterium Nopaline Synthase poly-A
      terminator.
<220> FEATURE:
<221> NAME/KEY: misc_feature
<222> LOCATION: (6676)..(6820)
<223> OTHER INFORMATION: Right T-DNA Border; similar to genbank#TIP37TD2
      Ti plasmid (from A. tumefaciens, nopaline strain T37) T-DNA 3'
      (right) border.
<220> FEATURE:
<221> NAME/KEY: misc_feature
<222> LOCATION: (6758)..(6781)
<223> OTHER INFORMATION: Right T-DNA Border repeat region; similar to
      #TIP37TD2; from pCambia2301.

<400> SEQUENCE: 11
gtgattttgt gccgagctgc cggtcgggga gctgttggct ggctggtggc aggatatatt      60
gtggtgtaaa caaattgacg cttagacaac ttaataacac attgcggacg tctttaatgt     120
actgaattaa catccgtttg atacttgtct aaaattggct gatttcgagt gcatctatgc     180
ataaaaacaa tctaatgaca attattacca agcaggatcc tctagaattc ccgatctagt     240
aacatagatg acaccgcgcg cgataattta tcctagtttg cgcgctatat tttgttttct     300
atcgcgtatt aaatgtataa ttgcgggact ctaatcataa aaacccatct cataaataac     360
gtcatgcatt acatgttaat tattacatgc ttaacgtaat tcaacagaaa ttatatgata     420
atcatcgcaa gaccggcaac aggattcaat cttaagaaac tttattgcca aatgtttgaa     480
cgatcgggga aattcgagct cgccggcgtc gacgatatcc tgcaggagct cggtacgatc     540
catgctgcgt tgaaacgtta ttaacggcct tttgccagat attgattcat ctcttcttcc     600
ggcaccattc cacctcccgt cgcccacacc agatgagtgg tattacgcag ttgttctgcg     660
ctgaaaccgt gcatctgttg gtaacttact gatgcacaca cgcgctgagg tccggccata     720
cccgccagtg ccgaaggttc aagacgaata ccttcttcct gcgccagcca gccaagcatg     780
```

-continued

```
tcatacatgg tttgatcgct aagggtatag aagccatcca gcagacgctc cattgcccgc    840
ccgacaaagc ctgatgcgcg accaactgca aggccatccg ctgcggtaag gttgtcgata    900
ccaatatcct gaacagaaat ctgatcgtgt aatcctgtat ggacgcctaa caacatacaa    960
ggggagtgcg ttggttcggc aaaaaagcag tgaacatgat cgccaaacgc cagtttaagc   1020
ccgaatgcga cgccaccagg accaccgcca acaccacacg gcagatagac aaacagaggg   1080
ttatcagcat cgacgatacg gccttgctgg gcaaattgcg ctttaagacg ctggccagcg   1140
acggaatacc caaggaacaa cgtgcgggaa ttttcgtcat caataaagaa acagttcggg   1200
tcagactgcg ctgctttacg tccttcctcg acggcaacac cataatcttg ctcatattcc   1260
acgaccgtaa cgccatggct gcgcagtttc gcttttttcc atgcccgggc atcagcagac   1320
atatgaactg tcaccttaaa gccaatgcgg gcgctcataa tgccgattga taaccccaga   1380
tttccggttg agcccacagc aatgctgtat tggctaaaga actgtttaaa ctccggagaa   1440
agcagtttgc tgtagtcatc atcaagcgtc agcaaccccg cttccagagc cagttttttct  1500 gcgtgtgcca ggacttcata aatcccgccg cgtgctttta tggagccgga aatgggcaaa   1560
tggctatctt ttttcagtaa cagttgcccg ctgatcggtt gctgatattc tttttccagc   1620 cgttttttgca tagctggaat ggcaaccagt tctgattcaa taatcccccc agtggcagca   1680
gtttcaggaa atgcttttgc cagatagggt gcaaaacggg ataagcgcgc atgggcgtcc   1740
tgaacatcct gttcggtcag gccaacataa ggtaaacctt cagccaatga ggtcgtgcca   1800
ggattaaacc aggtggtttc tttaagagca accagatcct ttaccaacgg atactgggcg   1860
atgagcgagt tcattttagc gttttccatg gtacccagac gtcgactcta gatgaaatcg   1920
aaattcagag ttttgatagt gagagcaaag agggacggac ttatgaggat ttcgagtatt   1980
tcaagagatg gtacttgttg atcggacggc tacgatgatc tcgatttggt taatccagta   2040
tctcgcggtg tatggagtta tggtagggtt aatggtcaat ttcatctaac ggtagagaat   2100
gatgtaatta gataagaatc ttgagatact ggtttagatt ggatgagtgt agggtccatc   2160
ttatcttgat aagtggatgg ttttagaga cacagtgaat attagccaat cgaagttcca   2220
tatcaccatc atcatctgta aattttgtt tttttggaag ataataatga ttgaaatttt   2280
ggtagatttt attttcatt atttaccttg tatgttgagt ggtcttcaaa ttattgaacg   2340
tgacagattc acaagaaagt agattttta taaatgaaat tttacttatt ttaaaggtat   2400
ctctatttaa tttcttttgt ttatggttgt ctgtcagcat ttgacttgca gtttcatgct   2460
catagtcata tacgttattc taggcttttt tgaatatctt attactttt tcgtaataca   2520 attttataat tttatcaaag ttatacaact ataactaaaa ttagggtttt ctacaaaaca   2580
aaaaaatctt ctaattttt ttgttgtagc cagtttactc gtaagttaca aaaaaataca   2640
aatgaaccca catgtattat gcgtttaact aggattacca tgtactttca tgtactcaat   2700
tcaccctata ctctttttt tttttttct agttccaccc aatctataaa attctgtcca   2760
tttgaccaaa ttcaattaat ttctgtaatt gcgatttaaa attaatatta catgttcact   2820
atttctcgat tgagggaac ccgagtttaa atatgataaa aatgttgacc catcactaca   2880
aatatgttat agtttatact taatagtggt gttttgggg ataattgatg aattaagtaa   2940
acatgattct tcttatgaag ttgattgagt gattattgta tgtaaaccta tgtgattgat   3000
gttattggtt gattgagtga ttattgtatt agtatgtaag caaagatgat tgttcttatg   3060
aggtaatttg ttactcattc atcctttgc atatgagaaa ttgtgttagc gtacgcaaaa   3120
caatagagaa cataaaagat atgtgtattt atttaaggtg acttttgtta atgatattgt   3180
```

-continued

```
agtatctata catttatata taacttgttg aatttgagta taagctatca ggatccgggg   3240
gatcctctag agtcgacctg caggcatgca agcttgacta gagaattcga atccaaaaat   3300
tacggatatg aatataggca tatccgtatc cgaattatcc gtttgacagc tagcaacgat   3360
tgtacaattg cttctttaaa aaaggaagaa agaaagaaag aaaagaatca acatcagcgt   3420
taacaaacgg ccccgttacg gcccaaacgg tcatatagag taacggcgtt aagcgttgaa   3480
agactcctat cgaaatacgt aaccgcaaac gtgtcatagt cagatcccct cttccttcac   3540
cgcctcaaac acaaaaataa tcttctacag cctatatata caaccccccc ttctatctct   3600
cctttctcac aattcatcat ctttctttct ctacccccaa ttttaagaaa tcctctcttc   3660
tcctcttcat tttcaaggta aatctctctc tctctctctc tctctgttat tccttgtttt   3720
aattaggtat gtattattgc tagtttgtta atctgcttat cttatgtatg ccttatgtga   3780
atatctttat cttgttcatc tcatccgttt agaagctata aatttgttga tttgactgtg   3840
tatctacacg tggttatgtt tatatctaat cagatatgaa tttcttcata ttgttgcgtt   3900
tgtgtgtacc aatccgaaat cgttgatttt tttcatttaa tcgtgtagct aattgtacgt   3960
atacatatgg atctacgtat caattgttca tctgtttgtg tttgtatgta tacagatctg   4020
aaaacatcac ttctctcatc tgattgtgtt gttacataca tagatataga tctgttatat   4080
catttttttt attaattgtg tatatatata tgtgcataga tctggattac atgattgtga   4140
ttatttacat gattttgtta tttacgtatg tatatatgta gatctggact ttttggagtt   4200
gttgacttga ttgtatttgt gtgtgtatat gtgtgttctg atcttgatat gttatgtatg   4260
tgcagcccgg atctccgggt aggtcagtcc cttatgttac gtcctgtaga aaccccaacc   4320
cgtgaaatca aaaaactcga cggcctgtgg gcattcagtc tggatcgcga aaactgtgga   4380
attggtcagc gttggtggga aagcgcgtta caagaaagcc gggcaattgc tgtgccaggc   4440
agttttaacg atcagttcgc cgatgcagat attcgtaatt atgcgggcaa cgtctggtat   4500
cagcgcgaag tctttatacc gaaaggttgg gcaggccagc gtatcgtgct gcgtttcgat   4560
gcggtcactc attacggcaa agtgtgggtc aataatcagg aagtgatgga gcatcagggc   4620
ggctatacgc catttgaagc cgatgtcacg ccgtatgtta ttgccgggaa aagtgtacgt   4680
aagtttctgc ttctaccttt gatatatata taataattat cattaattag tagtaatata   4740
atatttcaaa tattttttc aaaataaaag aatgtagtat atagcaattg cttttctgta   4800
gtttataagt gtgtatattt taatttataa cttttctaat atatgaccaa aatttgttga   4860
tgtgcaggta tcaccgtttg tgtgaacaac gaactgaact ggcagactat cccgccggga   4920
atggtgatta ccgacgaaaa cggcaagaaa aagcagtctt acttccatga tttctttaac   4980
tatgccggaa tccatcgcag cgtaatgctc tacaccacgc cgaacacctg ggtggacgat   5040
atcaccgtgg tgacgcatgt cgcgcaagac tgtaaccacg cgtctgttga ctggcaggtg   5100
gtggccaatg gtgatgtcag cgttgaactg cgtgatgcgg atcaacaggt ggttgcaact   5160
ggacaaggca ctagcgggac tttgcaagtg gtgaatccgc acctctggca accgggtgaa   5220
ggttatctct atgaactgtg cgtcacagcc aaaagccaga cagagtgtga tatctacccg   5280
cttcgcgtcg gcatccggtc agtggcagtg aagggcgaac agttcctgat taaccacaaa   5340
ccgttctact ttactggctt tggtcgtcat gaagatgcgg acttgcgtgg caaaggattc   5400
gataacgtgc tgatggtgca cgaccacgca ttaatggact ggattggggc caactcctac   5460
cgtacctcgc attaccctta cgctgaagag atgctcgact gggcagatga acatggcatc   5520
gtggtgattg atgaaactgc tgctgtcggc tttaacctct ctttaggcat tggtttcgaa   5580
```

```
gcgggcaaca agccgaaaga actgtacagc gaagaggcag tcaacgggga aactcagcaa    5640
gcgcacttac aggcgattaa agagctgata gcgcgtgaca aaaaccaccc aagcgtggtg    5700
atgtggagta ttgccaacga accggatacc cgtccgcaag gtgcacggga atatttcgcg    5760
ccactggcgg aagcaacgcg taaactcgac ccgacgcgtc cgatcacctg cgtcaatgta    5820
atgttctgcg acgctcacac cgataccatc agcgatctct tgatgtgct gtgcctgaac    5880 cgttattacg gatggtatgt ccaaagcggc gatttggaaa cggcagagaa ggtactggaa    5940
aaagaacttc tggcctggca ggagaaactg catcagccga ttatcatcac cgaatacggc    6000
gtggatacgt tagccgggct gcactcaatg tacaccgaca tgtggagtga agagtatcag    6060
tgtgcatggc tggatatgta tcaccgcgtc tttgatcgcg tcagcgccgt cgtcggtgaa    6120
caggtatgga atttcgccga ttttgcgacc tcgcaaggca tattgcgcgt tggcggtaac    6180
aagaaaggga tcttcactcg cgaccgcaaa ccgaagtcgg cggcttttct gctgcaaaaa    6240
cgctggactg gcatgaactt cggtgaaaaa ccgcagcagg gaggcaaaca atgaatcaac    6300
aactctcctg gcgcaccatc gtcggctaca gcctcgggaa ttgctaccga gctcgaattt    6360
ccccgatcgt tcaaacattt ggcaataaag tttcttaaga ttgaatcctg ttgccggtct    6420
tgcgatgatt atcatataat ttctgttgaa ttacgttaag catgtaataa ttaacatgta    6480
atgcatgacg ttatttatga gatgggtttt tatgattaga gtcccgcaat tatacattta    6540
atacgcgata gaaaacaaaa tatagcgcgc aaactaggat aaattatcgc gcgcggtgtc    6600
atctatgtta ctagatcggg aattggcgat cgcagcttgg cgtaatcatg gtcatagctg    6660
tttcctacta gatctgattg tcgtttcccg ccttcagttt aaactatcag tgtttgacag    6720
gatatattgg cgggtaaacc taagagaaaa gagcgtttat tagaataatc ggatatttaa    6780
aagggcgtga aaaggtttat ccgttcgtcc atttgtatgt                          6820
```

<210> SEQ ID NO 12
<211> LENGTH: 5246
<212> TYPE: DNA
<213> ORGANISM: Artificial sequence
<220> FEATURE:
<223> OTHER INFORMATION: T-DNA of REW8, a RLM407-type Bar-GUS Binary
    Vector: LB> <p-NOS::c-bar::t-NOS p-PcUBI::c-gusINT::t-NOS> RB>.
<220> FEATURE:
<221> NAME/KEY: misc_feature
<222> LOCATION: (1)..(215)
<223> OTHER INFORMATION: Left T-DNA border (full) similar to #TIP37TD1
    Ti plasmid (from A.tumefaciens, nopaline strain T37).
<220> FEATURE:
<221> NAME/KEY: misc_feature
<222> LOCATION: (47)..(71)
<223> OTHER INFORMATION: Left T-DNA Border repeat region; similar to
    #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
    poly-A terminator.
<220> FEATURE:
<221> NAME/KEY: misc_feature
<222> LOCATION: (527)..(1078)
<223> OTHER INFORMATION: Complement of BAR gene/CDS; 100% homologous to
    #SHBARPA Streptomyces hygroscopicus bar gene for phosphinothricin
    acetyl transferase.
<220> FEATURE:
<221> NAME/KEY: promoter
<222> LOCATION: (1092)..(1379)
<223> OTHER INFORMATION: Complement of promoter from the noplaine
    synthase gene (Depicker et al. 1982, J.Mol.Appl.Genet. 1:561-573)
    EMBL no: V00087.
<220> FEATURE:
<221> NAME/KEY: promoter
<222> LOCATION: (1698)..(2693)
<223> OTHER INFORMATION: Parsley UBI4-2 promoter with internal intron; 99% homology to #PCCUBI42 P.crispum gene Pcubi4-2 for polyubiquitin; from QC28-6/JB010.
<220> FEATURE:
<221> NAME/KEY: misc_feature
<222> LOCATION: (2719)..(4719)
<223> OTHER INFORMATION: gusINT CDS comprise of the E. coli gusA CDS containing and internal PIV2 intron.
<220> FEATURE:
<221> NAME/KEY: terminator
<222> LOCATION: (4790)..(5042)
<223> OTHER INFORMATION: Agrobacterium Nopaline Synthase poly-A terminator.
<220> FEATURE:
<221> NAME/KEY: misc_feature
<222> LOCATION: (5101)..(5246)
<223> OTHER INFORMATION: Right T-DNA Border; similar to genbank#TIP37TD2 Ti plasmid (from A. tumefaciens, nopaline strain T37) T-DNA 3' (right) border.
<220> FEATURE:
<221> NAME/KEY: misc_feature
<222> LOCATION: (5183)..(5206)
<223> OTHER INFORMATION: Right T-DNA Border repeat region; similar to #TIP37TD2; from pCambia2301.

<400> SEQUENCE: 12

```
gtgattttgt gccgagctgc cggtcgggga gctgttggct ggctggtggc aggatatatt    60
gtggtgtaaa caaattgacg cttagacaac ttaataacac attgcggacg tctttaatgt   120
actgaattaa catccgtttg atacttgtct aaaattggct gatttcgagt gcatctatgc   180
ataaaaacaa tctaatgaca attattacca agcaggatcc tctagaattc ccgatctagt   240
aacatagatg acaccgcgcg cgataattta tcctagtttg cgcgctatat tttgttttct   300
atcgcgtatt aaatgtataa ttgcgggact ctaatcataa aaacccatct cataaataac   360
gtcatgcatt acatgttaat tattacatgc ttaacgtaat tcaacagaaa ttatatgata   420
atcatcgcaa gaccggcaac aggattcaat cttaagaaac tttattgcca aatgtttgaa   480
cgatcgggga aattcgagct cgccggcgtc gacgatatcc tgcaggtcaa atctcggtga   540
cgggcaggac cggacggggc ggtaccggca ggctgaagtc cagctgccag aaacccacgt   600
catgccagtt cccgtgcttg aagccggccg cccgcagcat gccgcggggg gcatatccga   660
gcgcctcgtg catgcgcacg ctcgggtcgt tgggcagccc gatgacagcg accacgctct   720
tgaagccctg tgcctccagg gacttcagca ggtgggtgta gagcgtggag cccagtcccg   780
tccgctggtg gcgggggggag acgtacacgg tcgactcggc cgtccagtcg taggcgttgc   840
gtgccttcca ggggcccgcg taggcgatgc cggcgacctc gccgtccacc tcggcgacga   900
gccagggata gcgctcccgc agacggacga ggtcgtccgt ccactcctgc ggttcctgcg   960
gctcggtacg gaagttgacc gtgccttgtct cgatgtagtg gttgacgatg gtgcagaccg  1020
ccggcatgtc cgcctcggtg gcacggcgga tgtcggccgg gcgtcgttct gggctcatgg  1080
cgcgccagat ctggattgag agtgaatatg agactctaat tggataccga ggggaattta  1140
tggaacgtca gtggagcatt tttgacaaga aatatttgct agctgatagt gaccttaggc  1200
gacttttgaa cgcgcaataa tggtttctga cgtatgtgct tagctcatta aactccagaa  1260
acccgcggct gagtggctcc ttcaacgttg cggttctgtc agttccaaac gtaaacggc   1320
ttgtcccgcg tcatcggcgg gggtcataac gtgactccct taattctccg ctcatgatct  1380
tgatcccctg cgccatcaga tccttggcgg caagaaagcc atccagttta ctttgcaggg  1440
cttcccaacc ttaccagagg gcgccccagc tggcaattcc ggttcgcttg ctgtccataa  1500
aaccgcccag tctagctatc gccatgtaag cccactgcaa gctacctgct ttctctttgc  1560
```

```
gcttgcgttt tcccttgtcc agatagccca gtagctgaca ttcatccggg gtcagcaccg    1620
tttctgcgga ctggctttct acgtgttccg cttcctttag cagcccttgc gccctgagtg    1680
cttgcggcag cgtgaagctt gactagagaa ttcgaatcca aaaattacgg atatgaatat    1740
aggcatatcc gtatccgaat tatccgtttg acagctagca acgattgtac aattgcttct    1800 ttaaaaagg aagaaagaaa gaaagaaaag aatcaacatc agcgttaaca acggccccg     1860 ttacggccca acggtcata tagagtaacg gcgttaagcg ttgaaagact cctatcgaaa     1920
tacgtaaccg caaacgtgtc atagtcagat cccctcttcc ttcaccgcct caaacacaaa    1980
aataatcttc tacagcctat atatacaacc ccccttcta tctctccttt ctcacaattc     2040
atcatctttc tttctctacc cccaatttta agaaatcctc tcttctcctc ttcattttca    2100
aggtaaatct ctctctctct ctctctctct gttattcctt gttttaatta ggtatgtatt    2160
attgctagtt tgttaatctg cttatcttat gtatgcctta tgtgaatatc tttatcttgt    2220
tcatctcatc cgtttagaag ctataaattt gttgatttga ctgtgtatct acacgtggtt    2280
atgtttatat ctaatcagat atgaatttct tcatattgtt gcgtttgtgt gtaccaatcc    2340
gaaatcgttg atttttttca tttaatcgtt tagctaattg tacgtataca tatggatcta    2400
cgtatcaatt gttcatctgt ttgtgtttgt atgtatacag atctgaaaac atcacttctc    2460
tcatctgatt gtgttgttac atacatagat atagatctgt tatatcattt ttttattaa    2520 ttgtgtatat atatatgtgc atagatctgg attacatgat tgtgattatt tacatgattt    2580
tgttatttac gtatgtatat atgtagatct ggacttttg gagttgttga cttgattgta     2640
tttgtgtgtg tatatgtgtg ttctgatctt gatatgttat gtatgtgcag cccggatctc    2700
cgggtaggtc agtcccttat gttacgtcct gtagaaaccc caacccgtga atcaaaaaa    2760 ctcgacggcc tgtgggcatt cagtctggat cgcgaaaact gtggaattgg tcagcgttgg    2820
tgggaaagcg cgttacaaga aagccgggca attgctgtgc caggcagttt taacgatcag    2880
ttcgccgatg cagatattcg taattatgcg ggcaacgtct ggtatcagcg cgaagtcttt    2940
ataccgaaag gttgggcagg ccagcgtatc gtgctgcgtt tcgatgcggt cactcattac    3000
ggcaaagtgt gggtcaataa tcaggaagtg atggagcatc agggcggcta tacgccattt    3060
gaagccgatg tcacgccgta tgttattgcc gggaaaagtg tacgtaagtt tctgcttcta    3120
cctttgatat atatataata attatcatta attagtagta atataatatt tcaaatattt    3180
ttttcaaaat aaaagaatgt agtatatagc aattgctttt ctgtagttta aagtgtgta    3240 tattttaatt tataacttt ctaatatatg accaaaattt gttgatgtgc aggtatcacc     3300
gtttgtgtga acaacgaact gaactggcag actatcccgc cgggaatggt gattaccgac    3360
gaaaacggca agaaaagca gtcttacttc catgatttct ttaactatgc cggaatccat    3420
cgcagcgtaa tgctctacac cacgccgaac acctgggtgg acgatatcac cgtggtgacg    3480
catgtcgcgc aagactgtaa ccacgcgtct gttgactggc aggtggtggc caatggtgat    3540
gtcagcgttg aactgcgtga tgcggatcaa caggtggttg caactggaca aggcactagc    3600
gggactttgc aagtggtgaa tccgcacctc tggcaaccgg gtgaaggtta tctctatgaa    3660
ctgtgcgtca cagccaaaag ccagacagag tgtgatatct acccgcttcg cgtcggcatc    3720
cggtcagtgg cagtgaaggg cgaacagttc ctgattaacc acaaaccgtt ctactttact    3780
ggctttggtc gtcatgaaga tgcggacttg cgtggcaaag gattcgataa cgtgctgatg    3840
gtgcacgacc acgcattaat ggactggatt ggggccaact cctaccgtac ctcgcattac    3900
ccttacgctg aagagatgct cgactgggca gatgaacatg gcatcgtggt gattgatgaa    3960
```

-continued

```
actgctgctg tcggctttaa cctctcttta ggcattggtt tcgaagcggg caacaagccg    4020
aaagaactgt acagcgaaga ggcagtcaac ggggaaactc agcaagcgca cttacaggcg    4080
attaaagagc tgatagcgcg tgacaaaaac cacccaagcg tggtgatgtg gagtattgcc    4140
aacgaaccgg atacccgtcc gcaaggtgca cgggaatatt tcgcgccact ggcggaagca    4200
acgcgtaaac tcgacccgac gcgtccgatc acctgcgtca atgtaatgtt ctgcgacgct    4260
cacaccgata ccatcagcga tctctttgat gtgctgtgcc tgaaccgtta ttacggatgg    4320
tatgtccaaa gcggcgattt ggaaacggca gagaaggtac tggaaaaaga acttctggcc    4380
tggcaggaga aactgcatca gccgattatc atcaccgaat acggcgtgga tacgttagcc    4440
gggctgcact caatgtacac cgacatgtgg agtgaagagt atcagtgtgc atggctggat    4500
atgtatcacc gcgtctttga tcgcgtcagc gccgtcgtcg gtgaacaggt atggaatttc    4560
gccgattttg cgacctcgca aggcatattg cgcgttggcg gtaacaagaa agggatcttc    4620
actcgcgacc gcaaaccgaa gtcggcggct tttctgctgc aaaaacgctg gactggcatg    4680
aacttcggtg aaaaaccgca gcagggaggc aaacaatgaa tcaacaactc tcctggcgca    4740
ccatcgtcgg ctacagcctc gggaattgct accgagctcg aatttccccg atcgttcaaa    4800
catttggcaa taaagtttct taagattgaa tcctgttgcc ggtcttgcga tgattatcat    4860
ataatttctg ttgaattacg ttaagcatgt aataattaac atgtaatgca tgacgttatt    4920
tatgagatgg gtttttatga ttagagtccc gcaattatac atttaatacg cgatagaaaa    4980
caaaatatag cgcgcaaact aggataaatt atcgcgcgcg gtgtcatcta tgttactaga    5040
tcgggaattg gcgatcgcag cttggcgtaa tcatggtcat agctgtttcc tactagatct    5100
gattgtcgtt tcccgccttc agtttaaact atcagtgttt gacaggatat attggcgggt    5160
aaacctaaga gaaagagcg tttattagaa taatcggata tttaaagggc cgtgaaaagg    5220
tttatccgtt cgtccatttg tatgtc                                        5246
```

<210> SEQ ID NO 13
<211> LENGTH: 6887
<212> TYPE: DNA
<213> ORGANISM: Artificial sequence
<220> FEATURE:
<223> OTHER INFORMATION: T-DNA of RET63, a RLM407-type Selda-GUS Binary
      Vector: LB> <p-AtAct2i::c-dsdA/na::t-NOS p-PcUBI::c-gusINT::t-NOS>
      RB>.
<220> FEATURE:
<221> NAME/KEY: misc_feature
<222> LOCATION: (1)..(215)
<223> OTHER INFORMATION: Left T-DNA border (full) similar to #TIP37TD1
      Ti plasmid (from A.tumefaciens, nopaline strain T37).
<220> FEATURE:
<221> NAME/KEY: misc_feature
<222> LOCATION: (47)..(71)
<223> OTHER INFORMATION: Left T-DNA Border repeat region; similar to
      #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
      poly-A terminator.
<220> FEATURE:
<221> NAME/KEY: misc_feature
<222> LOCATION: (561)..(1889)
<223> OTHER INFORMATION: Complement of CDS for E.coli D-serine
      dehydratase; GenBank Acc.-No.: J01603.
<220> FEATURE:
<221> NAME/KEY: promoter
<222> LOCATION: (1919)..(3326)
<223> OTHER INFORMATION: Complement of promoter from Arabidopsis
      thaliana Actin-2 promoter with internal intron; 98% homology to
      #ATU41998 Arabidopsis thaliana actin 2 (ACT2) gene.
<220> FEATURE:

```
<221> NAME/KEY: promoter
<222> LOCATION: (3339)..(4334)
<223> OTHER INFORMATION: Parsley UBI4-2 promoter with internal intron;
      99% homology to #PCCUBI42 P.crispum gene Pcubi4-2 for
      polyubiquitin; from QC28-6/JB010.
<220> FEATURE:
<221> NAME/KEY: misc_feature
<222> LOCATION: (4360)..(6360)
<223> OTHER INFORMATION: gusINT CDS comprise of the E. coli gusA CDS
      containing and internal PIV2 intron.
<220> FEATURE:
<221> NAME/KEY: terminator
<222> LOCATION: (6431)..(6683)
<223> OTHER INFORMATION: Agrobacterium Nopaline Synthase poly-A
      terminator.
<220> FEATURE:
<221> NAME/KEY: misc_feature
<222> LOCATION: (6742)..(6887)
<223> OTHER INFORMATION: Right T-DNA Border; similar to genbank#TIP37TD2
      Ti plasmid (from A. tumefaciens, nopaline strain T37) T-DNA 3'
      (right) border.
<220> FEATURE:
<221> NAME/KEY: misc_feature
<222> LOCATION: (6824)..(6847)
<223> OTHER INFORMATION: Right T-DNA Border repeat region; similar to
      #TIP37TD2; from pCambia2301.

<400> SEQUENCE: 13
gtgattttgt gccgagctgc cggtcgggga gctgttggct ggctggtggc aggatatatt    60
gtggtgtaaa caaattgacg cttagacaac ttaataacac attgcggacg tctttaatgt   120
actgaattaa catccgtttg atacttgtct aaaattggct gatttcgagt gcatctatgc   180
ataaaaacaa tctaatgaca attattacca agcaggatcc tctagaattc ccgatctagt   240
aacatagatg acaccgcgcg cgataattta tcctagtttg cgcgctatat tttgttttct   300
atcgcgtatt aaatgtataa ttgcgggact ctaatcataa aaacccatct cataaataac   360
gtcatgcatt acatgttaat tattacatgc ttaacgtaat tcaacagaaa ttatatgata   420
atcatcgcaa gaccggcaac aggattcaat cttaagaaac tttattgcca aatgtttgaa   480
cgatcgggga aattcgagct cgccggcgtc gacgatatcc tgcaggagct cggtacgatc   540
catgctgcgt tgaaacgtta ttaacggcct tttgccagat attgattcat ctcttcttcc   600
ggcaccattc cacctcccgt cgcccacacc agatgagtgg tattacgcag ttgttctgcg   660
ctgaaaccgt gcatctgttg gtaacttact gatgcacaca cgcgctgagg tccgccata    720 cccgccagtg ccgaaggttc aagacgaata ccttcttcct gcgccagcca gccaagcatg   780
tcatacatgg tttgatcgct aagggtatag aagccatcca gcagacgctc cattgcccgc   840
ccgacaaagc ctgatgcgcg accaactgca aggccatccg ctgcggtaag gttgtcgata   900
ccaatatcct gaacagaaat ctgatcgtgt aatcctgtat ggacgcctaa caacatacaa   960 gggggagtgcg ttggttcggc aaaaaagcag tgaacatgat cgccaaacgc cagtttaagc  1020
ccgaatgcga cgccaccagg accaccgcca acaccacacg gcagatagac aaacagaggg  1080
ttatcagcat cgacgatacg gccttgctgg gcaaattgcg ctttaagacg ctggccagcg  1140
acggaatacc caaggaacaa cgtgcgggaa ttttcgtcat caataaagaa acagttcggg  1200
tcagactgcg ctgctttacg tccttcctcg acggcaacac cataatcttg ctcatattcc  1260
acgaccgtaa cgccatggct gcgcagtttc gcttttttcc atgcccgggc atcagcagac  1320
atatgaactg tcaccttaaa gccaatgcgg gcgctcataa tgccgattga taaccccaga  1380
tttccggttg agcccacagc aatgctgtat tggctaaaga actgtttaaa ctccggagaa  1440
agcagtttgc tgtagtcatc atcaagcgtc agcaaccccg cttccagagc cagttttttct 1500 gcgtgtgcca ggacttcata aatcccgccg cgtgcttta tggagccgga aatgggcaaa  1560
```

```
tggctatctt ttttcagtaa cagttgcccg ctgatcggtt gctgatattc tttttccagc    1620 cgttttgca tagctggaat ggcaaccagt tctgattcaa taatcccccc agtggcagca    1680
gtttcaggaa atgcttttgc cagatagggt gcaaaacggg ataagcgcgc atgggcgtcc    1740
tgaacatcct gttcggtcag gccaacataa ggtaaacctt cagccaatga ggtcgtgcca    1800
ggattaaacc aggtggtttc tttaagagca accagatcct ttaccaacgg atactgggcg    1860
atgagcgagt tcattttagc gttttccata gtacgtctct ttggatccgg cgcgcctttt    1920
ttttatgagc tgcaaacaca caaaaagagt tcaatacagt caaataaacc ctgattgaat    1980
cagaaatagc tttctgttca acgtacgaca ctacaaatcc taaagtttcg aagaatctat    2040
acacaaactt catctaacct taaacagtgt tcagattcaa tctaacattg acagtgttca    2100
gattcaatct aacttcaaca gttcagattt caattcacat atacaaatca tttcccaggt    2160
aacatgaaca tggatctctc catcaaggtc aagccaaatt ctggtagcta taatcgagct    2220
aactgatcgg tcaacttaga tcgattctag taaaaccaaa agatttagtg gaggttcaca    2280
gatccaaatt aaacgaattc cagatctcaa ggaaattgag aaaacaagat cgagatccag    2340
caaataaagt agatccagaa agttcctatt accttggaaa gaaagagcgg aagaagatga    2400
gattgaggaa gattcaaaac ggagaatgaa tctcctggat tatctcttac tttctctctt    2460
agtcttcttc cttgttcttc tctgtcaagt cgccggagag tcaaaacggc tgatgaaagt    2520
gaggaggaca acgagacaat tcaaagcgga gaggaaaata tatgaattta tataggcggg    2580
tttatctctt acaactttat tttcggcctt tcaaaaaaat aattaaaatc gacagacacg    2640
aatcatttcg accacaggta agataacgt gacctggctg tcagacagcc ttttccctcg    2700
tgttaactaa tttttaaact aattaatcat ctcagccctt ggattagttc ttttgctttg    2760
atggcttcat gactgtgacc tgctcgatcc gcgtgttaca tgacagctcc gttttttag    2820 tggttaactt aaaccgagtc aatccaggca acgttagtcg tcgtcgtggt tggcttgttc    2880
aattagattt catacaattc aacgtaattt aattcgtttt ctattagaat tgtatcataa    2940
ttaattcaga ccgtgaaaga aagtgtcttt catgatgtgt ttatggatat ttatacaata    3000
agatacaatg tttcatcata ttcactattc acgattagta tgtacattaa ataatggcta    3060
ctactacatc cgaactcgtc aaaacgattc tgaatcaatt atacatatgc tgactcttgc    3120
atacataaaa aatagttgtt taaattttgt ctaactaatg tttggtataa gtataatgtt    3180
gagttgagat accaattaca tcgagtctag ccattttgtc gtgccatatt cgtcaaaact    3240
ttcttacata atgataacct agatctagat gagatatgta tcaatgtatt tgagatcata    3300
attaagttcg ttctaaattt tgtcgaaacc aacgcaagct tgactagaga attcgaatcc    3360
aaaaattacg gatatgaata taggcatatc cgtatccgaa ttatccgttt gacagctagc    3420
aacgattgta caattgcttc tttaaaaaag gaagaaagaa agaaagaaaa gaatcaacat    3480
cagcgttaac aaacggcccc gttacggccc aaacggtcat atagagtaac ggcgttaagc    3540
gttgaaagac tcctatcgaa atacgtaacc gcaacgtgt catagtcaga tcccctcttc    3600
cttcaccgcc tcaaacacaa aaataatctt ctacagccta tatatacaac ccccccttct    3660
atctctcctt tctcacaatt catcatcttt ctttctctac ccccaatttt aagaaatcct    3720
ctcttctcct cttcattttc aaggtaaatc tctctctctc tctctctctc tgttattcct    3780
tgttttaatt aggtatgtat tattgctagt ttgttaatct gcttatctta tgtatgcctt    3840
atgtgaatat ctttatcttg ttcatctcat ccgtttagaa gctataaatt tgttgatttg    3900
actgtgtatc tacacgtggt tatgtttata tctaatcaga tatgaatttc ttcatattgt    3960
```

```
tgcgtttgtg tgtaccaatc cgaaatcgtt gattttttc atttaatcgt gtagctaatt    4020
gtacgtatac atatggatct acgtatcaat tgttcatctg tttgtgtttg tatgtataca    4080
gatctgaaaa catcacttct ctcatctgat tgtgttgtta catacataga tatagatctg    4140
ttatatcatt ttttttatta attgtgtata tatatatgtg catagatctg gattacatga    4200
ttgtgattat ttacatgatt ttgttattta cgtatgtata tatgtagatc tggacttttt    4260
ggagttgttg acttgattgt atttgtgtgt gtatatgtgt gttctgatct tgatatgtta    4320
tgtatgtgca gcccggatct ccgggtaggt cagtccctta tgttacgtcc tgtagaaacc    4380
ccaacccgtg aaatcaaaaa actcgacggc ctgtgggcat tcagtctgga tcgcgaaaac    4440
tgtggaattg gtcagcgttg gtgggaaagc gcgttacaag aaagccgggc aattgctgtg    4500
ccaggcagtt ttaacgatca gttcgccgat gcagatattc gtaattatgc gggcaacgtc    4560
tggtatcagc gcgaagtctt tataccgaaa ggttgggcag ccagcgtat cgtgctgcgt    4620
ttcgatgcgg tcactcatta cggcaaagtg tgggtcaata tcaggaagt gatggagcat    4680
cagggcggct atacgccatt tgaagccgat gtcacgccgt atgttattgc cgggaaaagt    4740
gtacgtaagt ttctgcttct acctttgata tatatataat aattatcatt aattagtagt    4800
aatataatat ttcaaatatt tttttcaaaa taaagaatg tagtatatag caattgcttt    4860
tctgtagttt ataagtgtgt atattttaat ttataacttt tctaatatat gaccaaaatt    4920
tgttgatgtg caggtatcac cgtttgtgtg aacaacgaac tgaactggca gactatcccg    4980
ccgggaatgt tgattaccga cgaaaacggc aagaaaaagc agtcttactt ccatgatttc    5040
tttaactatg ccggaatcca tcgcagcgta atgctctaca ccacgccgaa cacctgggtg    5100
gacgatatca ccgtggtgac gcatgtcgcg caagactgta accacgcgtc tgttgactgg    5160
caggtggtgg ccaatggtga tgtcagcgtt gaactgcgtg atgcggatca acaggtggtt    5220
gcaactggac aaggcactag cgggacttt caagtggtga atccgcacct ctggcaaccg    5280
ggtgaaggtt atctctatga actgtgcgtc acagccaaaa gccagacaga gtgtgatatc    5340
tacccgcttc gcgtcggcat ccggtcagtg gcagtgaagg cgaacagtt cctgattaac    5400
cacaaaccgt tctactttac tggctttggt cgtcatgaag atgcggactt gcgtggcaaa    5460
ggattcgata acgtgctgat ggtgcacgac cacgcattaa tggactggat tggggccaac    5520
tcctaccgta cctcgcatta cccttacgct gaagagatgc tcgactgggc agatgaacat    5580
ggcatcgtgg tgattgatga aactgctgct gtcggcttta acctctcttt aggcattggt    5640
ttcgaagcgg gcaacaagcc gaaagaactg tacagcgaag aggcagtcaa cggggaaact    5700
cagcaagcgc acttcaggc gattaaagag ctgatagcgc gtgacaaaaa ccacccaagc    5760
gtggtgatgt ggagtattgc caacgaaccg gatacccgtc cgcaaggtgc acgggaatat    5820
ttcgcgccac tggcggaagc aacgcgtaaa ctcgacccga cgcgtccgat cacctgcgtc    5880
aatgtaatgt tctgcgacgc tcacaccgat accatcagcg atctctttga tgtgctgtgc    5940
ctgaaccgtt attacggatg gtatgtccaa agcggcgatt tggaaacggc agagaaggta    6000
ctggaaaaag aacttctggc ctggcaggag aaactgcatc agccgattat catcaccgaa    6060
tacggcgtgg atacgttagc cgggctgcac tcaatgtaca ccgacatgtg gagtgaagag    6120
tatcagtgtg catggctgga tatgtatcac cgcgtctttg atcgcgtcag cgccgtcgtc    6180
ggtgaacagg tatggaattt cgccgatttt gcgacctcgc aaggcatatt gcgcgttggc    6240
ggtaacaaga aagggatctt cactcgcgac cgcaaaccga gtcggcggc ttttctgctg    6300
caaaaacgct ggactggcat gaacttcggt gaaaaaccgc agcagggagg caaacaatga    6360
```

```
atcaacaact ctcctggcgc accatcgtcg gctacagcct cgggaattgc taccgagctc    6420
gaatttcccc gatcgttcaa acatttggca ataaagtttc ttaagattga atcctgttgc    6480
cggtcttgcg atgattatca tataatttct gttgaattac gttaagcatg taataattaa    6540
catgtaatgc atgacgttat ttatgagatg ggtttttatg attagagtcc cgcaattata    6600
catttaatac gcgatagaaa acaaaatata gcgcgcaaac taggataaat tatcgcgcgc    6660
ggtgtcatct atgttactag atcgggaatt ggcgatcgca gcttggcgta atcatggtca    6720
tagctgtttc ctactagatc tgattgtcgt ttcccgcctt cagtttaaac tatcagtgtt    6780
tgacaggata tattggcggg taaacctaag agaaaagagc gtttattaga ataatcggat    6840
atttaaaagg gcgtgaaaag gtttatccgt tcgtccattt gtatgtc                  6887
```

```
<210> SEQ ID NO 14
<211> LENGTH: 6600
<212> TYPE: DNA
<213> ORGANISM: Artificial sequence
<220> FEATURE:
<223> OTHER INFORMATION: T-DNA of RET19, a RLM407-type Selda-GUS Binary
      Vector: LB> <p-AtAct2i::c-dao1/pa::t-NOS p-PcUBI::c-gusINT::t-NOS>
      RB>.
<220> FEATURE:
<221> NAME/KEY: misc_feature
<222> LOCATION: (1)..(215)
<223> OTHER INFORMATION: Left T-DNA border (full) similar to #TIP37TD1
      Ti plasmid (from A.tumefaciens, nopaline strain T37).
<220> FEATURE:
<221> NAME/KEY: misc_feature
<222> LOCATION: (47)..(71)
<223> OTHER INFORMATION: Left T-DNA Border repeat region; similar to
      #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
      poly-A terminator.
<220> FEATURE:
<221> NAME/KEY: misc_feature
<222> LOCATION: (536)..(1642)
<223> OTHER INFORMATION: Complement of CDS for Rhodosporidium toruloides
      D-amino acid oxidase; GenBank U60066 & US patent 5948660; from
      QC142-1/LM202.
<220> FEATURE:
<221> NAME/KEY: promoter
<222> LOCATION: (1668)..(3075)
<223> OTHER INFORMATION: Complement of promoter from Arabidopsis
      thaliana Actin-2 promoter with internal intron; 98% homology to
      #ATU41998 Arabidopsis thaliana actin 2 (ACT2) gene.
<220> FEATURE:
<221> NAME/KEY: promoter
<222> LOCATION: (3088)..(4083)
<223> OTHER INFORMATION: Parsley UBI4-2 promoter with internal intron;
      99% homology to #PCCUBI42 P.crispum gene Pcubi4-2 for
      polyubiquitin; from QC28-6/JB010.
<220> FEATURE:
<221> NAME/KEY: misc_feature
<222> LOCATION: (4109)..(6109)
<223> OTHER INFORMATION: gusINT CDS comprise of the E. coli gusA CDS
      containing and internal PIV2 intron.
<220> FEATURE:
<221> NAME/KEY: terminator
<222> LOCATION: (6180)..(6432)
<223> OTHER INFORMATION: Agrobacterium Nopaline Synthase poly-A
      terminator.
<220> FEATURE:
<221> NAME/KEY: misc_feature
<222> LOCATION: (6491)..(6635)
<223> OTHER INFORMATION: Right T-DNA Border; similar to genbank#TIP37TD2
      Ti plasmid (from A. tumefaciens, nopaline strain T37) T-DNA 3'
      (right) border.
<220> FEATURE:
<221> NAME/KEY: misc_feature
<222> LOCATION: (6573)..(6596)
```

<223> OTHER INFORMATION: Right T-DNA Border repeat region; similar to #TIP37TD2; from pCambia2301.

<400> SEQUENCE: 14

```
gtgattttgt gccgagctgc cggtcgggga gctgttggct ggctggtggc aggatatatt    60
gtggtgtaaa caaattgacg cttagacaac ttaataacac attgcggacg tctttaatgt   120
actgaattaa catccgtttg atacttgtct aaaattggct gatttcgagt gcatctatgc   180
ataaaaacaa tctaatgaca attattacca agcaggatcc tctagaattc ccgatctagt   240
aacatagatg acaccgcgcg cgataattta tcctagtttg cgcgctatat tttgttttct   300
atcgcgtatt aaatgtataa ttgcgggact ctaatcataa aaacccatct cataaataac   360
gtcatgcatt acatgttaat tattacatgc ttaacgtaat tcaacagaaa ttatatgata   420
atcatcgcaa gaccggcaac aggattcaat cttaagaaac tttattgcca aatgtttgaa   480
cgatcgggga aattcgagct cgccggcgtc gacgatatcc tgcaggaatc ccgccctaca   540
acttcgactc ccgcgccgcg ccgtggtacc gctggaacgc ctcgtcgacg agctgcgcga   600
catcctccgc cgcgccccaa ctctgctggt atcccgcact cgagaagcca tacgcatgca   660
caagcgtgac ctccttctcc ttcgccgctc gtgcgctgcc cctgccgagc gagaggggcg   720
actttgtccg gtcgagaggc aggacgatcc gttctgcctc aacgcggggt ccgcctcgtc   780
gtgcaggtcg caagccgacg ttgtggcgga ggacctcgat gccttcgatc gttccgtcgc   840
tcgagatggt cgggtcgagg cgcaagcagt gcttgaggat ccgctggacc gtctctgggt   900
tgacagacaa gtcccagtct cccacgccgt acgtcccgcc gcagatgact cgccacctg   960
gtcggggaat gatgtaggcg ggagaagcgg ggtcggacga gtccatcgtg catcgcttgc  1020
atggggactt gacgaggacg gtttgccccgc ggattggctc ggcggcttgg tcgtcgatgc  1080
ccgcaatcga cttggcgcca gtcccgtag cgttgaccac caaatccgca ccgtcgaacg  1140
cctgctcaag cgacgtaacg gtccgtctct caaacgtcgc gccgagcttc tgcagctctc  1200
ttgcaaggta ctggcagtac tttggtgcgt ggacggagag ggtgtcgtag gttacgccga  1260
tagcgccagg tggacattcg gaagatggga ggggcggta atttggcgtg atgtccttgt  1320
accagtgccc gagcaagccg tcttcgttct gcgcgaaccg cctcgtcccc ttgagccaca  1380
tggcatggcc cgtcgggacc aactcgaccc acttcttgaa agtcgattct tcccattttg  1440
cttgtcgagg accgtctgta agcgtcatga aaggcgtcca attcgcgcca gcccatggtg  1500
aagcgaaagt ctggctcgag acgtcctccg gcaagtcgcg cgcagaata tgcacgctgt  1560
agcccttccg agcgaggatg agggcgctgc tcagaccgat aacgcctgat ccgaggacaa  1620
cgacgcgctt ctgcgagtgc atggtggccc gggatccggc gcgcctttt tttatgagct  1680
gcaaacacac aaaaagagtt caatacagtc aaataaaccc tgattgaatc agaaatagct  1740
ttctgttcaa cgtacgacac tacaaatcct aaagtttcga agaatctata cacaaacttc  1800
atctaacctt aaacagtgtt cagattcaat ctaacattga cagtgttcag attcaatcta  1860
acttcaacag ttcagatttc aattcacata tacaaatcat ttcccaggta acatgaacat  1920
ggatctctcc atcaaggtca agccaaattc tggtagctat aatcgagcta actgatcggt  1980
caacttagat cgattctagt aaaaccaaaa gatttagtgg aggttcacag atccaaatta  2040
aacgaattcc agatctcaag gaaattgaga aaacaagatc gagatccagc aaataaagta  2100
gatccagaaa gttcctatta ccttggaaag aaagagcgga agaagatgag attgaggaag  2160
attcaaaacg gagaatgaat ctcctggatt atctcttact ttctctctta gtcttcttcc  2220
ttgttcttct ctgtcaagtc gccggagatt caaaacggct gatgaaagtg aggaggacaa  2280
```

```
cgagacaatt caaagcggag aggaaaatat atgaatttat ataggcgggt ttatctctta    2340
caactttatt ttcggccttt caaaaaaata attaaaatcg acagacacga atcatttcga    2400
ccacaggtaa agataacgtg acctggctgt cagacagcct tttccctcgt gttaactaat    2460
ttttaaacta attaatcatc tcagcccttg gattagttct tttgctttga tggcttcatg    2520
actgtgacct gctcgatccg cgtgttacat gacagctccg ttttttttagt ggttaactta    2580 aaccgagtca atccaggcaa cgttagtcgt cgtcgtggtt ggcttgttca attagatttc    2640
atacaattca acgtaattta attcgttttc tattagaatt gtatcataat taattcagac    2700
cgtgaaagaa agtgtctttc atgatgtgtt tatggatatt tatacaataa gatacaatgt    2760
ttcatcatat tcactattca cgattagtat gtacattaaa taatggctac tactacatcc    2820
gaactcgtca aaacgattct gaatcaatta tacatatgct gactcttgca tacataaaaa    2880
atagttgttt aaattttgtc taactaatgt ttggtataag tataatgttg agttgagata    2940
ccaattacat cgagtctagc cattttgtcg tgccatattc gtcaaaactt tcttacataa    3000
tgataaccta gatctagatg agatatgtat caatgtattt gagatcataa ttaagttcgt    3060
tctaaatttt gtcgaaacca acgcaagctt gactagagaa ttcgaatcca aaaattacgg    3120
atatgaatat aggcatatcc gtatccgaat tatccgtttg acagctagca acgattgtac    3180
aattgcttct ttaaaaaagg aagaaagaaa gaaagaaaag aatcaacatc agcgttaaca    3240
aacggccccg ttacggccca aacggtcata tagagtaacg gcgttaagcg ttgaaagact    3300
cctatcgaaa tacgtaaccg caaacgtgtc atagtcagat cccctcttcc ttcaccgcct    3360
caaacacaaa aataatcttc tacagcctat atatacaacc ccccttcta tctctccttt    3420 ctcacaattc atcatctttc tttctctacc cccaatttta agaaatcctc tcttctcctc    3480
ttcattttca aggtaaatct ctctctctct ctctctctct gttattcctt gttttaatta    3540
ggtatgtatt attgctagtt tgttaatctg cttatcttat gtatgcctta tgtgaatatc    3600
tttatcttgt tcatctcatc cgtttagaag ctataaattt gttgatttga ctgtgtatct    3660
acacgtggtt atgtttatat ctaatcagat atgaatttct tcatattgtt gcgtttgtgt    3720
gtaccaatcc gaaatcgttg atttttttca tttaatcgtg tagctaattg tacgtataca    3780
tatggatcta cgtatcaatt gttcatctgt ttgtgtttgt atgtatacag atctgaaaac    3840
atcacttctc tcatctgatt gtgttgttac atacatagat atagatctgt tatatcattt    3900
tttttattaa ttgtgtatat atatatgtgc atagatctgg attacatgat tgtgattatt    3960
tacatgattt tgttatttac gtatgtatat atgtagatct ggacttttttg gagttgttga    4020 cttgattgta tttgtgtgtg tatatgtgtg ttctgatctt gatatgttat gtatgtgcag    4080
cccggatctc cgggtaggtc agtcccttat gttacgtcct gtagaaaccc caacccgtga    4140
aatcaaaaaa ctcgacggcc tgtgggcatt cagtctggat cgcgaaaact gtggaattgg    4200
tcagcgttgg tgggaaagcg cgttacaaga agccgggca attgctgtgc caggcagttt    4260
taacgatcag ttcgccgatg cagatattcg taattatgcg ggcaacgtct ggtatcagcg    4320
cgaagtcttt ataccgaaag gttgggcagg ccagcgtatc gtgctgcgtt tcgatgcggt    4380
cactcattac ggcaaagtgt gggtcaataa tcaggaagtg atggagcatc agggcggcta    4440
tacgccattt gaagccgatg tcacgccgta tgttattgcc gggaaaagtg tacgtaagtt    4500
tctgcttcta ccttttgatat atatataata attatcatta attagtagta atataatatt    4560
tcaaatattt ttttcaaaat aaaagaatgt agtatatagc aattgctttt ctgtagttta    4620
taagtgtgta tattttaatt tataacttttt ctaatatatg accaaaattt gttgatgtgc    4680
```

```
aggtatcacc gtttgtgtga acaacgaact gaactggcag actatcccgc cgggaatggt    4740
gattaccgac gaaaacggca agaaaaagca gtcttacttc catgatttct ttaactatgc    4800
cggaatccat cgcagcgtaa tgctctacac cacgccgaac acctgggtgg acgatatcac    4860
cgtggtgacg catgtcgcgc aagactgtaa ccacgcgtct gttgactggc aggtggtggc    4920
caatggtgat gtcagcgttg aactgcgtga tgcggatcaa caggtggttg caactggaca    4980
aggcactagc gggactttgc aagtggtgaa tccgcacctc tggcaaccgg gtgaaggtta    5040
tctctatgaa ctgtgcgtca cagccaaaag ccagacagag tgtgatatct acccgcttcg    5100
cgtcggcatc cggtcagtgg cagtgaaggg cgaacagttc ctgattaacc acaaaccgtt    5160
ctactttact ggctttggtc gtcatgaaga tgcggacttg cgtggcaaag gattcgataa    5220
cgtgctgatg gtgcacgacc acgcattaat ggactggatt ggggccaact cctaccgtac    5280
ctcgcattac ccttacgctg aagagatgct cgactgggca gatgaacatg gcatcgtggt    5340
gattgatgaa actgctgctg tcggctttaa cctctcttta ggcattggtt tcgaagcggg    5400
caacaagccg aaagaactgt acagcgaaga ggcagtcaac ggggaaactc agcaagcgca    5460
cttacaggcg attaaagagc tgatagcgcg tgacaaaaac cacccaagcg tggtgatgtg    5520
gagtattgcc aacgaaccgg ataccegtcc gcaaggtgca cgggaatatt tcgcgccact    5580
ggcggaagca acgcgtaaac tcgacccgac gcgtccgatc acctgcgtca atgtaatgtt    5640
ctgcgacgct cacaccgata ccatcagcga tctctttgat gtgctgtgcc tgaaccgtta    5700
ttacggatgg tatgtccaaa gcggcgattt ggaaacggca gagaaggtac tggaaaaaga    5760
acttctggcc tggcaggaga aactgcatca gccgattatc atcaccgaat acggcgtgga    5820
tacgttagcc gggctgcact caatgtacac cgacatgtgg agtgaagagt atcagtgtgc    5880
atggctggat atgtatcacc gcgtctttga tcgcgtcagc gccgtcgtcg gtgaacaggt    5940
atggaatttc gccgattttg cgacctcgca aggcatattg cgcgttggcg gtaacaagaa    6000
agggatcttc actcgcgacc gcaaaccgaa gtcggcggct tttctgctgc aaaaacgctg    6060
gactggcatg aacttcggtg aaaaaccgca gcagggaggc aaacaatgaa tcaacaactc    6120
tcctggcgca ccatcgtcgg ctacagcctc gggaattgct accgagctcg aatttccccg    6180
atcgttcaaa catttggcaa taaagtttct taagattgaa tcctgttgcc ggtcttgcga    6240
tgattatcat ataatttctg ttgaattacg ttaagcatgt aataattaac atgtaatgca    6300
tgacgttatt tatgagatgg gtttttatga ttagagtccc gcaattatac atttaatacg    6360
cgatagaaaa caaaatatag cgcgcaaact aggataaatt atcgcgcgcg gtgtcatcta    6420
tgttactaga tcgggaattg gcgatcgcag cttggcgtaa tcatggtcat agctgtttcc    6480
tactagatct gattgtcgtt tcccgccttc agtttaaact atcagtgttt gacaggatat    6540
attggcgggt aaacctaaga gaaagagcg tttattagaa taatcggata tttaaagggg    6600
```

<210> SEQ ID NO 15
<211> LENGTH: 6076
<212> TYPE: DNA
<213> ORGANISM: Artificial sequence
<220> FEATURE:
<223> OTHER INFORMATION: T-DNA of RET17, a RLM407-type Selda-GUS Binary
    Vector: LB> <p-NOS:c-dsdA/na::t-NOS p-PcUBI::c-gusINT::t-NOS> RB>.
<220> FEATURE:
<221> NAME/KEY: misc_feature
<222> LOCATION: (1)..(215)
<223> OTHER INFORMATION: Left T-DNA border (full) similar to #TIP37TD1
    Ti plasmid (from A.tumefaciens, nopaline strain T37).
<220> FEATURE:
<221> NAME/KEY: misc_feature

```
<222> LOCATION: (47)..(71)
<223> OTHER INFORMATION: Left T-DNA Border repeat region; similar to
      #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
      poly-A terminator.
<220> FEATURE:
<221> NAME/KEY: misc_feature
<222> LOCATION: (561)..(1889)
<223> OTHER INFORMATION: Complement of CDS for E.coli D-serine
      dehydratase; GenBank Acc.-No.: J01603.
<220> FEATURE:
<221> NAME/KEY: promoter
<222> LOCATION: (1922)..(2209)
<223> OTHER INFORMATION: Complement of promoter from the noplaine
      synthase gene (Depicker et al. 1982, J.Mol.Appl.Genet. 1:561-573)
      EMBL no: V00087.
<220> FEATURE:
<221> NAME/KEY: promoter
<222> LOCATION: (2528)..(3523)
<223> OTHER INFORMATION: Parsley UBI4-2 promoter with internal intron;
      99% homology to #PCCUBI42 P.crispum gene Pcubi4-2 for
      polyubiquitin; from QC28-6/JB010.
<220> FEATURE:
<221> NAME/KEY: misc_feature
<222> LOCATION: (3549)..(5549)
<223> OTHER INFORMATION: gusINT CDS comprise of the E. coli gusA CDS
      containing and internal PIV2 intron.
<220> FEATURE:
<221> NAME/KEY: terminator
<222> LOCATION: (5620)..(5872)
<223> OTHER INFORMATION: Agrobacterium Nopaline Synthase poly-A
      terminator.
<220> FEATURE:
<221> NAME/KEY: misc_feature
<222> LOCATION: (5931)..(6076)
<223> OTHER INFORMATION: Right T-DNA Border; similar to genbank#TIP37TD2
      Ti plasmid (from A. tumefaciens, nopaline strain T37) T-DNA 3'
      (right) border.
<220> FEATURE:
<221> NAME/KEY: misc_feature
<222> LOCATION: (5971)..(5994)
<223> OTHER INFORMATION: Right T-DNA Border repeat region; similar to
      #TIP37TD2; from pCambia2301.

<400> SEQUENCE: 15
gtgattttgt gccgagctgc cggtcgggga gctgttggct ggctggtggc aggatatatt      60
gtggtgtaaa caaattgacg cttagacaac ttaataacac attgcggacg tctttaatgt     120
actgaattaa catccgtttg atacttgtct aaaattggct gatttcgagt gcatctatgc     180
ataaaaacaa tctaatgaca attattacca agcaggatcc tctagaattc ccgatctagt     240
aacatagatg acaccgcgcg cgataattta tcctagtttg cgcgctatat tttgttttct     300
atcgcgtatt aaatgtataa ttgcgggact ctaatcataa aaacccatct cataaataac     360
gtcatgcatt acatgttaat tattacatgc ttaacgtaat tcaacagaaa ttatatgata     420
atcatcgcaa gaccggcaac aggattcaat cttaagaaac tttattgcca aatgtttgaa     480
cgatcgggga aattcgagct cgccggcgtc gacgatatcc tgcaggagct cggtacgatc     540
catgctgcgt tgaaacgtta ttaacggcct tttgccagat attgattcat ctcttcttcc     600
ggcaccattc cacctcccgt cgcccacacc agatgagtgg tattacgcag ttgttctgcg     660
ctgaaaccgt gcatctgttg gtaacttact gatgcacaca cgcgctgagg tccggccata     720
cccgccagtg ccgaaggttc aagacgaata ccttcttcct cgccagcca gccaagcatg      780 tcatacatgg tttgatcgct aagggtatag aagccatcca gcagacgctc cattgcccgc     840
ccgacaaagc ctgatgcgcg accaactgca aggccatccg ctgcgtaag gttgtcgata     900 ccaatatcct gaacagaaat ctgatcgtgt aatcctgtat ggacgcctaa caacatacaa     960
```

```
ggggagtgcg ttggttcggc aaaaaagcag tgaacatgat cgccaaacgc cagtttaagc    1020
ccgaatgcga cgccaccagg accaccgcca acaccacacg gcagatagac aaacagaggg    1080
ttatcagcat cgacgatacg gccttgctgg gcaaattgcg ctttaagacg ctggccagcg    1140
acggaatacc caaggaacaa cgtgcgggaa ttttcgtcat caataaagaa acagttcggg    1200
tcagactgcg ctgctttacg tccttcctcg acggcaacac cataatcttg ctcatattcc    1260
acgaccgtaa cgccatggct gcgcagtttc gcttttttcc atgcccgggc atcagcagac    1320
atatgaactg tcaccttaaa gccaatgcgg gcgctcataa tgccgattga taaccccaga    1380
tttccggttg agcccacagc aatgctgtat tggctaaaga actgtttaaa ctccggagaa    1440
agcagtttgc tgtagtcatc atcaagcgtc agcaaccccg cttccagagc cagttttcct    1500
gcgtgtgcca ggacttcata aatcccgccg cgtgctttta tggagccgga aatgggcaaa    1560
tggctatctt ttttcagtaa cagttgcccg ctgatcggtt gctgatattc ttttccagc    1620 cgttttgca tagctggaat ggcaaccagt tctgattcaa taatcccccc agtggcagca    1680
gtttcaggaa atgcttttgc cagatagggt gcaaacggg ataagcgcgc atgggcgtcc    1740
tgaacatcct gttcggtcag gccaacataa ggtaaacctt cagccaatga ggtcgtgcca    1800
ggattaaacc aggtggtttc tttaagagca accagatcct ttaccaacgg atactgggcg    1860
atgagcgagt tcattttagc gttttccata gtacgtctct ttggatccgg cgcgccagat    1920
ctggattgag agtgaatatg agactctaat tggataccga ggggaattta tggaacgtca    1980
gtggagcatt tttgacaaga aatatttgct agctgatagt gaccttaggc gacttttgaa    2040
cgcgcaataa tggtttctga cgtatgtgct tagctcatta aactccagaa acccgcggct    2100
gagtggctcc ttcaacgttg cggttctgtc agttccaaac gtaaacggc ttgtcccgcg    2160 tcatcggcgg gggtcataac gtgactccct taattctccg ctcatgatct tgatcccctg    2220
cgccatcaga tccttggcgg caagaaagcc atccagttta cttttgcaggg cttcccaacc    2280 ttaccagagg gcgccccagc tggcaattcc ggttcgcttg ctgtccataa aaccgcccag    2340
tctagctatc gccatgtaag cccactgcaa gctacctgct ttctctttgc gcttgcgttt    2400
tcccttgtcc agatagccca gtagctgaca ttcatccggg gtcagcaccg tttctgcgga    2460
ctggctttct acgtgttccg cttcctttag cagcccttgc gccctgagtg cttgcggcag    2520
cgtgaagctt gactagagaa ttcgaatcca aaaattacgg atatgaatat aggcatatcc    2580
gtatccgaat tatccgtttg acagctagca acgattgtac aattgcttct ttaaaaaagg    2640
aagaaagaaa gaaagaaaag aatcaacatc agcgttaaca aacggccccg ttacggccca    2700
aacggtcata tagagtaacg gcgttaagcg ttgaaagact cctatcgaaa tacgtaaccg    2760
caaacgtgtc atagtcagat cccctcttcc ttcaccgcct caaacacaaa aataatcttc    2820
tacagcctat atatcaaacc cccccttcta tctctccttt ctcacaattc atcatctttc    2880
tttctctacc cccaatttta agaaatcctc tcttctcctc ttcattttca aggtaaatct    2940
ctctctctct ctctctctct gttattcctt gttttaatta ggtatgtatt attgctagtt    3000
tgttaatctg cttatcttat gtatgcctta tgtgaatatc tttatcttgt tcatctcatc    3060
cgtttagaag ctataaattt gttgatttga ctgtgtatct acacgtggtt atgtttatat    3120
ctaatcagat atgaatttct tcatattgtt gcgtttgtgt gtaccaatcc gaaatcgttg    3180 attttttttca tttaatcgtg tagctaattg tacgtataca tatggatcta cgtatcaatt    3240
gttcatctgt ttgtgtttgt atgtatacag atctgaaaac atcacttctc tcatctgatt    3300
gtgttgttac atacatagat atagatctgt tatatcattt tttttattaa ttgtgtatat    3360
```

```
atatatgtgc atagatctgg attacatgat tgtgattatt tacatgattt tgttatttac   3420
gtatgtatat atgtagatct ggacttttg gagttgttga cttgattgta tttgtgtgtg    3480
tatatgtgtg ttctgatctt gatatgttat gtatgtgcag cccggatctc cgggtaggtc   3540
agtcccttat gttacgtcct gtagaaaccc caacccgtga aatcaaaaaa ctcgacggcc   3600
tgtgggcatt cagtctggat cgcgaaaact gtggaattgg tcagcgttgg tgggaaagcg   3660
cgttacaaga aagccgggca attgctgtgc caggcagttt taacgatcag ttcgccgatg   3720
cagatattcg taattatgcg ggcaacgtct ggtatcagcg cgaagtcttt ataccgaaag   3780
gttgggcagg ccagcgtatc gtgctgcgtt tcgatgcggt cactcattac ggcaaagtgt   3840
gggtcaataa tcaggaagtg atggagcatc agggcggcta tacgccattt gaagccgatg   3900
tcacgccgta tgttattgcc gggaaaagtg tacgtaagtt tctgcttcta cctttgatat   3960
atatataata attatcatta attagtagta ataatatatt tcaaatattt ttttcaaaat   4020 aaagaatgt agtatatagc aattgctttt ctgtagttta taagtgtgta tattttaatt    4080
tataactttt ctaatatatg accaaaattt gttgatgtgc aggtatcacc gtttgtgtga   4140
acaacgaact gaactggcag actatcccgc cgggaatggt gattaccgac gaaaacggca   4200
agaaaaagca gtcttacttc catgatttct ttaactatgc cggaatccat cgcagcgtaa   4260
tgctctacac cacgccgaac acctgggtgg acgatatcac cgtggtgacg catgtcgcgc   4320
aagactgtaa ccacgcgtct gttgactggc aggtggtggc caatggtgat gtcagcgttg   4380
aactgcgtga tgcggatcaa caggtggttg caactggaca aggcactagc gggactttgc   4440
aagtggtgaa tccgcacctc tggcaaccgg gtgaaggtta tctctatgaa ctgtgcgtca   4500
cagccaaaag ccagacagag tgtgatatct acccgcttcg cgtcggcatc cggtcagtgg   4560
cagtgaaggg cgaacagttc ctgattaacc acaaaccgtt ctactttact ggctttggtc   4620
gtcatgaaga tgcggacttg cgtggcaaag gattcgataa cgtgctgatg gtgcacgacc   4680
acgcattaat ggactggatt ggggccaact cctaccgtac ctcgcattac ccttacgctg   4740
aagagatgct cgactgggca gatgaacatg gcatcgtggt gattgatgaa actgctgctg   4800
tcggctttaa cctctctta ggcattggtt tcgaagcggg caacaagccg aaagaactgt    4860
acagcgaaga ggcagtcaac ggggaaactc agcaagcgca cttacaggcg attaaagagc   4920
tgatagcgcg tgacaaaaac cacccaagcg tggtgatgtg gagtattgcc aacgaaccgg   4980
atacccgtcc gcaaggtgca cgggaatatt tcgcgccact ggcggaagca acgcgtaaac   5040
tcgacccgac gcgtccgatc acctgcgtca atgtaatgtt ctgcgacgct cacaccgata   5100
ccatcagcga tctctttgat gtgctgtgcc tgaaccgtta ttacgatggg tatgtccaaa   5160
gcggcgattt ggaaacggca gagaaggtac tggaaaaaga acttctggcc tggcaggaga   5220
aactgcatca gccgattatc atcaccgaat acggcgtgga tacgttagcc gggctgcact   5280
caatgtacac cgacatgtgg agtgaagagt atcagtgtgc atggctggat atgtatcacc   5340
gcgtctttga tcgcgtcagc gccgtcgtcg gtgaacaggt atggaatttc gccgattttg   5400
cgacctcgca aggcatattg cgcgttggcg gtaacaagaa agggatcttc actcgcgacc   5460
gcaaaccgaa gtcggcggct tttctgctgc aaaaacgctg gactggcatg aacttcggtg   5520
aaaaaccgca gcagggaggc aaacaatgaa tcaacaactc tcctggcgca ccatcgtcgg   5580
ctacagcctc gggaattgct accgagctcg aatttccccg atcgttcaaa catttggcaa   5640
taaagtttct taagattgaa tcctgttgcc ggtcttgcga tgattatcat ataatttctg   5700
ttgaattacg ttaagcatgt aataattaac atgtaatgca tgacgttatt tatgagatgg   5760
```

```
gtttttatga ttagagtccc gcaattatac atttaatacg cgatagaaaa caaaatatag      5820
cgcgcaaact aggataaatt atcgcgcgcg gtgtcatcta tgttactaga tcgggaattg      5880
gcgatcgcag cttggcgtaa tcatggtcat agctgtttcc tactagatct gattgtcgtt      5940
tcccgccttc agtttaaact atcagtgttt gacaggatat attggcgggt aaacctaaga      6000
gaaaagagcg tttattagaa taatcggata tttaaaaggg cgtgaaaagg tttatccgtt      6060
cgtccatttg tatgtc                                                    6076

<210> SEQ ID NO 16
<211> LENGTH: 5819
<212> TYPE: DNA
<213> ORGANISM: Artificial sequence
<220> FEATURE:
<223> OTHER INFORMATION: T-DNA of RET15, a RLM407-type Selda-GUS Binary
      Vector: LB> <p-NOS:c-dao1/ko::t-NOS p-PcUBI::c-gusINT::t-NOS> RB>.
<220> FEATURE:
<221> NAME/KEY: misc_feature
<222> LOCATION: (1)..(215)
<223> OTHER INFORMATION: Left T-DNA border (full) similar to #TIP37TD1
      Ti plasmid (from A.tumefaciens, nopaline strain T37).
<220> FEATURE:
<221> NAME/KEY: misc_feature
<222> LOCATION: (47)..(71)
<223> OTHER INFORMATION: Left T-DNA Border repeat region; similar to
      #AF234316 pCambia2301 bin vector.
<220> FEATURE:
<221> NAME/KEY: terminator
<222> LOCATION: (233)..(485)
<223> OTHER INFORMATION: Complement of Agrobacterium Nopaline Synthase
      poly-A terminator.
<220> FEATURE:
<221> NAME/KEY: misc_feature
<222> LOCATION: (533)..(1636)
<223> OTHER INFORMATION: Complement of CDS for dao1/ko.
<220> FEATURE:
<221> NAME/KEY: promoter
<222> LOCATION: (1665)..(1952)
<223> OTHER INFORMATION: Complement of promoter from the noplaine
      synthase gene (Depicker et al. 1982, J.Mol.Appl.Genet. 1:561-573)
      EMBL no: V00087.
<220> FEATURE:
<221> NAME/KEY: promoter
<222> LOCATION: (2271)..(3266)
<223> OTHER INFORMATION: Parsley UBI4-2 promoter with internal intron;
      99% homology to #PCCUBI42 P.crispum gene Pcubi4-2 for
      polyubiquitin; from QC28-6/JB010.
<220> FEATURE:
<221> NAME/KEY: misc_feature
<222> LOCATION: (3292)..(5292)
<223> OTHER INFORMATION: gusINT CDS comprise of the E. coli gusA CDS
      containing and internal PIV2 intron.
<220> FEATURE:
<221> NAME/KEY: terminator
<222> LOCATION: (5365)..(5615)
<223> OTHER INFORMATION: Agrobacterium Nopaline Synthase poly-A
      terminator.
<220> FEATURE:
<221> NAME/KEY: misc_feature
<222> LOCATION: (5674)..(5819)
<223> OTHER INFORMATION: Right T-DNA Border; similar to genbank#TIP37TD2
      Ti plasmid (from A. tumefaciens, nopaline strain T37) T-DNA 3'
      (right) border.
<220> FEATURE:
<221> NAME/KEY: misc_feature
<222> LOCATION: (5756)..(5779)
<223> OTHER INFORMATION: Right T-DNA Border repeat region; similar to
      #TIP37TD2; from pCambia2301.

<400> SEQUENCE: 16
gtgattttgt gccgagctgc cggtcgggga gctgttggct ggctggtggc aggatatatt        60
gtggtgtaaa caaattgacg cttagacaac ttaataacac attgcggacg tctttaatgt       120
```

```
actgaattaa catccgtttg atacttgtct aaaattggct gatttcgagt gcatctatgc    180
ataaaaacaa tctaatgaca attattacca agcaggatcc tctagaattc ccgatctagt    240
aacatagatg acaccgcgcg cgataattta tcctagtttg cgcgctatat tttgttttct    300
atcgcgtatt aaatgtataa ttgcgggact ctaatcataa aaacccatct cataaataac    360
gtcatgcatt acatgttaat tattacatgc ttaacgtaat tcaacagaaa ttatatgata    420
atcatcgcaa gaccggcaac aggattcaat cttaagaaac tttattgcca aatgtttgaa    480
cgatcgggga aattcgagct cgccggcgtc gacgatatcc tgcaggtcac taaagttttg    540
actctctcgc tgcaccgtgg tatctttgga atgcctcgtc caccaactga gcaacatctt    600
ctgcagcacc ccatgattgc tgatatccgg cactactaaa accatatgca tgtaccagtg    660
tgacttcttt ttccttagct gcacgtgcgc ttcctcttcc aagcgaaagg gggcttttgg    720
ttctatcgag gggcaataca attctctcag cttctacacg tggtcctcct ctacgagcgg    780
gcctaagacc aacattatgc ctaagtactt cgattccctc aatggttccg tcagatgata    840
tggttgggtc aaggcggagg caatgcttca gaatccgttg gactgtttcg gggttaacgc    900
taagatccca atcacccact ccgtaagttc ctccgcatat aacttcgcca cccggtctcg    960
gtataatata agctggactc gctgggtcac tactatccat cgtacatctt ttgcatggtg   1020 atttaccag cacggtctgg cctctaattg gctccgcagc ttgatcatct atgcctgcta   1080
tgctctttgc tcccagtcct gttgcattca ccacgaggtc tgcaccgtcg aatgcctgtt   1140
ccagtgaggt aaccgtccgt ctttcaaaag ttgcaccgag tttctgaagt tctctggcaa   1200
gatactgaca atatttagga gcgtgtacag agagtgtgtc ataagtcacg ccaattgcgc   1260 ctggtgaca ttcagacgag ggaagggggc ggtaattcgg ggttatatct ttgtaccaat   1320
gtccaagcaa gccgtcttca ttctgtgcaa agcgacgagt tcccttcagc cacatagcat   1380
gtccggtagg gaccaactca acccattttt taaaggtact ctcttcccat tttgcctgtc   1440
tagggccgtc agtcaatgtc ataaatggtg tccaattcgc accagcccag ggggaagcga   1500
aagtttggct agatacgtcc tctgggagat cgcgtgccaa atatgaaca gaatagccct   1560 tgcgtgcaag tataagagca gaagaaagac ctatgactcc cgaacccaat actacaacgc   1620 gttttttgaga gtgcatggtg gcccgggatc cggcgcgcca gatctggatt gagagtgaat   1680
atgagactct aattggatac cgaggggaat ttatggaacg tcagtggagc attttttgaca   1740 agaaatattt gctagctgat agtgacctta ggcgactttt gaacgcgcaa taatggtttc   1800
tgacgtatgt gcttagctca ttaaactcca gaaacccgcg gctgagtggc tccttcaacg   1860
ttgcggttct gtcagttcca aacgtaaaac ggcttgtccc gcgtcatcgg cggggggtcat   1920 aacgtgactc ccttaattct ccgctcatga tcttgatccc ctgcgccatc agatccttgg   1980
cggcaagaaa gccatccagt ttactttgca gggcttccca accttaccag agggcgcccc   2040
agctggcaat tccggttcgc ttgctgtcca taaaaccgcc cagtctagct atcgccatgt   2100
aagcccactg caagctacct gctttctctt tgcgcttgcg ttttcccttg tccagatagc   2160
ccagtagctg acattcatcc ggggtcagca ccgtttctgc ggactggctt tctacgtgtt   2220
ccgcttcctt tagcagccct tgcgccctga gtgcttgcgg cagcgtgaag cttgactaga   2280
gaattcgaat ccaaaaatta cggatatgaa tataggcata tccgtatccg aattatccgt   2340
ttgacagcta gcaacgattg tacaattgct tctttaaaaa aggaagaaag aaagaaagaa   2400
aagaatcaac atcagcgtta acaaacggcc ccgttacggc ccaaacggtc atatagagta   2460
acggcgttaa gcgttgaaag actcctatcg aaatacgtaa ccgcaaacgt gtcatagtca   2520
```

```
gatccnctct tccttcaccg cctcaaacac aaaaataatc ttctacagcc tatatataca   2580
accccccctt ctatctctcc tttctcacaa ttcatcatct ttctttctct accnccaatt   2640
ttaagaaatc ctctcttctc ctcttcattt tcaaggtaaa tctctctctc tctctctctc   2700
tctgttattc cttgttttaa ttaggtatgt attattgcta gtttgttaat ctgcttatct   2760
tatgtatgcc ttatgtgaat atctttatct tgttcatctc atccgtttag aagctataaa   2820
tttgttgatt tgactgtgta tctacacgtg gttatgttta tatctaatca gatatgaatt   2880
tcttcatatt gttgcgtttg tgtgtaccaa tccgaaatcg ttgatttttt tcatttaatc   2940
gtgtagctaa ttgtacgtat acatatggat ctacgtatca attgttcatc tgtttgtgtt   3000
tgtatgtata cagatctgaa aacatcactt ctctcatctg attgtgttgt tacatacata   3060
gatatagatc tgttatatca ttttttttat taattgtgta tatatatatg tgcatagatc   3120
tggattacat gattgtgatt atttacatga ttttgttatt tacgtatgta tatatgtaga   3180
tctggacttt ttggagttgt tgacttgatt gtatttgtgt gtgtatatgt gtgttctgat   3240
cttgatatgt tatgtatgtg cagcccggat ctccgggtag gtcagtccct tatgttacgt   3300
cctgtagaaa ccccaacccg tgaaatcaaa aaactgacg gcctgtgggc attcagtctg   3360
gatcgcgaaa actgtggaat tggtcagcgt tggtgggaaa gcgcgttaca agaaagccgg   3420
gcaattgctg tgccaggcag ttttaacgat cagttcgccg atgcagatat tcgtaattat   3480
gcgggcaacg tctggtatca gcgcgaagtc tttataccga aaggttgggc aggccagcgt   3540
atcgtgctgc gtttcgatgc ggtcactcat tacggcaaag tgtgggtcaa taatcaggaa   3600
gtgatggagc atcagggcgg ctatacgcca tttgaagccg atgtcacgcc gtatgttatt   3660
gccgggaaaa gtgtacgtaa gtttctgctt ctacctttga tatatatata ataattatca   3720
ttaattagta gtaatataat atttcaaata ttttttttcaa aataaaagaa tgtagtatat   3780
agcaattgct tttctgtagt ttataagtgt gtatattta atttataact tttctaaatat   3840 atgaccaaaa tttgttgatg tgcaggtatc accgtttgtg tgaacaacga actgaactgg   3900
cagactatcc cgccgggaat ggtgattacc gacgaaaacg gcaagaaaaa gcagtcttac   3960
ttccatgatt tctttaacta tgccggaatc catcgcagcg taatgctcta caccacgccg   4020
aacacctggg tggacgatat caccgtggtg acgcatgtcg cgcaagactg taaccacgcg   4080
tctgttgact ggcaggtggt ggccaatggt gatgtcagcg ttgaactgcg tgatgcggat   4140
caacaggtgg ttgcaactgg acaaggcact agcgggactt tgcaagtggt gaatccgcac   4200
ctctggcaac cgggtgaagg ttatctctat gaactgtgcg tcacagccaa aagccagaca   4260
gagtgtgata tctacccgct tcgcgtcggc atccggtcag tggcagtgaa gggcgaacag   4320
ttcctgatta ccacaaaacc gttctacttt actggctttg gtcgtcatga agatgcggac   4380
ttgcgtggca aaggattcga taacgtgctg atggtgcacg accacgcatt aatggactgg   4440
attgggccca actcctaccg tacctcgcat taccnttacg ctgaagagat gctcgactgg   4500
gcagatgaac atggcatcgt ggtgattgat gaaactgctg ctgtcggctt taacctctct   4560
ttaggcattg gtttcgaagc gggcaacaag ccgaaagaac tgtacagcga agaggcagtc   4620
aacggggaaa ctcagcaagc gcacttacag gcgattaaag agctgatagc gcgtgacaaa   4680
aaccacccaa gcgtggtgat gtggagtatt gccaacgaac cggatacccg tccgcaaggt   4740
gcacgggaat atttcgcgcc actggcggaa gcaacgcgta actcgacccc gacgcgtccg   4800
atcacctgcg tcaatgtaat gttctgcgac gctcacaccg ataccatcag cgatctcttt   4860
gatgtgctgt gcctgaaccg ttattacgga tggtatgtcc aaagcggcga tttggaaacg   4920
```

```
gcagagaagg tactggaaaa agaacttctg gcctggcagg agaaactgca tcagccgatt    4980
atcatcaccg aatacggcgt ggatacgtta gccgggctgc actcaatgta caccgacatg    5040
tggagtgaag agtatcagtg tgcatggctg gatatgtatc accgcgtctt tgatcgcgtc    5100
agcgccgtcg tcggtgaaca ggtatggaat ttcgccgatt ttgcgacctc gcaaggcata    5160
ttgcgcgttg gcggtaacaa gaaagggatc ttcactcgcg accgcaaacc gaagtcggcg    5220
gcttttctgc tgcaaaaacg ctggactggc atgaacttcg gtgaaaaacc gcagcaggga    5280
ggcaaacaat gaatcaacaa ctctcctggc gcaccatcgt cggctacagc ctcgggaatt    5340
gctaccgagc tcgaatttcc ccgatcgttc aaacatttgg caataaagtt tcttaagatt    5400
gaatcctgtt gccggtcttg cgatgattat catataattt ctgttgaatt acgttaagca    5460
tgtaataatt aacatgtaat gcatgacgtt atttatgaga tgggttttta tgattagagt    5520
cccgcaatta tacatttaat acgcgataga aaacaaaata tagcgcgcaa actaggataa    5580
attatcgcgc gcggtgtcat ctatgttact agatcgggaa ttggcgatcg cagcttggcg    5640
taatcatggt catagctgtt tcctactaga tctgattgtc gtttcccgcc ttcagtttaa    5700
actatcagtt tttgacagga tatattggcg ggtaaaccta agagaaaaga gcgtttatta    5760
gaataatcgg atatttaaaa gggcgtgaaa aggtttatcc gttcgtccat ttgtatgtc    5819

<210> SEQ ID NO 17
<211> LENGTH: 1408
<212> TYPE: DNA
<213> ORGANISM: Arabidopsis thaliana
<220> FEATURE:
<221> NAME/KEY: promoter
<222> LOCATION: (1)..(1408)
<223> OTHER INFORMATION: Arabidopsis thaliana Actin 2 promoter region
      with first intron.
<220> FEATURE:
<221> NAME/KEY: Intron
<222> LOCATION: (955)..(1397)
<223> OTHER INFORMATION: Arabidopsis thaliana Actin 2 first intron

<400> SEQUENCE: 17
tcgacaaaat ttagaacgaa cttaattatg atctcaaata cattgataca tatctcatct      60
agatctaggt tatcattatg taagaaagtt ttgacgaata tggcacgaca aaatggctag     120
actcgatgta attggtatct caactcaaca ttatacttat accaaacatt agttagacaa     180
aatttaaaca actattttt atgtatgcaa gagtcagcat atgtataatt gattcagaat     240
cgttttgacg agttcggatg tagtagtagc cattatttaa tgtacatact aatcgtgaat     300
agtgaatatg atgaaacatt gtatcttatt gtataaatat ccataaacac atcatgaaag     360
acactttctt tcacggtctg aattaattat gatacaattc taatagaaaa cgaattaaat     420
tacgttgaat tgtatgaaat ctaattgaac aagccaacca cgacgacgac taacgttgcc     480
tggattgact cggtttaagt taaccactaa aaaacggag ctgtcatgta acacgcggat      540
cgagcaggtc acagtcatga agccatcaaa gcaaagaac taatccaagg gctgagatga     600
ttaattagtt taaaattag ttaacacgag ggaaaggct gtctgacagc caggtcacgt      660
tatctttacc tgtggtcgaa atgattcgtg tctgtcgatt ttaattattt ttttgaaagg     720
ccgaaaataa agttgtaaga gataaacccg cctatataaa ttcatatatt ttcctctccg     780
ctttgaattg tctcgttgtc ctcctcactt tcatcagccg ttttgaatct ccggcgactt     840
gacagagaag aacaaggaag aagactaaga gagaaagtaa gagataatcc aggagattca     900
ttctccgttt tgaatcttcc tcaatctcat cttcttccgc tctttctttc caaggtaata     960
ggaactttct ggatctactt tatttgctgg atctcgatct tgttttctca atttccttga    1020
```

-continued

```
gatctggaat tcgtttaatt tggatctgtg aacctccact aaatcttttg gttttactag    1080
aatcgatcta agttgaccga tcagttagct cgattatagc taccagaatt tggcttgacc    1140
ttgatggaga gatccatgtt catgttacct gggaaatgat ttgtatatgt gaattgaaat    1200
ctgaactgtt gaagttagat tgaatctgaa cactgtcaat gttagattga atctgaacac    1260
tgtttaaggt tagatgaagt ttgtgtatag attcttcgaa actttaggat ttgtagtgtc    1320
gtacgttgaa cagaaagcta tttctgattc aatcagggtt tatttgactg tattgaactc    1380
tttttgtgtg tttgcagctc ataaaaaa                                        1408
```

<210> SEQ ID NO 18
<211> LENGTH: 19
<212> TYPE: PRT
<213> ORGANISM: Artificial sequence
<220> FEATURE:
<223> OTHER INFORMATION: Consensus motif
<220> FEATURE:
<221> NAME/KEY: MISC_FEATURE
<222> LOCATION: (1)..(2)
<223> OTHER INFORMATION: Xaa is Leu, Ile, Val, or Met
<220> FEATURE:
<221> NAME/KEY: MISC_FEATURE
<222> LOCATION: (4)..(4)
<223> OTHER INFORMATION: Xaa is Asn, His, or Ala
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is Gly, Ser, or Ala
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (12)..(16)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid

<400> SEQUENCE: 18

```
Xaa Xaa His Xaa Tyr Gly Xaa Xaa Xaa Xaa Gly Xaa Xaa Xaa Xaa Xaa
1               5                   10                  15

Gly Xaa Ala
```